United States Patent
Kitchen et al.

(10) Patent No.: US 11,345,957 B2
(45) Date of Patent: May 31, 2022

(54) METHODS OF TREATING GLIOBLASTOMA IN A SUBJECT INFORMED BY EXOSOMAL RNA SIGNATURES

(71) Applicant: Exosome Diagnostics, Inc., Waltham, MA (US)

(72) Inventors: Robert Kitchen, Somerville, MA (US); Michael Valentino, Waltham, MA (US); Johan Skog, Lincoln, MA (US); Vasisht Tadigotla, Newton, MA (US); Dalin Chan, Brighton, MA (US); Sudipto Chakrabortty, Waltham, MA (US); James Hurley, Marblehead, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 205 days.

(21) Appl. No.: 16/631,603

(22) PCT Filed: Jul. 18, 2018

(86) PCT No.: PCT/US2018/042708
§ 371 (c)(1),
(2) Date: Jan. 16, 2020

(87) PCT Pub. No.: WO2019/018537
PCT Pub. Date: Jan. 24, 2019

(65) Prior Publication Data
US 2020/0224245 A1    Jul. 16, 2020

Related U.S. Application Data

(60) Provisional application No. 62/534,141, filed on Jul. 18, 2017.

(51) Int. Cl.
| | | |
|---|---|---|
| C12P 19/34 | (2006.01) | |
| C12Q 1/686 | (2018.01) | |
| C12Q 1/6806 | (2018.01) | |
| C12Q 1/6851 | (2018.01) | |
| C12Q 1/6886 | (2018.01) | |

(52) U.S. Cl.
CPC ........... *C12Q 1/686* (2013.01); *C12Q 1/6806* (2013.01); *C12Q 1/6851* (2013.01); *C12Q 1/6886* (2013.01); *C12Q 2600/158* (2013.01)

(58) Field of Classification Search
CPC .................................................. C12Q 1/6886
See application file for complete search history.

(56) References Cited

U.S. PATENT DOCUMENTS

| | | |
|---|---|---|
| 5,219,727 A | 6/1993 | Wang et al. |
| 5,538,871 A | 7/1996 | Nuovo et al. |
| 5,556,773 A | 9/1996 | Yourno |
| 5,639,606 A | 6/1997 | Willey |
| 6,812,023 B1 | 11/2004 | Lamparski et al. |
| 6,899,863 B1 | 5/2005 | Dhellin et al. |
| 7,198,923 B1 | 4/2007 | Abrignani et al. |
| 2010/0093556 A1 | 4/2010 | Clarke et al. |
| 2012/0164172 A1 | 6/2012 | Farries et al. |
| 2013/0224208 A1 | 8/2013 | Kondo |
| 2014/0011702 A1 | 1/2014 | Mosser et al. |
| 2014/0275073 A1 | 9/2014 | Chang et al. |
| 2015/0038335 A1 | 2/2015 | Skog et al. |
| 2016/0122823 A1* | 5/2016 | Mitsuhashi .......... C12Q 1/6806 514/166 |
| 2016/0235788 A1 | 8/2016 | Hicks et al. |
| 2016/0312211 A1* | 10/2016 | Noerholm ............ C12Q 1/6886 |
| 2018/0224465 A1* | 8/2018 | Goetzl ................. G01N 33/573 |

FOREIGN PATENT DOCUMENTS

| | | |
|---|---|---|
| WO | WO 01/63292 A2 | 8/2001 |
| WO | WO 2009/100029 A1 | 8/2009 |
| WO | WO 2012/031008 A2 | 3/2012 |
| WO | WO 2014/015149 A2 | 1/2014 |
| WO | WO 2014/107571 A1 | 7/2014 |

(Continued)

OTHER PUBLICATIONS

Bronisz, A. et al., "Extracellular Vesicles and MicroRNAs: Their Role in Tumorigenicity and Therapy for Brain Tumors," Cell Mol Neurobiol., 36(3):361-376 (2016); doi:10.1007/s10571-015-0293-4.

De Araujo, M. E. et al., "Polymorphisms in the Gene Region of the Adaptor Complex LAMTOR2/LAMTOR3 and their Association with Breast Cancer Risk," PLoS ONE, 8(1):e53768 (2013), 8 pages; doi: 10.1371/journal.pone.0053768.

Fareh, M. et al., "Cell-based therapy using miR-302-367 expressing cells represses glioblastoma growth," Cell Death and Disease, 8:e2713 (2017), doi:10.1038/cddis.2017.117, 11 pages.

Parplys, A. C. et al., "RAD51AP1-deficiency in vertebrate cells impairs DNA replication," DNA Repair, 24:87-97 (2014).

Al-Nedawi et al., "Intercellular transfer of the oncogenic receptor EGFRvIII by microvesicles derived from tumour cells." Nat Cell Biol. (2008); 10(5): 619-624.

(Continued)

*Primary Examiner* — Kenneth R Horlick
(74) *Attorney, Agent, or Firm* — Cooley LLP; Ivor R. Elrifi; Matthew Pavao

(57) ABSTRACT

The present disclosure relates to methods for treating glioblastoma in a subject in need thereof using gene signatures in exosomal RNA derived from the subject. The gene signatures comprise: at least one of FAM229B, ZNF35, CTD-2647L4.4, CABP5, CYP20A1, CEP126, DTX2P1-UPK3BP1-PMS2P11, RP11-507K12.1, KRBA2, CALD1, LRFN1, RP2, SLC2A13, CDKL3, SLC8A3, ANTXR2, TIGD5, AC074289.1 RP11-932O9.7; at least one of tRNA-Lys-CTT-2-2, tRNA-Pro-AGG-2-7, LAMTOR2, RAD51AP1, DENND2A, A1BG, THSD1, CSF1, RP11-332M2.1, ZNF717, ZNF860, ORC6, C1orf50, PSPH, HIST1H4C, CYP2U1, THAP8, TMEM192, NAA20; or at least one of CREBBP, CXCR2 and S100A9. The treatment methods comprise measuring the expression level of at least one of the aforementioned genes in exosomal RNA from a subject and administering to the subject a glioblastoma treatment based on the expression level(s).

18 Claims, 19 Drawing Sheets

(56) References Cited

FOREIGN PATENT DOCUMENTS

| WO | WO 2015/022545 A2 | 2/2015 |
|---|---|---|
| WO | WO 2015/042570 A1 | 3/2015 |
| WO | WO 2015/152724 A2 | 10/2015 |
| WO | WO 2016/007755 A1 | 1/2016 |
| WO | WO 2016/040892 A1 | 3/2016 |
| WO | WO 2016/172598 A1 | 10/2016 |
| WO | WO 2017/181183 A1 | 10/2017 |
| WO | WO 2019/018537 A1 | 1/2019 |

OTHER PUBLICATIONS

Balzar et al., "The biology of the 17-1A antigen (Ep-CAM)." J Mol Med. (1999); 77(10): 699-712.
Chen et al., "Microfluidic isolation and transcriptome analysis of serum microvesicles." Lab Chip (2010); 10(4): 505-511.
Cheruvanky et al., "Rapid isolation of urinary exosomal biomarkers using a nanomembrane ultrafiltration concentrator." Am J Physiol Renal Physiol. (2007); 292: F1657-F1661.
Dong et al., "Integrated analysis of mutations, miRNA and mRNA expression in glioblastoma," BMC Systems Biology, 4:163 (2010), 20 pages; http://www.biomedcentral.com/1752-0509/4/163.
Dwyer et al., "Glioblastoma Cell-Secreted Interleukin-8 Induces Brain Endothelial Cell Permeability via CXCR2," PLoS ONE 7(9):e45562 (2012), 13 pages; doi: 10.1371/journal.pone.004556.
Geiss et al., "Direct multiplexed measurement of gene expression with color-coded probe pairs," Nature Biotechnology, 26(3):317-325 (2008), and Corrigenda, 1 page.
Guatelli et al., "Isothermal, in vitro amplification of nucleic acids by a multienzyme reaction modeled after retroviral replication," Proc. Natl. Acad. Sci. USA, 87(5):1874-1878 (1990).
Kwoh et al., "Transcription-based amplification system and detection of amplified human immunodeficiency virus type 1 with a bead-based sandwich hybridization format," Proc. Natl. Acad. Sci. USA, 86:1173-1177 (1989).
Li, J. et al., "Replacing PCR with COLD-PCR enriches variant DNA sequences and redefines the sensitivity of genetic testing," Nature Medicine, 14(5):579-584 (2008), and Supplementary Data, 10 pages.
Love et al., "Moderated estimation of fold change and dispersion for RNA-seq data with DESeq2," Genome Biology, 15:550 (2014), 21 pages; doi:10.1186/s13059-014-0550-8.
Miele et al., "Autocatalytic Replication of a Recombinant RNA," J. Mol. Biol., 171:281-295 (1983).
Miranda et al., "Nucleic acids within urinary exosomes/microvesicles are potential biomarkers for renal disease." Kidney International (2010); 78(2): 191-199.
Nilsson et al., "Prostate cancer-derived urine exosomes: a novel approach to biomarkers for prostate cancer." British Journal of Cancer (2009); 100: 1603-1607.
Raposo et al., "B lymphocytes secrete antigen-presenting vesicles." Journal of Experimental Medicine (1996); 183: 1161-1172.
Skog et al., "Glioblastoma microvesicles transport RNA and proteins that promote tumour growth and provide diagnostic biomarkers." Nature Cell Biology (2008); 10(12): 1470-1476.
Taylor and Gercel-Taylor, "MicroRNA signatures of tumor-derived exosomes as diagnostic biomarkers of ovarian cancer." Gynecol Oncol. (2008); 110: 13-21.
Went et al., "Frequent epcam protein expression in human carcinomas." Hum Pathol. (2004); 35:122-128.

* cited by examiner genes differentially expressed between GBM and healthy plasma/serum

METHODS OF TREATING GLIOBLASTOMA IN A SUBJECT INFORMED BY EXOSOMAL RNA SIGNATURES

CROSS-REFERENCE TO RELATED APPLICATIONS

This application is a U.S. National Phase Application, filed under 35 U.S.C. § 371, of International Application No. PCT/US2018/042708, filed on Jul. 18, 2018, which claims priority to, and the benefit of, U.S. Provisional Application No. 62/534,141, filed Jul. 18, 2017, the contents of each of which are incorporated herein by reference in their entireties.

BACKGROUND OF THE INVENTION

Many diseases, including cancer, arise through the accumulation of genetic alterations and subsequent dysregulation of the expression of various genes and pathways. Current methods to identify these genetic alterations in a subject include the analysis of tissue biopsy samples; unfortunately, tissue biopsies are invasive, complicated, and possibly harmful to subjects. However, instances where genetic material can be profiled from biofluids, such as blood, urine, or cerebrospinal fluid, have the advantage of being minimally invasive, being less heterogeneous, providing access to difficult tissues, permitting longitudinal tracking, permitting patient stratification, and enabling earlier disease detection. Liquid biopsies of biofluids contain microvesicles, called exosomes, which are shed by cells and contain nucleic acids and proteins derived from the source cells of the exosomes. Thus, there is a need in the art for methods utilizing biofluid samples, and in particular, the exosomes obtained from liquid biopsies, for the clinical assessment of subjects in need thereof, including diagnosing, monitoring and treating the subject. The present disclosure addresses these needs.

SUMMARY OF THE INVENTION

The present disclosure provides a method comprising: (1) Determining the expression level of at least one gene selected from Table 1 and the expression level of at least one reference gene in a biological sample from a subject; (2) normalizing the expression level of the at least one gene in the biological sample by dividing the expression level of the at least one gene by the expression level of the at least one reference gene; (3) comparing the normalized expression level of the at least one gene in the biological sample to a predetermined cutoff value; and (4) identifying the presence of glioblastoma multiforme in the subject when the normalized expression level of the at least one gene is greater than the predetermined cutoff value, or identifying the absence of glioblastoma multiforme in the subject when the normalized expression level of the at least one gene is equal to or less than the predetermined cutoff value.

The present disclosure provides a method comprising: (1) Determining the expression level of at least one gene selected from Table 2 and the expression level of at least one reference gene in a biological sample from a subject; (2) normalizing the expression level of the at the least one gene in the biological sample by dividing the expression level of the at least one gene by the expression level of the at least one reference gene; (3) comparing the normalized expression level of the at least one gene in the biological sample to a predetermined cutoff value; and (4) identifying the presence of glioblastoma multiforme in the subject when the normalized expression level of the at least one gene is less than the predetermined cutoff value, or identifying the absence of glioblastoma multiforme in the subject when the normalized expression level of the at least one gene is equal to or greater than the predetermined cutoff value.

The at least one reference gene can comprise at least one gene selected from Table 5. The at least one reference gene can be GAPDH.

The at least one reference gene can comprise a gene that has an expression level with a coefficient of variation of less than 20%, or less than 10%, or less than 5% in biological samples from subjects having cancer and biological samples from subjects not having cancer.

The predetermined cutoff value can have a positive predictive value of at least 70%, or at least 80%, or at least 90%, or at least 99%.

The predetermined cutoff value can have a sensitivity of at least 70%, or at least 80%, or at least 90% or at least 99%.

The biological sample can comprise at least one nucleic acid. The at least one nucleic acid can be RNA.

The at least one nucleic acid can be extracted from a microvesicle fraction. The microvesicle fraction can be isolated from a bodily fluid sample selected from blood, plasma, serum, urine or cerebrospinal fluid (CSF) sample.

The microvesicle fraction can be isolated by a method comprising: (a) processing a microvesicle fraction to exclude proteins, lipids, debris from dead cells, and other contaminants; (b) purifying microvesicles using size exclusion chromatography, density gradient centrifugation, centrifugation, differential centrifugation, immunoabsorbent capture, affinity purification, microfluidic separation, ultracentrifugation or a nanomembrane ultrafiltration concentrator; and (c) washing the microvesicles.

Determining the expression level of the at least one gene and the at least one reference gene in step (1) can comprise using quantitative reverse transcription PCR.

Determining the expression level of the at least one gene and the at least one reference gene in step (1) can comprise sequencing. The sequencing can be high-throughput sequencing. The sequencing can comprise performing RNA-SEQ.

The at least one gene can be CREBBP, the at least one reference gene can be GAPDH and the predetermined cutoff value can be at least 0.4.

The at least one gene can be CXCR2, the at least one reference gene can be GAPDH and the predetermined cutoff value can be at least 0.1.

The at least one gene can be S100A9, the at least one reference gene can be GAPDH and the predetermined cutoff value can be at least 1.0.

The present disclosure provides a method comprising: (1) Determining the expression level of at least one gene selected from Table 3 and the expression level of at least one reference gene in a biological sample from a subject having cancer; (2) normalizing the expression level of the at the least one gene in the biological sample by dividing the expression level of the at least one gene by the expression level of the at least one reference gene; (3) comparing the normalized expression level of the at least one gene in the biological sample to a predetermined cutoff value; and (4) recommending initiating an anti-cancer therapy when the normalized expression level of the at least one gene is greater than the predetermined cutoff value, or recommending not initiating an anti-cancer therapy when the normalized expression level of the at least one gene is equal to or less than the predetermined cutoff value.

The at least one gene can be ZNF35, the at least one reference gene can be GAPDH and the predetermined cutoff value can be at least 0.002.

The present disclosure provides a method comprising: (1) Determining the expression level of at least one gene selected from Table 4 and the expression level of at least one reference gene in a biological sample from a subject having cancer; (2) normalizing the expression level of the at the least one gene in the biological sample by dividing the expression level of the at least one gene by the expression level of the at least one reference gene; (3) comparing the normalized expression level of the at least one gene in the biological sample to a predetermined cutoff value; and (4) recommending initiating an anti-cancer therapy when the normalized expression level of the at least one gene is less than the predetermined cutoff value, or recommending not initiating an anti-cancer therapy when the normalized expression level of the at least one gene is equal to or greater than the predetermined cutoff value.

The at least one gene can be LAMTOR2, the at least one reference gene can be GAPDH and the predetermined cutoff value can be at most 0.0125.

The at least one reference gene can comprise at least one gene selected from Table 5. The at least one reference gene can be GAPDH.

The at least one reference gene can comprise a gene that has an expression level with a coefficient of variation of less than 20%, or less than 10%, or less than 5% in biological samples from subjects having cancer and biological samples from subjects not having cancer.

The predetermined cutoff value can have a positive predictive value of at least 70%, or at least 80%, or at least 90%, or at least 99%.

The predetermined cutoff value can have a sensitivity of at least 70%, or at least 80%, or at least 90% or at least 99%.

The biological sample can comprise at least one nucleic acid. The at least one nucleic acid can be RNA.

The at least one nucleic acid can be extracted from a microvesicle fraction. The microvesicle fraction can be isolated from a bodily fluid sample selected from blood, plasma, serum, urine or cerebrospinal fluid (CSF) sample.

The microvesicle fraction can be isolated by a method comprising: (a) processing a microvesicle fraction to exclude proteins, lipids, debris from dead cells, and other contaminants; (b) purifying microvesicles using size exclusion chromatography, density gradient centrifugation, centrifugation, differential centrifugation, immunoabsorbent capture, affinity purification, microfluidic separation, ultracentrifugation or a nanomembrane ultrafiltration concentrator; and (c) washing the microvesicles.

Determining the expression level of the at least one gene and the at least one reference gene in step (1) can comprise using quantitative reverse transcription PCR.

Determining the expression level of the at least one gene and the at least one reference gene in step (1) can comprise sequencing. The sequencing can be high-throughput sequencing. The sequencing can comprise performing RNA-SEQ.

The anti-cancer therapy can comprise administering to the subject a therapeutically effective dose of at least one class of drugs. The at least one class of drugs can comprise tyrosine kinase inhibitors. Tyrosine kinase inhibitors can be epidermal growth factor receptor (EGFR) inhibitors. The EGFR inhibitors can be irreversible EGFR inhibitors. The EGFR inhibitors cane be pan-human epidermal growth factor receptor (pan-HER) inhibitors. The pan-HER inhibitors can be administered in combination with immunotherapy or a checkpoint inhibitor. The pan-HER inhibitor can be Dacomitinib.

The cancer can be brain cancer. The brain cancer can be selected from a group comprising Acoustic Neuroma, Pilocytic Astrocytoma, Low-grade Astrocytoma, Anaplastic Astrocytoma, Glioblastoma multiforme (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Metastatic Brain Tumors, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Primitive Neuroectodermal Tumors (PNET), or Rhabdoid Tumor. The brain cancer can be Glioblastoma multiforme.

The present disclosure provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at the least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) recommending continuing the anti-cancer therapy when the normalized expression level of the at least one gene in the biological sample at least one week after administration of the anti-cancer therapy is greater than the normalized expression level of the at least one gene in the biological sample prior to administration of the anti-cancer therapy, or recommending suspending the anti-cancer therapy when the normalized expression level of the at least one gene in the biological sample at least one week after administration of the anti-cancer therapy is equal to or less than the normalized expression level of the at least one gene in the biological sample prior to administration of the anti-cancer therapy.

The present disclosure provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at the least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) recommending continuing the anti-cancer therapy when the normalized expression level of the at least one gene in the biological sample at least one week after administration of the anti-cancer therapy is less than the normalized expression level of the at least one gene in the biological sample prior to administration of the anti-cancer therapy, or recommending suspending the anti-cancer therapy when the normalized expression level of the at least one gene in the biological sample at least one week after administration of the anti-cancer therapy is equal to or greater than the normalized expression level of the at least one gene in the biological sample prior to administration of the anti-cancer therapy.

The present disclosure provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (2) normalizing the expression level of the at least one gene in the biological sample by dividing the expression level of the at least one gene by the expression level of the at least one reference gene; (3) comparing the normalized expression level of the at least one gene in the biological sample to a predetermined cutoff value; and (4) recommending continuing the anti-cancer therapy when the normalized expression level of the at least one gene in the biological sample is greater than the predetermined cutoff value, or recommending suspending the anti-cancer therapy when the normalized expression level of the at least one gene in the biological sample is equal to or less than the predetermined cutoff value.

The at least one gene can be ZNF35, the at least one reference gene can be GAPDH and the predetermined cutoff value can be at least 0.004.

The at least one gene can be DNMT3A, the at least one reference gene can be GAPDH and the predetermined cutoff value can be at least 0.5.

The present disclosure provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (2) normalizing the expression level of the at least one gene in the biological sample by dividing the expression level of the at least one gene by the expression level of the at least one reference gene; (3) comparing the normalized expression level of the at least one gene in the biological sample to a predetermined cutoff value; and (4) recommending continuing the anti-cancer therapy when the normalized expression level of the at least one gene in the biological sample is less than the predetermined cutoff value, or recommending suspending the anti-cancer therapy when the normalized expression level of the at least one gene in the biological sample is equal to or greater than the predetermined cutoff value.

The present disclosure provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at the least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) generating a score by dividing the normalized expression level of the at least one gene in the biological sample at least one week after administration of the anti-cancer therapy by the normalized expression level of the at least one gene in the biological sample prior to administration of the anti-cancer therapy; (6) comparing the score to a predetermined cutoff value; and (7) recommending continuing the anti-cancer therapy when the score is greater than the predetermined cutoff value, or recommending suspending an anti-cancer therapy when the score is equal to or less than the predetermined cutoff value.

The present disclosure provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at the least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) generating a score by dividing the normalized expression level of the at least one gene in the biological sample at least one week after administration of the anti-cancer therapy by the normalized expression level of the at least one gene in the biological sample prior to administration of the anti-cancer therapy; (6) comparing the score to a predetermined cutoff value; and (7) recommending continuing the anti-cancer therapy when the score is less than the predetermined cutoff value, or recommending suspending anti-cancer therapy when the score is equal to or greater than the predetermined cutoff value.

The at least one reference gene can comprise a gene that has an expression level with a coefficient of variation of less than 20%, or less than 10%, or less than 5% in biological samples from subjects having cancer and biological samples from subjects not having cancer.

The predetermined cutoff value can have a positive predictive value of at least 70%, or at least 80%, or at least 90%, or at least 99%.

The predetermined cutoff value can have a sensitivity of at least 70%, or at least 80%, or at least 90% or at least 99%.

The biological sample can comprise at least one nucleic acid. The at least one nucleic acid can be RNA.

The at least one nucleic acid can be extracted from a microvesicle fraction. The microvesicle fraction can be isolated from a bodily fluid sample selected from blood, plasma, serum, urine or cerebrospinal fluid (CSF) sample.

The microvesicle fraction can be isolated by a method comprising: (a) processing a microvesicle fraction to exclude proteins, lipids, debris from dead cells, and other contaminants; (b) purifying microvesicles using size exclusion chromatography, density gradient centrifugation, centrifugation, differential centrifugation, immunoabsorbent capture, affinity purification, microfluidic separation, ultracentrifugation or a nanomembrane ultrafiltration concentrator; and (c) washing the microvesicles.

Determining the expression level of the at least one gene and the at least one reference gene in step (1) can comprise using quantitative reverse transcription PCR.

Determining the expression level of the at least one gene and the at least one reference gene in step (1) can comprise sequencing. The sequencing can be high-throughput sequencing. The sequencing can comprise performing RNA-SEQ.

The anti-cancer therapy can comprise administering to the subject a therapeutically effective dose of at least one class of drugs. The at least one class of drugs can comprise tyrosine kinase inhibitors. Tyrosine kinase inhibitors can be epidermal growth factor receptor (EGFR) inhibitors. The EGFR inhibitors can be irreversible EGFR inhibitors. The EGFR inhibitors cane be pan-human epidermal growth factor receptor (pan-HER) inhibitors. The pan-HER inhibitors can be administered in combination with immunotherapy or a checkpoint inhibitor. The pan-HER inhibitor can be Dacomitinib.

The cancer can be brain cancer. The brain cancer can be selected from a group comprising Acoustic Neuroma, Pilocytic Astrocytoma, Low-grade Astrocytoma, Anaplastic Astrocytoma, Glioblastoma multiforme (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Metastatic Brain Tumors, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Primitive Neuroectodermal Tumors (PNET), or Rhabdoid Tumor. The brain cancer can be Glioblastoma multiforme.

Suspending the anti-cancer therapy can comprise ceasing the anti-cancer therapy.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
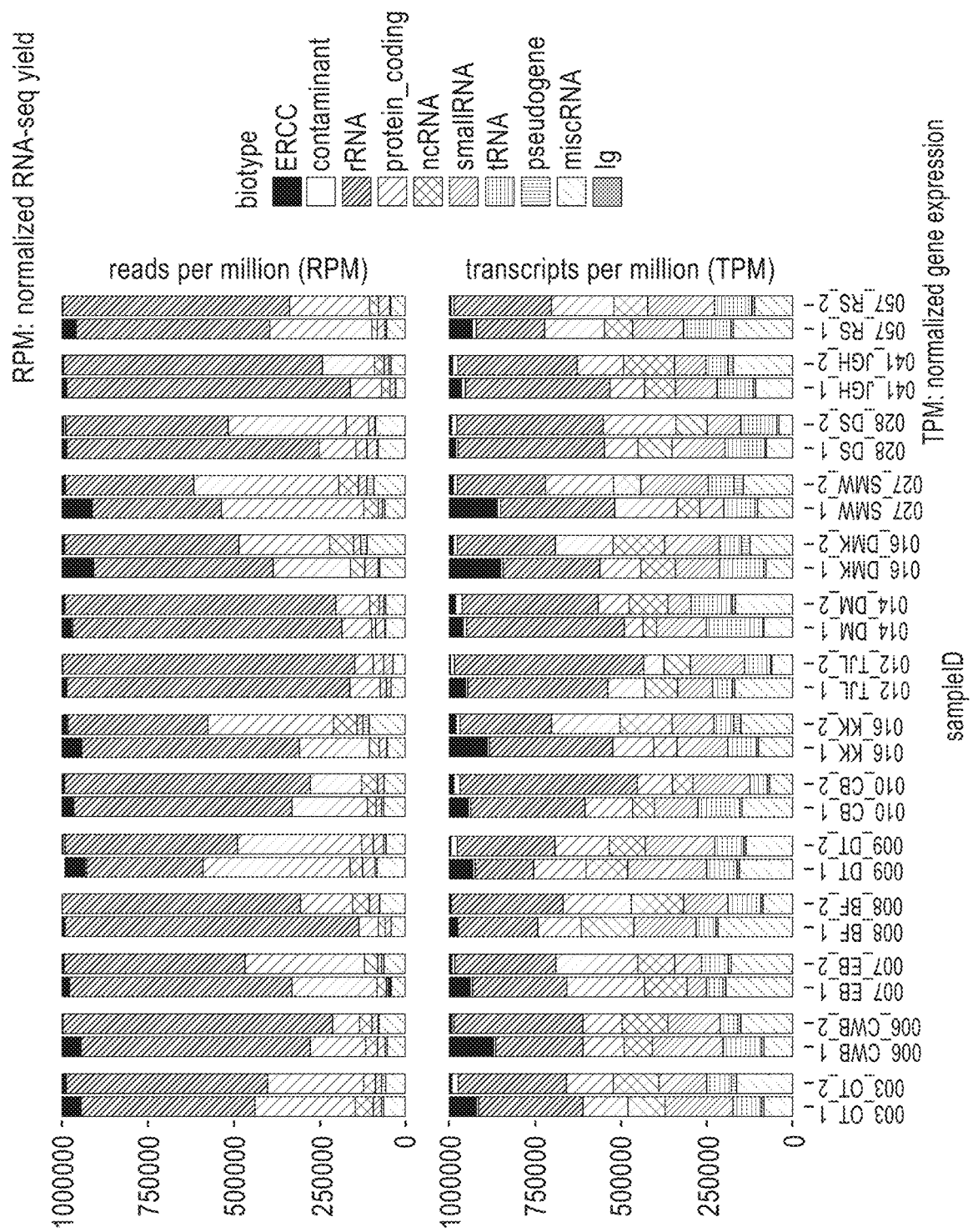
FIG. 1 is a series of charts showing the number of reads per million and number of transcripts per million for each RNA biotype in serum exosome samples from 14 patients at the pre-treatment (sample ID suffix: '_1') and post-treatment (sample ID suffix: '_2') timepoints.

The present disclosure provides methods for providing a clinical assessment of a subject in need therefore. The clinical assessment can include, but is not limited to, diagnosing a subject, monitoring a subject, recommending a treatment for a subject or prognosing a subject. In some aspects, the clinical assessment is informed by the analysis of the contents of microvesicles.

Microvesicles are shed by eukaryotic and prokaryotic cells, or budded off of the plasma membrane, to the exterior of the cell. These membrane vesicles are heterogeneous in size with diameters ranging from about 10 nm to about 5000 nm. All membrane vesicles shed by cells <0.8 µm in diameter are referred to herein collectively as "exosomes", "extracellular vesicles", or "microvesicles." These extracellular vesicles (EVs) include microvesicles, microvesicle-like particles, prostasomes, dexosomes, texosomes, ectosomes, oncosomes, apoptotic bodies, retrovirus-like particles, and human endogenous retrovirus (HERV) particles. Small microvesicles (approximately 10 to 1000 nm, and more often 30 to 200 nm in diameter) that are released by exocytosis of intracellular multivesicular bodies are referred to in the art as "microvesicles". Microvesicles shed by cells are also herein referred to as "exosomes".

Exosomes are known to contain nucleic acids, including various DNA and RNA types such as mRNA (messenger RNA), miRNA (micro RNA), tRNA (transfer RNA), piRNA (piwi-interacting RNA), snRNA (small nuclear RNA), snoRNA (small nucleolar RNA), and rRNA (ribosomal RNA), various classes of long non-coding RNA, including long intergenic non-coding RNA (lincRNA) as well as proteins. Recent studies reveal that nucleic acids within microvesicles have a role as biomarkers. For example, WO 2009/100029 describes, among other things, the use of nucleic acids extracted from microvesicles in Glioblastoma multiforme (GBM, a particularly aggressive form of cancer) patient serum for medical diagnosis, prognosis and therapy evaluation. WO 2009/100029 also describes the use of nucleic acids extracted from microvesicles in human urine for the same purposes. The use of nucleic acids extracted from microvesicles is considered to potentially circumvent the need for biopsies, highlighting the enormous diagnostic potential of microvesicle biology (Skog et al. *Nature Cell Biology*, 2008, 10(12): 1470-1476.

Microvesicles can be isolated from liquid biopsy samples from a subject, involving biofluids such as whole blood, serum, plasma, urine, and cerebrospinal fluid (CSF). The nucleic acids contained within the microvesicles can subsequently be extracted. The extracted nucleic acids, e.g., exosomal RNA, also referred to herein as "exoRNA," can be further analyzed based on detection of a biomarker or a combination of biomarkers. The analysis can be used to generate a clinical assessment that diagnoses a subject with a disease, predicts the disease outcome of the subject, stratifies the subject within a larger population of subjects, predicts whether the subject will respond to a particular therapy, or determines if a subject is responding to an administered therapy.

Various methods of the present disclosure are described in full detail herein.

In one aspect, the present disclosure provides a method comprising: (1) Determining the expression level of at least one gene selected from Table 1 and the expression level of at least one reference gene in a biological sample from a subject; (2) normalizing the expression level of the at least one gene in the biological sample by dividing the expression level of the at least one gene by the expression level of the at least one reference gene; (3) comparing the normalized expression level of the at least one gene in the biological sample to a predetermined cutoff value; and (4) identifying the presence of glioblastoma multiforme in the subject when the normalized expression level of the at least one gene is greater than the predetermined cutoff value, or identifying the absence of glioblastoma multiforme in the subject when the normalized expression level of the at least one gene is equal to or less than the predetermined cutoff value.

In some aspects of the preceding method, the at least one gene can be CREBBP, the at least one reference gene can be GAPDH and the predetermined cutoff value can be at least 0.4. In another aspect, the at least one gene can be CXCR2, the at least one reference gene is GAPDH and the predetermined cutoff value can be at least 0.1. In yet another aspect, the at least one gene can be S100A9, the at least one reference gene can be GAPDH and the predetermined cutoff value can be at least 1.0.

In some aspects of the preceding method, step (4) can comprise producing a report identifying the presence of glioblastoma multiforme in the subject when the normalized expression level of the at least one gene is greater than the predetermined cutoff value, or producing a report identifying the absence of glioblastoma multiforme in the subject when the normalized expression level of the at least one gene is equal to or less than the predetermined cutoff value.

In some aspects, step (1) of the preceding method can comprise determining the expression level of at least one gene, or at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes, or at least 17 genes, or at least 18 genes, or at least 19 genes, or at least 20 genes, or at least 21 genes, or at least 22 genes, or at least 23 genes, or at least 24 genes, or at least 25 genes, or at least 26 genes, or at least 27 genes, or at least 28 genes, or at least 29 genes, or at least 30 genes, or at least 31 genes, or at least 32 genes, or at least 33 genes, or at least 34 genes, or at least 35 genes, or at least 36 genes, or at least 37 genes, or at least 38 genes, or at least 39 genes, or at least 40 genes, or at least 41 genes, or at least 42 genes, or at least 43 genes, or at least 44 genes, or at least 45 genes, or at least 45 genes, or at least 46 genes, or at least 47 genes, or at least 48 genes, or at least 49 genes, or at least 50 genes, or at least 51 genes, or at least 52 genes, or at least 53 genes, or at least 54 genes, or at least 55 genes, or at least 56 genes, or at least 57 genes, or at least 58 genes, or at least 59 genes, or at least 60 genes, or at least 61 genes, or at least 62 genes, or at least 63 genes, or at least 64 genes, or at least 65 genes, or at least 66 genes, or at least 67 genes, or at least 68 genes, or at least 69 genes, or at least 70 genes, or at least 71 genes, or at least 72 genes, or at least 73 genes, or at least 74 genes, or at least 75 genes, or at least 76 genes, or at least 77 genes, or at least 78 genes, or at least 79 genes, or at least 80 genes, or at least 81 genes, or at least 82 genes, or at least 83 genes, or at least 84 genes, or at least 85 genes, or at least 86 genes, or at least 87 genes, or at least 88 genes, or at least 89 genes, or at least 90 genes, or at least 91 genes, or at least 92 genes, or at least 93 genes, or at least 94 genes, or at least 95 genes, or at least 96 genes, or at least 97 genes, or at least 98 genes, or at least 99 genes, or at least 100 genes, or at least 101 genes, or at least 102 genes, or at least 103 genes, or at least 104 genes, or at least 105 genes, or at least 106 genes, or at least 107 genes, or at least 108 genes, or at least 109 genes, or at least 110 genes, or at least 111 genes, or at least 112 genes, or at least 113 genes, or at least 114 genes, or at least 115 genes, or at least 116 genes, or at least 117 genes, or at least 118 genes, or at least 119 genes, or at least 200 genes, or at least 300 genes, or at least 400 genes, or at least 500 genes, or at least 600 genes, or at least 700 genes, or at least 800 genes, or at least 900 genes, or at least 1000 genes, or at least 1100 genes, or at least 1200 genes, or at least 1300 genes or at least 1326 genes selected from the genes listed in Table 1.

In another aspect, the present disclosure provides a method comprising: (1) Determining the expression level of at least one gene selected from Table 2 and the expression level of at least one reference gene in a biological sample from a subject; (2) normalizing the expression level of the at the least one gene in the biological sample by dividing the expression level of the at least one gene by the expression level of the at least one reference gene; (3) comparing the normalized expression level of the at least one gene in the biological sample to a predetermined cutoff value; and (4) identifying the presence of glioblastoma multiforme in the subject when the normalized expression level of the at least one gene is less than the predetermined cutoff value, or identifying the absence of glioblastoma multiforme in the subject when the normalized expression level of the at least one gene is equal to or greater than the predetermined cutoff value.

In some aspects of the preceding method, step (4) can comprise producing a report identifying the presence of glioblastoma multiforme in the subject when the normalized expression level of the at least one gene is less than the predetermined cutoff value, or producing a report identifying the absence of glioblastoma multiforme in the subject when the normalized expression level of the at least one gene is equal to or greater than the predetermined cutoff value.

In some aspects, step (1) of the preceding method can comprise determining the expression level of at least one gene, or at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes, or at least 17 genes, or at least 18 genes, or at least 19 genes, or at least 20 genes, or at least 21 genes, or at least 22 genes, or at least 23 genes, or at least 24 genes, or at least 25 genes, or at least 26 genes, or at least 27 genes, or at least 28 genes, or at least 29 genes, or at least 30 genes, or at least 31 genes, or at least 32 genes, or at least 33 genes, or at least 34 genes, or at least 35 genes, or at least 36 genes, or at least 37 genes, or at least 38 genes, or at least 39 genes, or at least 40 genes, or at least 41 genes, or at least 42 genes, or at least 43 genes, or at least 44 genes, or at least 45 genes, or at least 45 genes, or at least 46 genes, or at least 47 genes, or at least 48 genes, or at least 49 genes, or at least 50 genes, or at least 51 genes, or at least 52 genes, or at least 53 genes, or at least 54 genes, or at least 55 genes, or at least 56 genes, or at least 57 genes, or at least 58 genes, or at least 59 genes, or at least 60 genes, or at least 61 genes, or at least 62 genes, or at least 63 genes, or at least 64 genes, or at least 65 genes, or at least 66 genes, or at least 67 genes, or at least 68 genes, or at least 69 genes, or at least 70 genes, or at least 71 genes, or at least 72 genes, or at least 73 genes, or at least 74 genes, or at least 75 genes, or at least 76 genes, or at least 77 genes, or at least 78 genes, or at least 79 genes, or at least 80 genes, or at least 81 genes, or at least 82 genes, or at least 83 genes, or at least 84 genes, or at least 85 genes, or at least 86 genes, or at least 87 genes, or at least 88 genes, or at least 89 genes, or at least 90 genes, or at least 91 genes, or at least 92 genes, or at least 93 genes, or at least 94 genes, or at least 95 genes, or at least 96 genes, or at least 97 genes, or at least 98 genes, or at least 99 genes, or at least 100 genes, or at least 101 genes, or at least 102 genes, or at least 103 genes, or at least 104 genes, or at least 105 genes, or at least 106 genes, or at least 107 genes, or at least 108 genes, or at least 109 genes, or at least 110 genes, or at least 111 genes, or at least 112 genes, or at least 113 genes, or at least 114 genes, or at least 115 genes, or at least 116 genes, or at least 117 genes, or at least 118 genes, or at least 119 genes, or at least 200 genes, or at least 300 genes or at least 381 genes selected from the genes listed in Table 2.

In another aspect, the present disclosure provides a method comprising: (1) Determining the expression level of at least one gene selected from Table 3 and the expression level of at least one reference gene in a biological sample from a subject having cancer; (2) normalizing the expression level of the at the least one gene in the biological sample by dividing the expression level of the at least one gene by the expression level of the at least one reference gene; (3) comparing the normalized expression level of the at least one gene in the biological sample to a predetermined cutoff value; and (4) recommending initiating an anti-cancer therapy when the normalized expression level of the at least one gene is greater than the predetermined cutoff value, or recommending not initiating an anti-cancer therapy when the normalized expression level of the at least one gene is equal to or less than the predetermined cutoff value.

In some aspects of the preceding method, step (4) can comprise producing a report recommending initiating an anti-cancer therapy when the normalized expression level of the at least one gene is greater than the predetermined cutoff value, or producing a report recommending not initiating an anti-cancer therapy when the normalized expression level of the at least one gene is equal to or less than the predetermined cutoff value.

In a preferred aspect of the preceding method, the at least one gene can be ZNF35, the at least one reference gene can be GAPDH and the predetermined cutoff value can be at least 0.002.

In some aspects, step (1) of the preceding method can comprise determining the expression level of at least one gene, or at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes, or at least 17 genes, or at least 18 genes or at least 19 genes selected from the genes listed in Table 3.

In another aspect, the present disclosure provides a method comprising: (1) Determining the expression level of at least one gene selected from Table 4 and the expression level of at least one reference gene in a biological sample from a subject having cancer; (2) normalizing the expression level of the at the least one gene in the biological sample by dividing the expression level of the at least one gene by the expression level of the at least one reference gene; (3) comparing the normalized expression level of the at least one gene in the biological sample to a predetermined cutoff value; and (4) recommending initiating an anti-cancer therapy when the normalized expression level of the at least one gene is less than the predetermined cutoff value, or recommending not initiating an anti-cancer therapy when the normalized expression level of the at least one gene is equal to or greater than the predetermined cutoff value.

In some aspects of the preceding method, step (4) can comprise producing a report recommending initiating an anti-cancer therapy when the normalized expression level of the at least one gene is less than the predetermined cutoff value, or producing a report recommending not initiating an anti-cancer therapy when the normalized expression level of the at least one gene is equal to or greater than the predetermined cutoff value.

In a preferred aspect of the preceding method, the at least one gene can be LAMTOR2, the at least one reference gene can be GAPDH and the predetermined cutoff value can be at most 0.0125.

In some aspects, step (1) of the preceding method can comprise determining the expression level of at least one gene, or at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes, or at least 17 genes, or at least 18 genes or at least 19 genes selected from the genes listed in Table 4.

In some aspects, the present disclosure provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at the least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) recommending continuing the anti-cancer therapy when the normalized expression level of the at least one gene in the biological sample at least one week after administration of the anti-cancer therapy is greater than the normalized expression level of the at least one gene in the biological sample prior to administration of the anti-cancer therapy, or recommending suspending the anti-cancer therapy when the normalized expression level of the at least one gene in the biological sample at least one week after administration of the anti-cancer therapy is equal to or less than the normalized expression level of the at least one gene in the biological sample prior to administration of the anti-cancer therapy.

In some aspects of the preceding method, step (5) can comprise producing a report recommending continuing the anti-cancer therapy when the normalized expression level of the at least one gene in the biological sample at least one week after administration of the anti-cancer therapy is greater than the normalized expression level of the at least one gene in the biological sample prior to administration of the anti-cancer therapy, or producing a report recommending suspending the anti-cancer therapy when the normalized expression level of the at least one gene in the biological sample at least one week after administration of the anti-cancer therapy is equal to or less than the normalized expression level of the at least one gene in the biological sample prior to administration of the anti-cancer therapy.

In some aspects, step (2) of the preceding method can comprise determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least two weeks, or at least three weeks, or at least four weeks (at least one month), or at least two months, or at least three months, or at least five months, or at least six months, or at least seven months, or at least eight months, or at least nine months, or at least ten months, or at least eleven months, or at least twelve months (at least one year), or at least two years, or at least three years, or at least four years, or at least five years, or at least 10 years after administration of the anti-cancer therapy.

In some aspects, step (1) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy.

In some aspects, step (2) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy.

The present disclosure also provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) recommending continuing the anti-cancer therapy when the normalized expression level of the at least one gene in the biological sample at least one week after administration of the anti-cancer therapy is less than the normalized expression level of the at least one gene in the biological sample prior to administration of the anti-cancer therapy, or recommending suspending the anti-cancer therapy when the normalized expression level of the at least one gene in the biological sample at least one week after administration of the anti-cancer therapy is equal to or greater than the normalized expression level of the at least one gene in the biological sample prior to administration of the anti-cancer therapy.

In aspects of the preceding method, step (5) can comprise producing a report recommending continuing the anti-cancer therapy when the normalized expression level of the at least one gene in the biological sample at least one week after administration of the anti-cancer therapy is less than the normalized expression level of the at least one gene in the biological sample prior to administration of the anti-cancer therapy, or producing a report recommending suspending the anti-cancer therapy when the normalized expression level of the at least one gene in the biological sample at least one week after administration of the anti-cancer therapy is equal to or greater than the normalized expression level of the at least one gene in the biological sample prior to administration of the anti-cancer therapy.

In some aspects, step (2) of the preceding method can comprise determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least two weeks, or at least three weeks, or at least four weeks (at least one month), or at least two months, or at least three months, or at least five months, or at least six months, or at least seven months, or at least eight months, or at least nine months, or at least ten months, or at least eleven months, or at least twelve months (at least one year), or at least two years, or at least three years, or at least four years, or at least five years, or at least 10 years after administration of the anti-cancer therapy.

In some aspects, step (1) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B or LAMTOR2 and the expression level of at least one reference gene in a biological sample from a subject having cancer and prior to administration of an anti-cancer therapy.

In some aspects, step (2) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy.

The present disclosure also provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (2) normalizing the expression level of the at least one gene in the biological sample by dividing the expression level of the at least one gene by the expression level of the at least one reference gene; (3) comparing the normalized expression level of the at least one gene in the biological sample to a predetermined cutoff value; and (4) recommending continuing the anti-cancer therapy when the normalized expression level of the at least one gene in the biological sample is greater than the predetermined cutoff value, or recommending suspending the anti-cancer therapy when the normalized expression level of the at least one gene in the biological sample is equal to or less than the predetermined cutoff value.

In aspects of the preceding method, step (4) can comprise producing a report recommending continuing the anti-cancer therapy when the normalized expression level of the at least one gene in the biological sample is greater than the predetermined cutoff value, or producing a report recommending suspending the anti-cancer therapy when the normalized expression level of the at least one gene in the biological sample is equal to or less than the predetermined cutoff value.

In preferred aspects of the preceding method, the at least one gene can be ZNF302, the at least one reference gene can be GAPDH and the predetermined cutoff value can be at least 0.004.

In another preferred aspect of the preceding method, the at least on gene can be DNMT3A, the at least one reference gene can be GAPDH and the predetermined cutoff value can be at least 0.5.

In some aspects, step (1) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy.

In some aspects, step (1) of the preceding method can comprise determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least two weeks, or at least three weeks, or at least four weeks (at least one month), or at least two months, or at least three months, or at least five months, or at least six months, or at least seven months, or at least eight months, or at least nine months, or at least ten months, or at least eleven months, or at least twelve months (at least one year), or at least two years, or at least three years, or at least four years, or at least five years, or at least 10 years after administration of the anti-cancer therapy.

The present disclosure also provides a method comprising (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (2) normalizing the expression level of the at least one gene in the biological sample by dividing the expression level of the at least one gene by the expression level of the at least one reference gene; (3) comparing the normalized expression level of the at least one gene in the biological sample to a predetermined cutoff value; and (4) recommending continuing the anti-cancer therapy when the normalized expression level of the at least one gene in the biological sample is less than the predetermined cutoff value, or recommending suspending the anti-cancer therapy when the normalized expression level of the at least one gene in the biological sample is equal to or greater than the predetermined cutoff value.

In some aspects of the preceding method, step (4) can comprise producing a report recommending continuing the anti-cancer therapy when the normalized expression level of the at least one gene in the biological sample is less than the predetermined cutoff value, or producing a report recommending suspending the anti-cancer therapy when the normalized expression level of the at least one gene in the biological sample is equal to or greater than the predetermined cutoff value.

In some aspects, step (1) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy.

In some aspects, step (1) of the preceding method can comprise determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least two weeks, or at least three weeks, or at least four weeks (at least one month), or at least two months, or at least three months, or at least five months, or at least six months, or at least seven months, or at least eight months, or at least nine months, or at least ten months, or at least eleven months, or at least twelve months (at least one year), or at least two years, or at least three years, or at least four years, or at least five years, or at least 10 years after administration of the anti-cancer therapy.

The present disclosure also provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at the least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) generating a score by dividing the normalized expression level of the at least one gene in the biological sample at least one week after administration of the anti-cancer therapy by the normalized expression level of the at least one gene in the biological sample prior to administration of the anti-cancer therapy; (6) comparing the score to a predetermined cutoff value; and (7) recommending continuing the anti-cancer therapy when the score is greater than the predetermined cutoff value, or recommending suspending an anti-cancer therapy when the score is equal to or less than the predetermined cutoff value.

In some aspects of the preceding method, step (7) can comprise producing a report recommending continuing the anti-cancer therapy when the score is greater than the predetermined cutoff value, or producing a report recommending suspending an anti-cancer therapy when the score is equal to or less than the predetermined cutoff value.

In some aspects, step (2) of the preceding method can comprise determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least two weeks, or at least three weeks, or at least four weeks (at least one month), or at least two months, or at least three months, or at least five months, or at least six months, or at least seven months, or at least eight months, or at least nine months, or at least ten months, or at least eleven months, or at least twelve months (at least one year), or at least two years, or at least three years, or at least four years, or at least five years, or at least 10 years after administration of the anti-cancer therapy.

In some aspects, step (1) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy.

In some aspects, step (2) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy.

The present disclosure also provides a method comprising: (1) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy; (2) Determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy; (3) normalizing the expression level of the at the least one gene in the biological sample prior to administration of the anti-cancer therapy by dividing the expression level of the at least one gene in the biological sample prior to administration of the anti-cancer therapy by the expression level of the at least one reference gene in the biological sample prior to administration of the anti-cancer therapy; (4) normalizing the expression level of the at least one gene in the biological sample at least one week after administration of the anti-cancer therapy by dividing the expression level of the at least one gene in the biological sample at least one week after administration of an anti-cancer therapy by the expression level of the at least one reference gene in the biological sample at least one week after administration of the anti-cancer therapy; and (5) generating a score by dividing the normalized expression level of the at least one gene in the biological sample at least one week after administration of the anti-cancer therapy by the normalized expression level of the at least one gene in the biological sample prior to administration of the anti-cancer therapy; (6) comparing the score to a predetermined cutoff value; and (7) recommending continuing the anti-cancer therapy when the score is less than the predetermined cutoff value, or recommending suspending anti-cancer therapy when the score is equal to or greater than the predetermined cutoff value.

In some aspects of the preceding method, step (7) can comprise producing a report recommending continuing the anti-cancer therapy when the score is less than the predetermined cutoff value, or producing a report recommending suspending anti-cancer therapy when the score is equal to or greater than the predetermined cutoff value.

In some aspects, step (2) of the preceding method can comprise determining the expression level of at least one gene selected from ZNF302, DNMT3A, BHLHA15, CTD-2132N18.3, ADORA2B, LAMTOR2, or ZNF35 and the expression level of at least one reference gene in a biological sample from a subject having cancer and at least two weeks, or at least three weeks, or at least four weeks (at least one month), or at least two months, or at least three months, or at least five months, or at least six months, or at least seven months, or at least eight months, or at least nine months, or at least ten months, or at least eleven months, or at least twelve months (at least one year), or at least two years, or at least three years, or at least four years, or at least five years, or at least 10 years after administration of the anti-cancer therapy.

In some aspects, step (1) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and prior to administration of an anti-cancer therapy.

In some aspects, step (2) of the preceding method can comprise determining the expression level of at least two genes, or at least three genes, or at least four genes, or at least five genes, or at least six genes or at least seven genes selected from ZNF302, DNMT3A, BHLHA15, CTD-2132N18.3, ADORA2B, LAMTOR2, or ZNF35 and the expression level of at least one reference gene in a biological sample from a subject having cancer and at least one week after administration of the anti-cancer therapy.

In some aspects of the methods of the present disclosure, the at least one reference gene comprises a gene that has an expression level with a coefficient of variation of less than 20%, or less than 10%, or less than 5% in biological samples from subjects having cancer and biological samples from subjects not having cancer.

In some aspects of the methods of the present disclosure, the predetermined cutoff value has a positive predictive value of at least 70%, or at least 80%, or at least 90%, or at least 99%.

In some aspects of the methods of the present disclosure, the predetermined cutoff value has a sensitivity of at least 70%, or at least 80%, or at least 90%, or at least 99%.

In some aspects of the methods of the present disclosure, the biological sample can comprise at least one nucleic acid. The at least one nucleic acid can be RNA, DNA or a combination of RNA and DNA.

In some aspects of the methods of the present disclosure wherein the biological sample comprises at least one nucleic acid, the at least one nucleic acid can be extracted from a microvesicle fraction. The microvesicle fraction can be isolated from a bodily fluid sample selected from a blood, plasma, serum, urine, or CSF. In preferred aspects, a microvesicle fraction can be isolated by a method comprising: (a) processing a microvesicle fraction to exclude proteins, lipids, debris from dead cells, and other contaminants; (b) purifying microvesicles using size exclusion chromatography, density gradient centrifugation, centrifugation, differential centrifugation, immunoabsorbent capture, affinity purification, microfluidic separation, ultracentrifugation or a nanomembrane ultrafiltration concentrator; and (c) washing the microvesicles.

In some aspects of the methods of the present disclosure, determining the expression level of the at least one gene and the at least one reference gene in the preceding methods comprises using quantitative reverse transcription PCR. In other aspects, determining the expression level of the at least one gene and the at least one reference gene in the preceding methods can comprise using direct detection methods. In yet another aspect, determining the expression level of the at least one gene and the at least one reference gene in the preceding methods can comprise sequencing. The sequencing can be high-throughput sequencing. In aspects comprising sequencing, the sequencing can comprise performing RNA-SEQ.

In some aspects of the methods of the present disclosure, an anti-cancer therapy can comprise administering to the subject a therapeutically effective dose of at least one class of drugs. The one class of drugs can comprise tyrosine kinase inhibitors. The tyrosine kinase inhibitors can comprise epidermal growth factor receptor (EGFR) inhibitors. The EGFR inhibitors can comprise irreversible EGFR inhibitors. The EGFR inhibitors can comprise pan-human epidermal growth factor receptor (pan-HER) inhibitors. A pan-HER inhibitor can comprise Dacomitinib. A pan-HER inhibitor can be administered in combination with immunotherapy or a checkpoint inhibitor.

In some aspects of the methods of the present disclosure, the cancer can be brain cancer. Brain cancer can include, but is not limited to Acoustic Neuroma, Pilocytic Astrocytoma, Low-grade Astrocytoma, Anaplastic Astrocytoma, Glioblastoma multiforme (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Metastatic Brain Tumors, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Primitive Neuroectodermal Tumors (PNET), or Rhabdoid Tumor. In preferred aspects, the brain cancer is glioblastoma multiforme.

In some aspects of the methods of the present disclosure, an at least one reference gene can comprise any gene selected from Table 5. Preferably, the at least one reference gene comprises GAPDH, ACTB, VIM, EEF2, RPS2, RPS3, RPL15, RPL22, UBC or NCL. Most preferably, the at least one reference gene comprises GAPDH.

In some aspects of the methods of the present disclosure, a predetermined cutoff value can be the ratio of the expression level of a gene to the expression level of a reference gene.

In some aspects of the methods of the present disclosure, suspending the anti-cancer therapy can comprise ceasing the anti-cancer therapy.

In aspects of the methods of the present disclosure, samples from a subject can be analyzed using the methods of the present disclosure any time after the administration of an anti-cancer therapy. Results from the analysis at one time point after the administration of an anti-cancer therapy can be compared to the results of analyses of samples from any number of other time points after the administration of anti-cancer therapy and/or the results of the analyses of samples from any number of time points before the administration of cancer therapy.

Definitions

As used herein, a "subject" or "patient" can be any mammal, e.g., a human, a primate, mouse, rat, dog, cat, cow, horse, pig, sheep, goat, camel. In a preferred aspect, the subject is a human. A subject can be diagnosed with cancer. The subject can be diagnosed with brain cancer.

The sample can be a biological sample. As will be appreciated by those in the art, the sample may comprise any number of things, including, but not limited to: cells (including both primary cells and cultured cell lines) and tissues (including cultured or explanted). In aspects, a tissue sample (fixed or unfixed) is embedded, serially sectioned, and immobilized onto a microscope slide. As is well known, a pair of serial sections will include at least one cell that is present in both serial sections. Structures and cell types, located on a first serial section will have a similar location on an adjacent serial section. The sample can be cultured cells or dissociated cells (fixed or unfixed) that have been immobilized onto a slide. The biological sample may suitably comprise a bodily fluid from a subject. The bodily fluids can be fluids isolated from anywhere in the body of the subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

The sample can be obtained from virtually any organism including multicellular organisms, e.g., of the plant, fungus, and animal kingdoms; preferably, the sample is obtained from an animal, e.g., a mammal. Human samples are particularly preferred.

In some aspects, the preceding methods are used in the clinical assessment of a subject. As used herein the term "clinical assessment of a subject" can comprise producing a report that predicts or diagnoses a condition in a subject, determine a subject's predisposition to a condition, monitors the treatment of a condition in a subject, diagnoses a therapeutic response of a disease in a subject and prognoses the disease, disease progression, or response to particular treatment of a disease in a subject.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer or cervical cancer.

A cancer can be a brain cancer. Types of brain tumors and cancer are well known in the art. Glioma is a general name for tumors that arise from the glial (supportive) tissue of the brain. Gliomas are the most common primary brain tumors. Astrocytomas, ependymomas, oligodendrogliomas, and tumors with mixtures of two or more cell types, called mixed gliomas, are the most common gliomas. Brain cancers can include, but are not limited to Acoustic Neuroma, Pilocytic Astrocytoma, Low-grade Astrocytoma, Anaplastic Astrocytoma, Glioblastoma multiforme (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Metastatic Brain Tumors, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Primitive Neuroectodermal Tumors (PNET), or Rhabdoid Tumor.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "response" or "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/ or decreased mortality at a given point of time following treatment.

The term "anti-cancer therapy" is used in the broadest sense and refers to any method known in the art for the treatment of cancer. Anti-cancer therapy can include, but is not limited to, the administration of chemotherapeutic agents, the administration of anti-cancer agents, radiation treatment, immunotherapy, surgery, radiation therapy, targeted therapy, hormone therapy and stem cell transplant. Anti-cancer therapy can comprise administering to the subject a therapeutically effective dose of at least one class of drugs. The terms "effective amount" and "therapeutically effective amount" of a drug, agent or compound of the invention is meant a nontoxic but sufficient amount of the drug, agent or compound to provide the desired effect, for example, a response or benefit in the subject.

"Initiating an anti-cancer therapy" is used in its broadest sense and refers to starting any method known in the art for the treatment of cancer and continuing the method for any length of time.

Classes of anti-cancer agents can include, but are not limited to, tyrosine kinase inhibitors. Tyrosine kinase inhibitors can include, but are not limited to, epidermal growth factor receptor (EGFR) inhibitors. EGFR inhibitors can include, but are not limited to, pan-human epidermal growth factor receptor (pan-HER) inhibitors. Pan-HER inhibitors can include, but are not limited to Dacomitinib, afatinib, neratinib.

Classes of anti-cancer agents can include, but are not limited to, antibodies.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Immunotherapy can include the administration of an antibody or antibody fragment.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one aspect, the extent of binding of an anti-target antibody to an unrelated, non-target protein is less than about 10% of the binding of the antibody to target as measured, e.g., by a radioimmunoassay (RIA) or biacore assay. In certain aspects, an antibody that binds to a target has a dissociation constant (Kd) of <1 μM, <100 nM, <10 nM, <1 nM, <0.1 nM, <0.01 nM, or <0.001 nM (e.g. $10^8$ M or less, e.g. from $10^8$ M to $10^{13}$ M, e.g., from $10^9$ M to $10^{13}$ M). In certain aspects, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some aspects, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Classes of anti-cancer or chemotherapeutic agents can include alkylating agents, platinum agents, taxanes, *vinca* agents, anti-estrogen drugs, aromatase inhibitors, ovarian suppression agents, endocrine/hormonal agents, bisphophonate therapy agents and targeted biological therapy agents.

Specific anti-cancer or chemotherapeutic agents can include cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

Combinational anti-cancer or chemotherapeutic therapies can include AT: Adriamycin® (Doxorubicin) and Taxotere® (Docetaxel); AC: Adriamycin®, Cytoxan® (Cyclophosphamide); AC+Taxol®; AC+Taxotere®; CMF: Cytoxan®, Methotrexate, 5-fluorouracil; CEF: Cytoxan®, Ellence® (Epirubicin), and fluorouracil; EC: Ellence®, Cytoxan®; FAC: 5-fluorouracil, Adriamycin®, and Cytoxan®; GET: Gemzar® (Gemcitabine), Ellence®, and Taxol®; TC: Taxotere®, Cytoxan®; TC: Taxotere®, Paraplatin® (Carboplatin); TAC: Taxotere®, Adriamycin®, Cytoxan® or TCH: Taxotere®, Herceptin® (Trastuzumab), and Paraplatin®. Additional combination chemotherapeutic therapies for cancer can include: Taxol® and Xeloda® (Capecitabine); Taxotere® and Xelode; Taxotere® and Paraplatie; Taxol® and Paraplatie; Taxol® and Gemzar®; Abraxane® (Protein-bound Paclitaxel) and Xelode; Abraxane® and Paraplatie; Camptosor® (Irinotecan) and Temodar® (Temozolomide); Gemzar® and Paraplatin® or Ixempra® (Ixabepilone) and Xeloda®

The methods of the present disclosure can include a recommendation of treatment, and may further comprising administering a treatment to a subject to whom a recommendation of treatment was provided. The treatment can include any anti-cancer therapy or any combination of anti-cancer therapy.

As used herein, "treating" or "treat" describes the management and care of a patient for the purpose of combating a disease, condition, or disorder and includes, but is not limited to, the administration of chemotherapy, immunotherapy, radiotherapy, or a combination thereof, to alleviate the symptoms or complications of a disease, condition or disorder, or to eliminate the disease, condition or disorder.

As used herein, the term "alleviating" or "alleviate" is meant to describe a process by which the severity of a sign or symptom of a disorder is decreased. Importantly, a sign or symptom can be alleviated without being eliminated.

A chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Any-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PM-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SM-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-B, MT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

General Methods

Determining Gene Expression Levels

In methods of the present disclosure, expression levels of genes can be measured using any methods known in the art. These methods include, but are not limited to sequencing, direct detection, and amplification-based methods.

In aspects with direct detections methods, the extracted nucleic acids, including DNA and/or RNA, are analyzed directly without an amplification step. Direct analysis may be performed with different methods including, but not limited to, the NanoString technology. NanoString technology enables identification and quantification of individual target molecules in a biological sample by attaching a color coded fluorescent reporter to each target molecule. These methods are described in Geiss et al. (see Geiss et al. *Nature Biotechnology*, 2008, 26(3): 317-325), which is incorporated herein by reference.

In other aspects, it may be beneficial or otherwise desirable to amplify the nucleic acid of the microvesicle prior to analyzing it. Methods of nucleic acid amplification are commonly used and generally known in the art. If desired, the amplification can be performed such that it is quantitative. Quantitative amplification will allow quantitative determination of relative amounts of the various nucleic acids, to generate a profile.

In one embodiment, the extracted nucleic acid is RNA. RNA molecules are then preferably reverse-transcribed into complementary DNAs before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods.

The analysis of nucleic acids present in the microvesicles is quantitative and/or qualitative. For quantitative analysis, the amounts (expression levels), either relative or absolute, of specific nucleic acids of interest within the microvesicles are measured with methods known in the art (described below). For qualitative analysis, the species of specific nucleic acids of interest within the microvesicles, whether wild type or variants, are identified with methods known in the art (described below).

Sequencing methods can include, but are not limited to RNA-seq. In some aspects, RNA-seq comprises reverse transcribing at least one RNA molecule to produce at least one double-stranded complementary DNA molecule (dscDNA). Methods known in the art for creating a dscDNA library may be used. RNA-seq can further comprise appending sequencing adaptors to the at least one dscDNA molecule, followed by amplification, and finally sequencing. Methods of sequencing known in the art, including sequencing by synthesis can be used. The various RNA-seq methods known in the art may be used. Base abundances obtained using RNA-seq methods can be measured as read counts and normalized using methods known in the art (e.g. Love, M I, Huber W, and Anders, S, "Moderated estimation of fold change and dispersion for RNA-seq data with DESeq2", *Genome Biology*, 2015 15:500, herein incorporated by reference). Gene abundances can also be reported in Reads Per Million (RPM) or Transcripts Per Million (TPM).

In some aspects, "next-generation" sequencing (NGS) or high-throughput sequencing experiments are performed. These sequencing techniques allow for the identification of nucleic acids present in low or high abundance in a sample, or which are otherwise not detected by more conventional hybridization methods or a quantitative PCR method. NGS typically incorporates the addition of nucleotides followed by washing steps.

Commercially available kits for total RNA SEQUENCING which preserves the strand information, meant for mammalian RNA and very low input RNA are useful in this regard, and include, without limitation, Clontech: SMARTer stranded total RNASeq kit; Clontech: SMARTSeq v4 ultra low input RNASeq kit; Illumina: Truseq stranded total RNA library prep kit; Kapa Biosystems: Kapa stranded RNASeq library preparation kit; New England Biolabs: NEBNext ultra directional library prep kit; Nugen: Ovation Solo RNASeq kit; and Nugen: Nugen Ovation RNASeq system v2.

The methods of the present disclosure can use reference genes to normalize the measured abundance of other genes and biomarkers. Normalization can be used to control for experimental variation to facilitate more accurate comparisons between measurements from different samples. In a non-limiting example, a first sample from a first patient and a second sample from a second patient are analyzed. The first sample from the first patient may be more concentrated than the second sample from the second patient, meaning more nucleic acids are extracted from the first sample than are extracted from the second sample. Thus, if the expression level of a particular gene is measured in the two samples, the expression level of the gene will appear higher in the first sample than the second sample, simply because there are more nucleic acid molecule in the first sample. To more accurately compare between the two samples, the two measured expression levels can be normalized.

Normalization can also be used to control for unwanted biological variation. In a non-limiting example, biological variation can result from some feature of the patient or the sample collection that is not relevant to the methods of the present disclosure, such as blood-exosome concentration due to high or low blood pressure, variations created by collecting samples at different times of the day and variation to due patient age or patient sex.

In methods of the present disclosure, the measured expression level of a particular gene can be normalized using methods known in the art. In a non-limiting example, normalization can be achieved by dividing the measured expression level of a gene of interest by a reference gene. Useful reference genes are genes that show a low variation in their expression level across a variety of different samples and patients. For example, a useful reference gene will show the same expression level in samples derived from subjects who have cancer and in samples derived from subjects who do not have cancer. In another example, a useful reference gene will show the same expression level in samples derived from a subject with cancer before treatment with an anti-cancer therapy and in in samples derived from a subject with cancer after treatment with an anti-cancer therapy. The variation in expression level can be quantified by different methods known in the art. For example, the variation in expression level of a gene can be quantified by calculating the coefficient of variation in the expression level of a particular gene across a set of different samples.

Isolation of Microvesicles

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

In some aspects, the sample isolation and analysis techniques encompass the methods referred to as EXO50 and/or EXO52 as described in, e.g., WO 2014/107571 and WO 2016/007755, each incorporated by reference herein in the entirety. Also contemplated are the commercially available liquid biopsy platforms sold under the trademarks EXOLUTION™, EXOLUTION PLUS™, EXOLUTION™ UPREP, EXOLUTION HT™, UPREP™, EXOEASY™, EXORNEASY™, each available from Exosome Diagnostics, Inc., as well as the QIAamp Circulating Nucleic Acids Kit, DNeasy Blood & Tissue Kits, AllPrep DNA/RNA Mini Kit, and the AllPrep DNA/RNA/Protein Mini Kit, each available from Qiagen.

The isolation methods for exosomes for the further purification of extracellular vesicles having associated nucleic acids described herein also include: 1) Ultracentrifugation, often in combination with sucrose density gradients or sucrose cushions to float the relatively low-density exosomes. Isolation of exosomes by sequential differential centrifugations, combined with sucrose gradient ultracentrifugation, can provide high enrichment of exosomes. 2) The use of volume-excluding polymer selected from the group consisting of polyethylene glycol, dextran, dextran sulfate, dextran acetate, polyvinyl alcohol, polyvinyl acetate, or polyvinyl sulfate; and wherein the molecular weight of the volume-excluding polymer is from 1000 to 35000 daltons performed in conjunction with the additive sodium chloride from 0-1M. 3) Size exclusion chromatography, for example, Sephadex™ G200 column matrix. 4) Selective immunoaffinity or charge-based capture using paramagnetic beads (including immuno-precipitation), for example, by using antibodies directed against the surface antigens including but not limited to EpCAM, CD326, KSA, TROP1. The selection antibodies can be conjugated to paramagnetic microbeads. 5) Direct precipitation with chaotropic agents such as guanidinium thiocyanate.

Isolation of microvesicles can be achieved via a membrane as the capture surface, although it should be understood that the format of the capturing surface, e.g., beads or a filter (also referred to herein as a membrane), does not affect the ability of the methods provided herein to efficiently capture extracellular vesicles from a biological sample.

In aspects where the capture surface is a membrane, the device for isolating the extracellular vesicle fraction from a biological sample contains at least one membrane. In some aspects, the device comprises one, two, three, four, five or six membranes. In some aspects, the device comprises three membranes. In aspects where the device comprises more than one membrane, the membranes are all directly adjacent to one another at one end of the column. In aspects where the device comprises more than one membrane, the membranes are all identical to each other, i.e., are of the same charge and/or have the same functional group.

It should be noted that capture by filtering through a pore size smaller than the extracellular vesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use samples isolated by any of a variety of capture surfaces. In some aspects, the capture surface is a membrane, also referred to herein as a filter or a membrane filter. In some aspects, the capture surface is a commercially available membrane. In some aspects, the capture surface is a charged commercially available membrane. In some aspects, the capture surface is neutral. In some aspects, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In aspects where the capture surface is charged, the capture surface can be a charged filter selected from the group consisting of 0.65 um positively charged Q PES vacuum filtration (Millipore), 3-5 um positively charged Q RC spin column filtration (Sartorius), 0.8 um positively charged Q PES homemade spin column filtration (Pall), 0.8 um positively charged Q PES syringe filtration (Pall), 0.8 um negatively charged S PES homemade spin column filtration (Pall), 0.8 um negatively charged S PES syringe filtration (Pall), and 50 nm negatively charged nylon syringe filtration (Sterlitech). In some aspects, the charged filter is not housed in a syringe filtration apparatus, as nucleic acid can be harder to get out of the filter in these aspects. In some aspects, the charged filter is housed at one end of a column.

In aspects where the capture surface is a membrane, the membrane can be made from a variety of suitable materials. In some aspects, the membrane is polyethersulfone (PES) (e.g., from Millipore or PALL Corp.). In some aspects, the membrane is regenerated cellulose (RC) (e.g., from Sartorius or Pierce).

In some aspects, the capture surface is a positively charged membrane. In some aspects, the capture surface is a Q membrane, which is a positively charged membrane and is an anion exchanger with quaternary amines. For example, the Q membrane is functionalized with quaternary ammonium, $R-CH_2-N^+(CH_3)_3$. In some aspects, the capture surface is a negatively charged membrane. In some aspects, the capture surface is an S membrane, which is a negatively charged membrane and is a cation exchanger with sulfonic acid groups. For example, the S membrane is functionalized with sulfonic acid, $R-CH_2-SO_3^-$. In some aspects, the capture surface is a D membrane, which is a weak basic anion exchanger with diethylamine groups, $R-CH_2-NH^+(C_2H_5)_2$. In some aspects, the capture surface is a metal chelate membrane. For example, the membrane is an IDA membrane, functionalized with minodiacetic acid $-N(CH_2COOH^-)_2$. In some aspects, the capture surface is a microporous membrane, functionalized with aldehyde groups, $-CHO$. In other aspects, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In aspects where the capture surface is charged, extracellular vesicles can be isolated with a positively charged filter.

In aspects where the capture surface is charged, the pH during extracellular vesicle capture is a pH≤7. In some aspects, the pH is greater than 4 and less than or equal to 8.

In aspects where the capture surface is a positively charged Q filter, the buffer system includes a wash buffer comprising 250 mM Bis Tris Propane, pH 6.5-7.0. In aspects where the capture surface is a positively charged Q filter, the lysis buffer is a GTC-based reagent. In aspects where the capture surface is a positively charged Q filter, the lysis buffer is present at one volume. In aspects where the capture surface is a positively charged Q filter, the lysis buffer is present at more than one volume.

Depending on the membrane material, the pore sizes of the membrane range from 3 μm to 20 nm. For example, in aspects where the capture surface is a commercially available PES membrane, the membrane has a pore size of 20 nm (Exomir), 0.65 μm (Millipore) or 0.8 μm (Pall). In aspects where the capture surface is a commercially available RC membrane, the membrane has a pore size in the range of 3-5 µm (Sartorius, Pierce).

The surface charge of the capture surface can be positive, negative or neutral. In some aspects, the capture surface is a positively charged bead or beads.

In some aspects, the sample is not pre-processed prior to isolation of microvesicles and extraction of nucleic acids, e.g., DNA and/or DNA and RNA, from the biological sample.

In some aspects, the sample is subjected to a pre-processing step prior to isolation, purification or enrichment of the extracellular vesicles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof.

Where more than one centrifugation pre-processing steps are performed, the biological sample may be centrifuged first at the lower speed and then at the higher speed. If desired, further suitable centrifugation pre-processing steps may be carried out. Alternatively, or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 µm filter.

In some aspects, the sample is pre-filtered to exclude particles larger than 0.8 µm. In some aspects, the sample includes an additive such as EDTA, sodium citrate, and/or citrate-phosphate-dextrose. In some aspects, the sample does not contain heparin, as heparin can negatively impact RT-qPCR and other nucleic acid analysis. In some aspects, the sample is mixed with a buffer prior to purification and/or nucleic acid isolation and/or extraction. In some aspects, the buffer is a binding buffer.

In some aspects, one or more centrifugation steps are performed before or after contacting the biological sample with the capture surface to separate extracellular vesicles and concentrate the extracellular vesicles isolated from the biological fraction. To remove large unwanted particles, cells, and/or cell debris, the samples may be centrifuged at a low speed of about 100-500 g, for example, in some aspects, about 250-300 g. Alternatively or in addition, the samples may be centrifuged at a higher speed. Suitable centrifugation speeds are up to about 200,000 g; for example, from about 2,000 g to less than about 200,000 g. Speeds of above about 15,000 g and less than about 200,000 g or above about 15,000 g and less than about 100,000 g or above about 15,000 g and less than about 50,000 g are used in some aspects. Speeds of from about 18,000 g to about 40,000 g or about 30,000 g; and from about 18,000 g to about 25,000 g are more preferred. In some aspects, a centrifugation speed of about 20,000 g. Generally, suitable times for centrifugation are from about 5 minutes to about 2 hours, for example, from about 10 minutes to about 1.5 hours, or from about 15 minutes to about 1 hour. A time of about 0.5 hours may be used. It is sometimes useful, in some aspects, to subject the biological sample to centrifugation at about 20,000 g for about 0.5 hours. However, the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., for example, about 1-5° C., e.g., about 3° C. or about 4° C.

In some aspects, one or more filtration steps are performed before or after contacting the biological sample with the capture surface. A filter having a size in the range about 0.1 to about 1.0 µm may be employed, for example, about 0.8 µm or 0.22 µm. The filtration may also be performed with successive filtrations using filters with decreasing porosity.

In some aspects, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the extracellular vesicles. This may consist of a series of differential centrifugations. The extracellular vesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the extracellular vesicle fraction. In another embodiment, the filtration is an ultrafiltration, for example, a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the invention, the use of membranes with a cut-off threshold below 1000 kDa, for example, in some aspects, between 100 kDa and 1000 kDa, or for example, in some aspects, between 100 kDa and 600 kDa, is advantageous.

In some aspects, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate copolymer or mixtures thereof, e.g., agarose-dextran mixtures, are used in some aspects. For example, such supports include, but are not limited to: SUPERDEX® 200HR (Pharmacia), TSK G6000 (TosoHaas) or SEPHACRYL® S (Pharmacia).

In some aspects, one or more affinity chromatography steps are performed before or after contacting the biological sample with the capture surface. Some extracellular vesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of lung, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

Extraction of Nucleic Acids

Following the isolation of extracellular vesicles from a biological sample, nucleic acid may be extracted from the isolated or enriched extracellular vesicle fraction. To achieve this, the extracellular vesicles may first be lysed. The lysis of extracellular vesicles and extraction of nucleic acids may be achieved with various methods known in the art, including those described in PCT Publication Nos. WO 2016/007755 and WO 2014/107571, the contents of each of which are hereby incorporated by reference in their entirety. Nucleic acid extraction may be achieved using protein precipitation according to standard procedures and techniques known in the art. Such methods may also utilize a nucleic acid-binding column to capture the nucleic acids contained within the extracellular vesicles. Once bound, the nucleic acids can then be eluted using a buffer or solution suitable to disrupt the interaction between the nucleic acids and the binding column, thereby eluting the nucleic acids.

Exosomal derived nucleic acids can include RNA or DNA, either individually or as a mixture of RNA and DNA. Exosomal derived nucleic acids can include material either contained within or bound to the outer surface of exosomes. The DNA component can be exosomal or other cell-free sources (cfDNA).

Where an extracellular vesicle fraction is utilized, isolation and extraction of nucleic acids, e.g., DNA and/or DNA and nucleic acids including at least RNA from a sample using the following general procedure. First, the nucleic acids in the sample, e.g., the DNA and/or the DNA and the extracellular vesicle fraction, are bound to a capture surface such as a membrane filter, and the capture surface is washed. Then, an elution reagent is used to perform on-membrane lysis and release of the nucleic acids, e.g., DNA and/or DNA and RNA, thereby forming an eluate. The eluate is then contacted with a protein precipitation buffer that includes a transition metal and a buffering agent. The cfDNA and/or DNA and nucleic acids include at least the RNA from the extracellular vesicles is then isolated from the protein-precipitated eluate using any of a variety of art-recognized techniques, such as, for example, binding to a silica column followed by washing and elution.

The elution buffer may comprise a denaturing agent, a detergent, a buffer substance, and/or combinations thereof to maintain a defined solution pH. The elution buffer may include a strong denaturing agent, or even a strong denaturing agent and a reduction agent.

In some aspects, one or more control particles or one or more nucleic acid(s) may be added to the sample prior to extracellular vesicle isolation and/or nucleic acid extraction to serve as an internal control to evaluate the efficiency or quality of extracellular vesicle purification and/or nucleic acid extraction. The methods described herein provide for the efficient isolation and the control nucleic acid(s) along with the extracellular vesicle fraction. These control nucleic acid(s) include one or more nucleic acids from Q-beta bacteriophage, one or more nucleic acids from virus particles, or any other control nucleic acids (e.g., at least one control target gene) that may be naturally occurring or engineered by recombinant DNA techniques. In some aspects, the quantity of control nucleic acid(s) is known before the addition to the sample. The control target gene can be quantified using real-time PCR analysis. Quantification of a control target gene can be used to determine the efficiency or quality of the extracellular vesicle purification or nucleic acid extraction processes.

In some aspects, the control nucleic acid is a nucleic acid from a Q-beta bacteriophage, referred to herein as "Q-beta control nucleic acid." The Q-beta control nucleic acid used in the methods described herein may be a naturally-occurring virus control nucleic acid or may be a recombinant or engineered control nucleic acid. Q-beta is a member of the leviviridae family, characterized by a linear, single-stranded RNA genome that consists of 3 genes encoding four viral proteins: a coat protein, a maturation protein, a lysis protein, and RNA replicase. When the Q-beta particle itself is used as a control, due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. When the Q-beta particle itself is used as a control, after addition of the Q-beta particles to the biological sample, the nucleic acids from the Q-beta particle are extracted along with the nucleic acids from the biological sample using the extraction methods described herein. When a nucleic acid from Q-beta, for example, RNA from Q-beta, is used as a control, the Q-beta nucleic acid is extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added or the copy number detected and the quantity of Q-beta nucleic acid, for example, Q-beta RNA, added can be compared to determine the quality of the isolation and/or extraction process.

In some aspects, 50, 100, 150, 200, 250, 300, 350, 400, 450, 500, 1,000 or 5,000 copies of Q-beta particles or Q-beta nucleic acid, for example, Q-beta RNA, added to a bodily fluid sample. In some aspects, 100 copies of Q-beta particles or Q-beta nucleic acid, for example, Q-beta RNA, are added to a bodily fluid sample. When the Q-beta particle itself is used as control, the copy number of Q-beta particles can be calculated based on the ability of the Q-beta bacteriophage to infect target cells. Thus, the copy number of Q-beta particles is correlated to the colony forming units of the Q-beta bacteriophage.

Optionally, control particles may be added to the sample prior to extracellular vesicle isolation or nucleic acid extraction to serve as an internal control to evaluate the efficiency or quality of extracellular vesicle purification and/or nucleic acid extraction. The methods described herein provide for the efficient isolation and the control particles along with the extracellular vesicle fraction. These control particles include Q-beta bacteriophage, virus particles, or any other particle that contains control nucleic acids (e.g., at least one control target gene) that may be naturally occurring or engineered by recombinant DNA techniques. In some aspects, the quantity of control particles is known before the addition to the sample. The control target gene can be quantified using real-time PCR analysis. Quantification of a control target gene can be used to determine the efficiency or quality of the extracellular vesicle purification or nucleic acid extraction processes.

In some aspects, the Q-beta particles are added to the urine sample prior to nucleic extraction. For example, the Q-beta particles are added to the urine sample prior to ultrafiltration and/or after the pre-filtration step.

In some aspects, the methods and kits described herein include one or more in-process controls. In some aspects, the in-process control is detection and analysis of a reference gene that indicates sample quality (i.e., an indicator of the quality of the biological sample, e.g., biofluid sample). In some aspects, the in-process control is detection and analysis of a reference gene that indicates plasma quality (i.e., an indicator of the quality of the plasma sample). In some aspects, the reference gene(s) is/are analyzed by additional qPCR.

In some aspects, the in-process control is an in-process control for reverse transcriptase and/or PCR performance. These in-process controls include, by way of non-limiting examples, a reference RNA (also referred to herein as ref.RNA), that is spiked in after RNA isolation and prior to reverse transcription. In some aspects, the ref RNA is a control such as Qbeta. In some aspects, the ref RNA is analyzed by additional PCR.

In some aspects, a spike-in of synthetic RNA or DNA standard, also referred to herein as a "synthetic spike-in" is included as a quality control metric, or at any step prior to sequencing library preparation. Exogenous materials such as synthetic nucleic acids, can serve as sample quality control reagents, quantification reagents, can enable limit of detection, dynamic range and technical reproducibility studies and/or can enable studies detecting particular sequences.

Commercially available synthetic spike-ins include, without limitation, Dharmacon: Solaris RNA spike-in control kit; Exiqon: RNA spike-in kit; Horizon Diagnostics: Reference standards, Lexogen: spike-in RNA variant control mixes; Thermo Fisher Scientific: ERCC RNA spike-in control mixes; and Qbeta RNA spike-in, yeast or *Arabidopsis* RNA.

In some aspects, the synthetic spike-ins is added to the sample at different dilutions. In some aspects, the dilution of the spike-ins to be added to the sample can be in the range of 1:1000 to 1:10,000,000, including, without limitation, dilutions of 1:1000, 1:10,000, 1:100,000, 1:1,000,000 and even 1:10,000,000. The specific dilution of spike-ins to be added to the sample is determined based on the quantity and/or the quality and/or source of the nucleic acids present in the sample.

In some aspects, the sample can either be subjected to a reverse transcription reaction or untreated. The RNA within a sample is reverse transcribed when it is of interest to convert the RNA to cDNA. In some aspects, only first stand synthesis is conducted when only single stranded cDNA is desired. In some aspects, both first strand and second strand synthesis is conducted when double stranded DNA is desired. In some aspects, the sample is untreated when it is of interest to only investigate DNA fractions within the sample. In some aspects, the cDNA processing steps include, for example but not limited to retaining strand information by treating with uracil-N-glycosylase and/or by orientation of NGS adapter sequences, cleavage of RNA, fragmentation of RNA, incorporation of non-canonical nucleotides, annealing or ligation of adapter sequences (adaptor ligation), second strand synthesis, etc.

In some aspects, the sample is subjected to fragmentation or untreated. Fragmentation can be achieved using enzymatic or non-enzymatic processes or by physical shearing of the material with RNA or dsDNA. In some aspects, fragmentation of the RNA and/or dsDNA is conducted by heat denaturation in the presence of divalent cations. The specific duration of fragmentation time of the sample is determined based on the quantity and/or the quality and/or source of the nucleic acids present in the sample. In some aspects, the duration of fragmentation time ranges from 0 minute to 30 minutes.

In some aspects, sequencing adaptors are added to the material using ligation based approaches following end-repair and adenylation, such as polyadenylation. In some aspects, sequencing adaptors are added to the material using PCR-based approaches. Nucleic acids within the sample, which have gone through any of the aspects described above and now have sequence adaptors will hereto be described as 'library' when referring to the entire collection of nucleic acid fragments within the sample or 'library fragment' when referring to the fragment of nucleic acid that has been incorporated within the context of the sequence adaptors. Inclusion of unique molecular index (UMI), unique identifier, or molecular tag in the adapter sequence provides an added benefit for read de-duplication and enhanced estimation of the input number of nucleic acid molecules in the sample.

In some aspects, using bead-based separation techniques, the library can be subjected to a process whereby composition of the library can be further modified to: 1) remove unwanted products (including but not restricted to; residual adaptors, primers, buffers, enzymes, adaptor dimers); 2) be of a certain size range (by altering the bead or bead buffer reagent to sample ratio, low and/or high molecular weight products can be either included or excluded in the sample); 3) concentrate the sample by elution in minimal volume. This process is commonly referred to as a 'clean up' step or the sample is 'cleaned up' and will hereto be referred to as such. Bead-based separation techniques can include but are not limited to paramagnetic beads. Bead-based clean up can be conducted once or multiple times if required or desired.

Commercially available paramagnetic beads useful according to the methods herein include, without limitation, Beckman Coulter: Agencourt AMPure XP; Beckman Coulter: Agencourt RNAclean XP; Kapa Biosystems: Kapa Pure beads; Omega Biosystems: MagBind TotalPure NGS beads; and ThermoFisher Scientific: Dynabeads.

Following bead-based clean up, the library can be amplified en masse using universal primers that target the adaptor sequence. The number of amplification cycles can be modified to produce enough product that is required for downstream processing steps.

Library quantity and quality is quantified using, but not limited to, fluorometric techniques such as Qubit dsDNA HS assay and/or Agilent Bioanalyzer HS DNA assay. The libraries can then be normalized, multiplexed and subjected to sequencing on any next generation sequencing platform.

In some aspects, the extracted nucleic acid comprises DNA and/or DNA and RNA. In aspects where the extracted nucleic acid comprises DNA and RNA, the RNA is reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct values are inversely proportional to the amount of target nucleic acid, or control nucleic acid, in the sample (i.e., the lower the Ct value, the greater the amount of control nucleic acid in the sample).

In another aspect, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

Any of the above aspects and embodiments can be combined with any other aspect or embodiment as disclosed here in the Summary and/or Detailed Description sections.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present disclosure, the preferred materials and methods are described herein. It is to be understood that the terminology used herein is for the purpose of describing particular aspects only, and is not intended to be limiting.

EXAMPLES

Example 1—Analyzing Exosomal RNA from 14 Glioblastoma Multiforme Patients Pre-Treatment and after Treatment with Dacomitinib Serum samples were collected from 14 patients diagnosed with glioblastoma mutliforme (GBM) before the administration of Dacomitinib (pre-treatment samples) and 1 month after the initiation of Dacomitinib treatment (post-treatment samples). Of the 14 patients, 7 were deemed to be "responders" to the drug and stayed on the drug for more than 6 months.

Exosomal RNA was extracted from the patient samples and subjected to total RNA-seq with rRNA depletion. On average, 10-20 million mapped reads were obtained per sample.

During data analysis, quality control was monitored by analyzing the number of detected genes in each sample as well as by sample clustering. In each sample, the percentage of the RNA-seq signal attributable to mRNA varies between 10-50% and appears to vary by individual patient.

The main determinant of RNA read yield was ribosomal RNA (rRNA), which represented a large portion of the sequencing output.

The analysis showed that one could reliably detect in excess of 10,000 different mRNA genes in all of the samples. Additionally, one could detect approximately 2,000 genes of various non-coding biotypes, such as pseudogenes, long intergenic noncoding RNAs (lincRNAs) and antisense transcripts. There were also a small set of other RNA biotypes detected, including small nuclear RNA (snRNA) and transfer RNA (tRNA).

Figure 2:
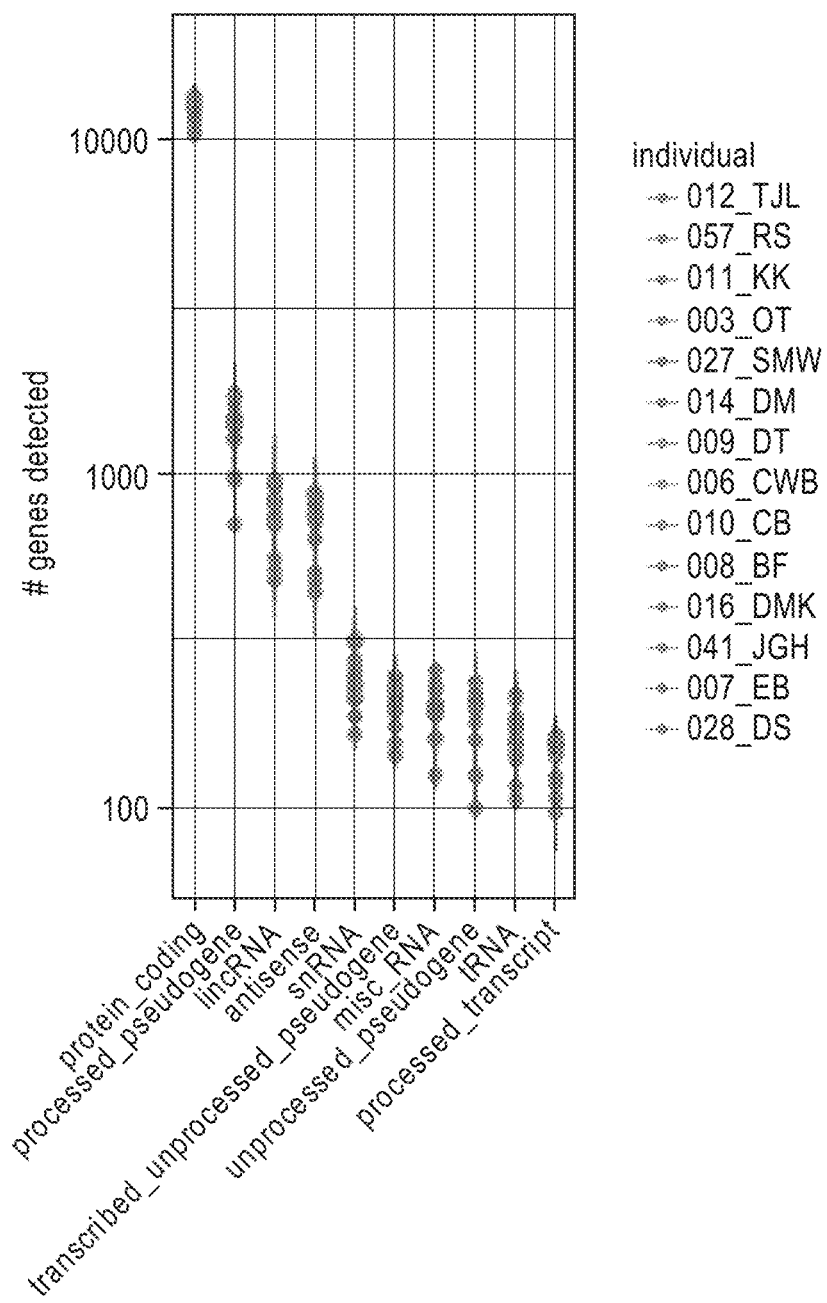
FIG. 2 is a chart showing the number of genes by biotype detected in samples from 14 patients.

The top panel of FIG. 1 shows the number of reads per million obtained for each RNA biotype in the 14 samples and the bottom panel shows the transcripts per million obtained for each RNA biotype in the 14 samples. In each group of bars, the left bar corresponds to the pre-treatment sample and the right bar corresponds to the post-treatment sample. FIG. 2 shows the number of genes by biotype detected in the 14 samples. In FIGS. 1 and 2, the term protein_coding corresponds to mRNA.

Figure 3:
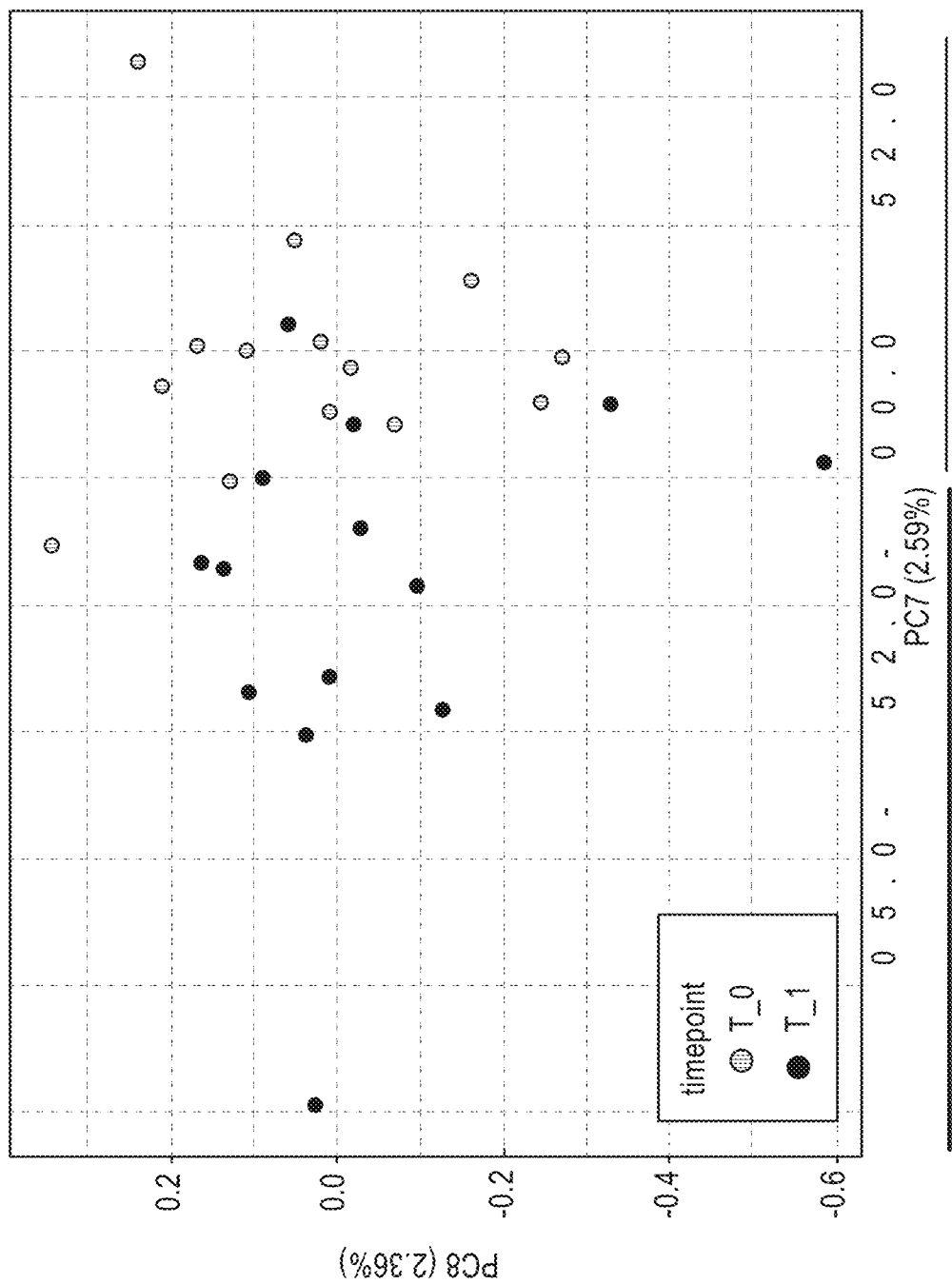
FIG. 3 is a chart showing the results of principle component analysis of all mRNA molecules in samples from 14 patients.
Figure 4A:
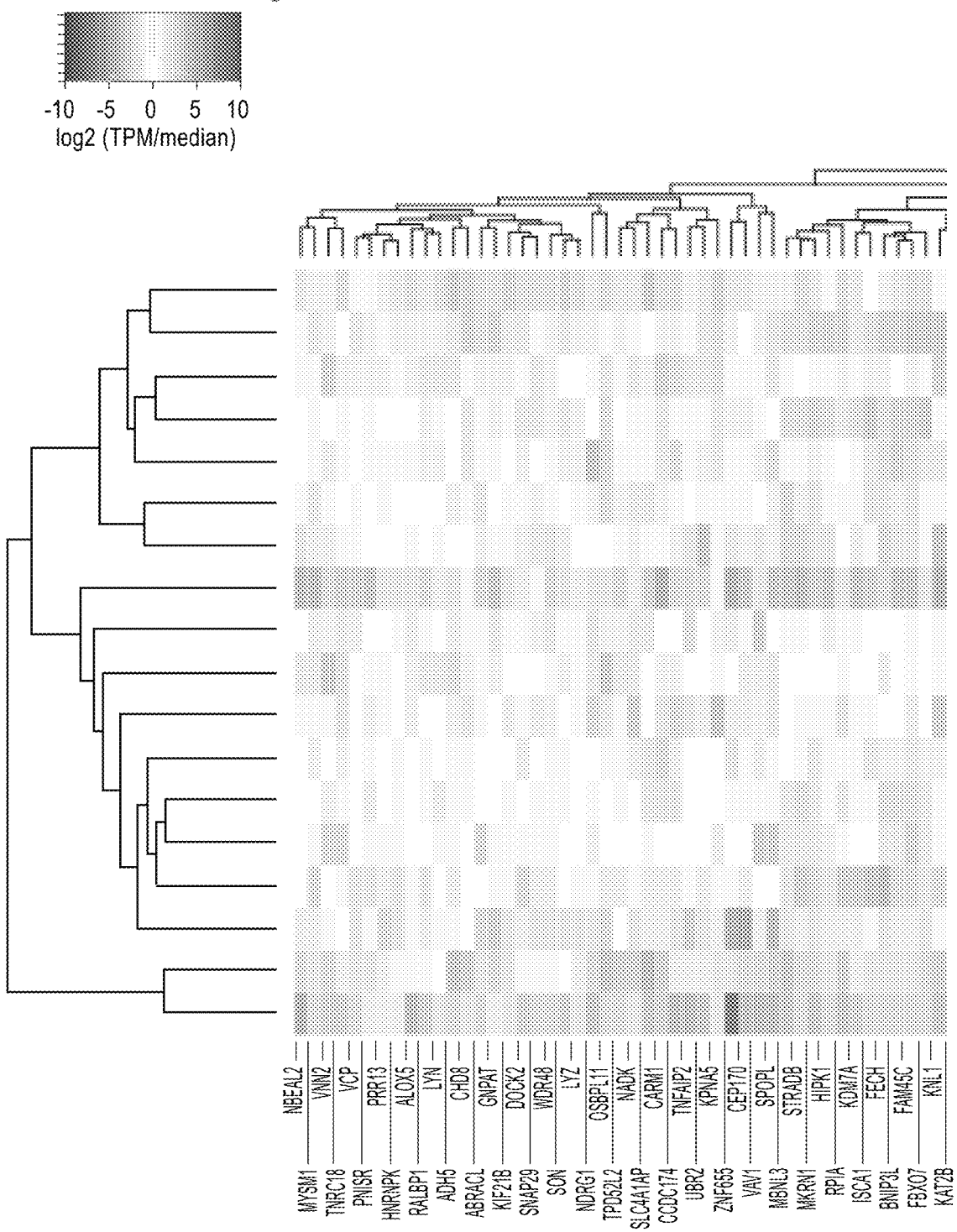
FIG. 4A, FIG. 4B, FIG. 4C, FIG. 4D, FIG. 4E, FIG. 4F, FIG. 4G and FIG. 4H are images of a heat map showing the results of differential expression analysis of healthy serum and plasma samples versus pre-treatment serum samples from patients with glioblastoma multiforme (GBM) comprising genes recited in Table 1 and Table 2.
Figure 4B:
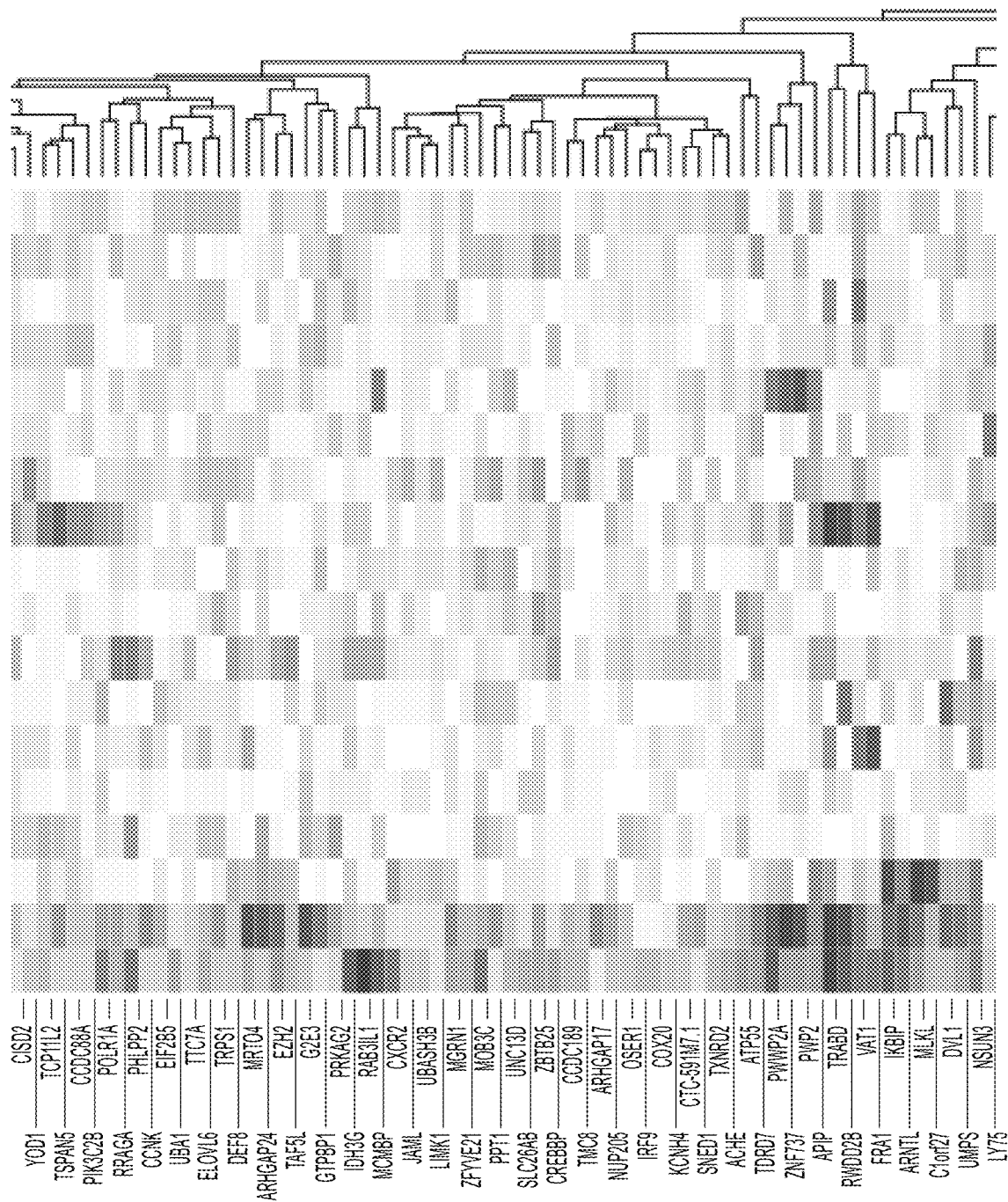
Figure 4C:
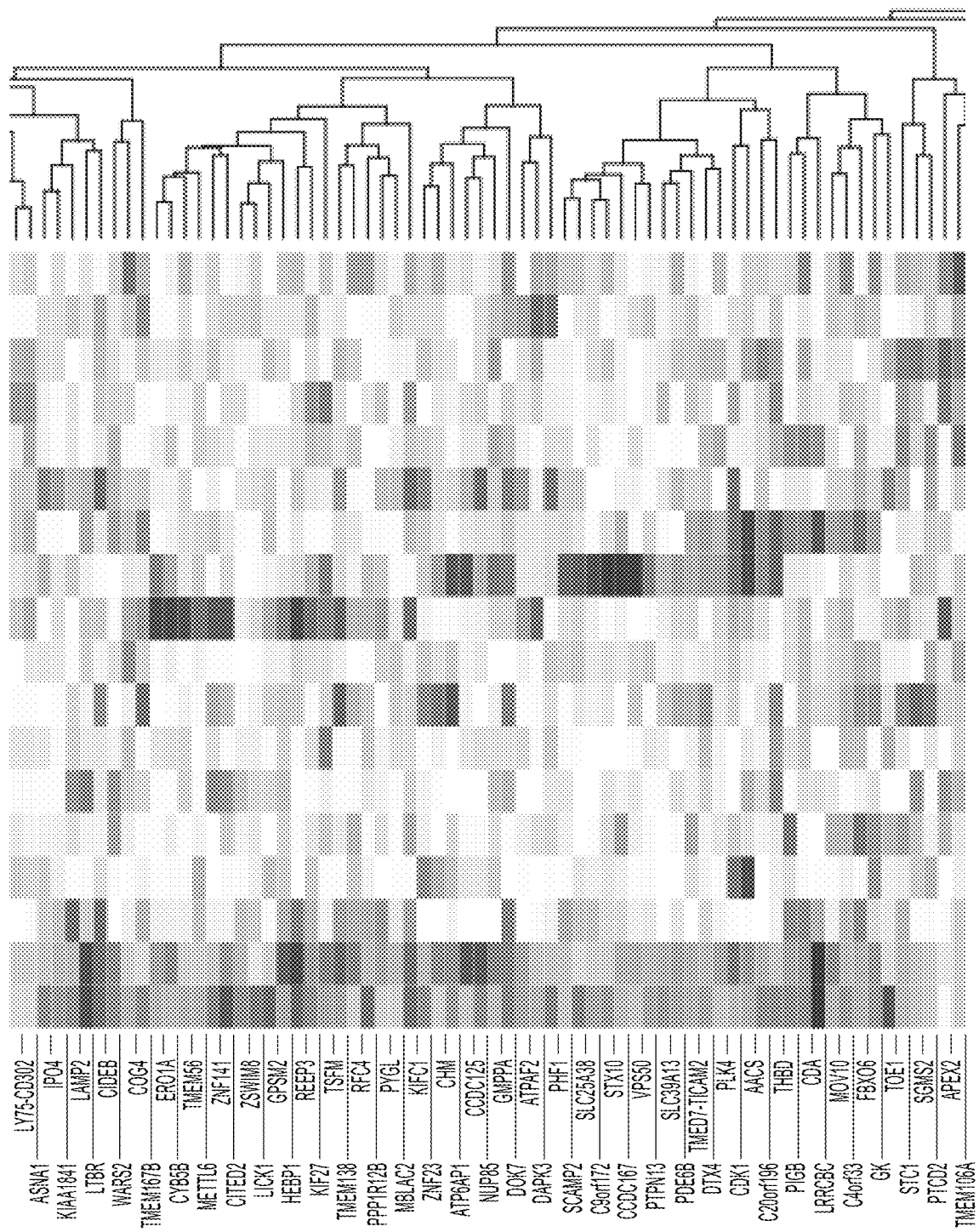
Figure 4D:
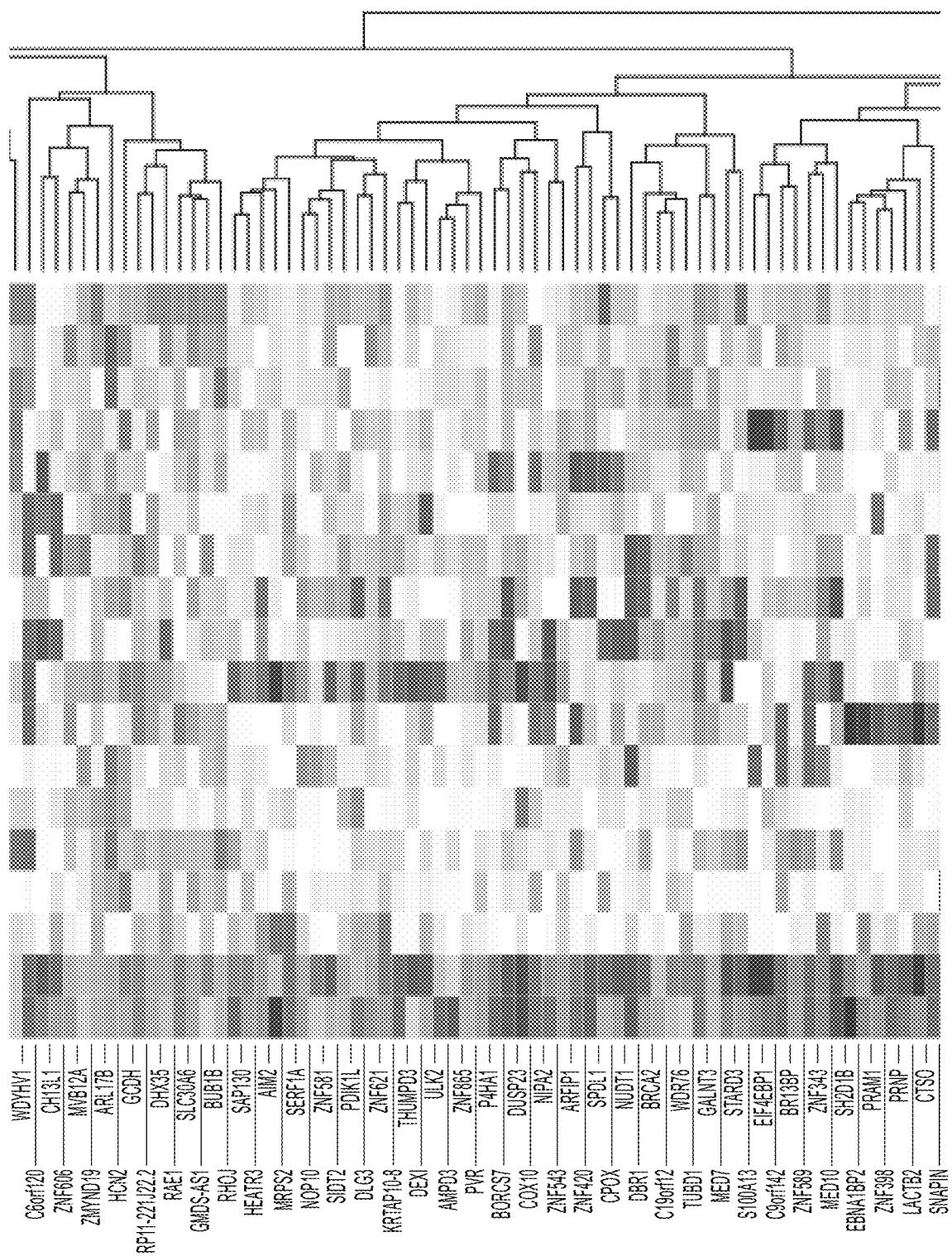
Figure 4E:
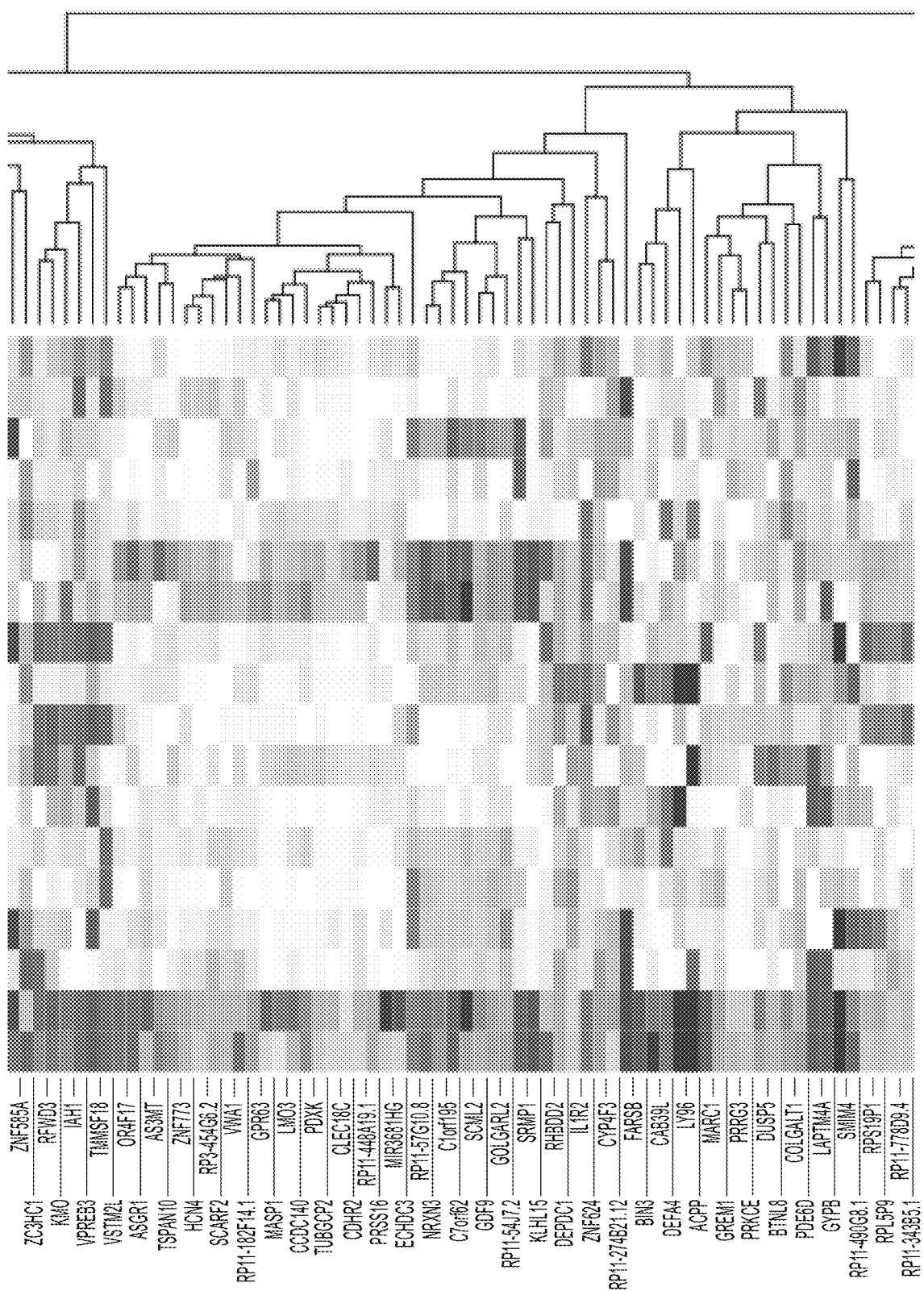
Figure 4F:
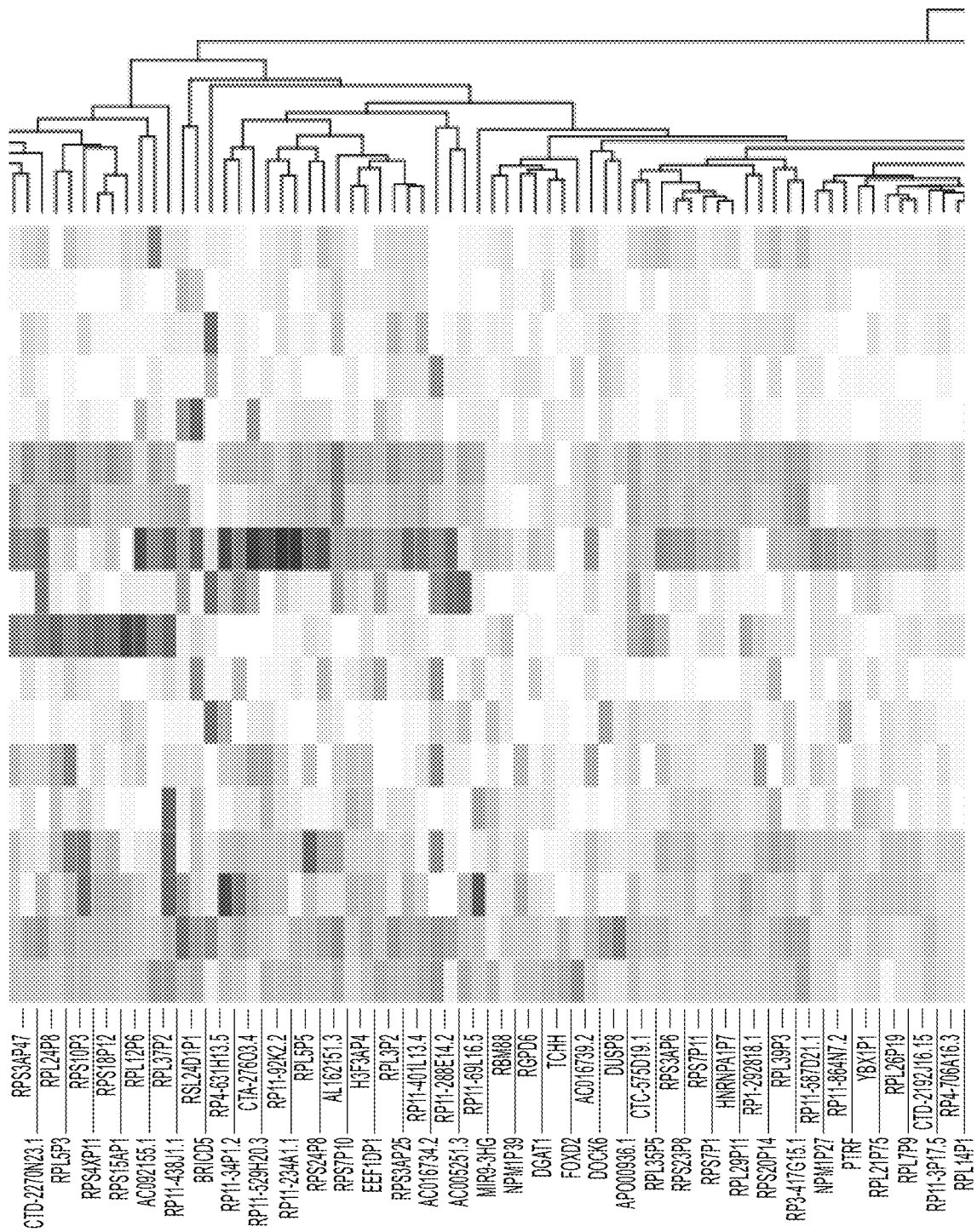
Figure 4G:
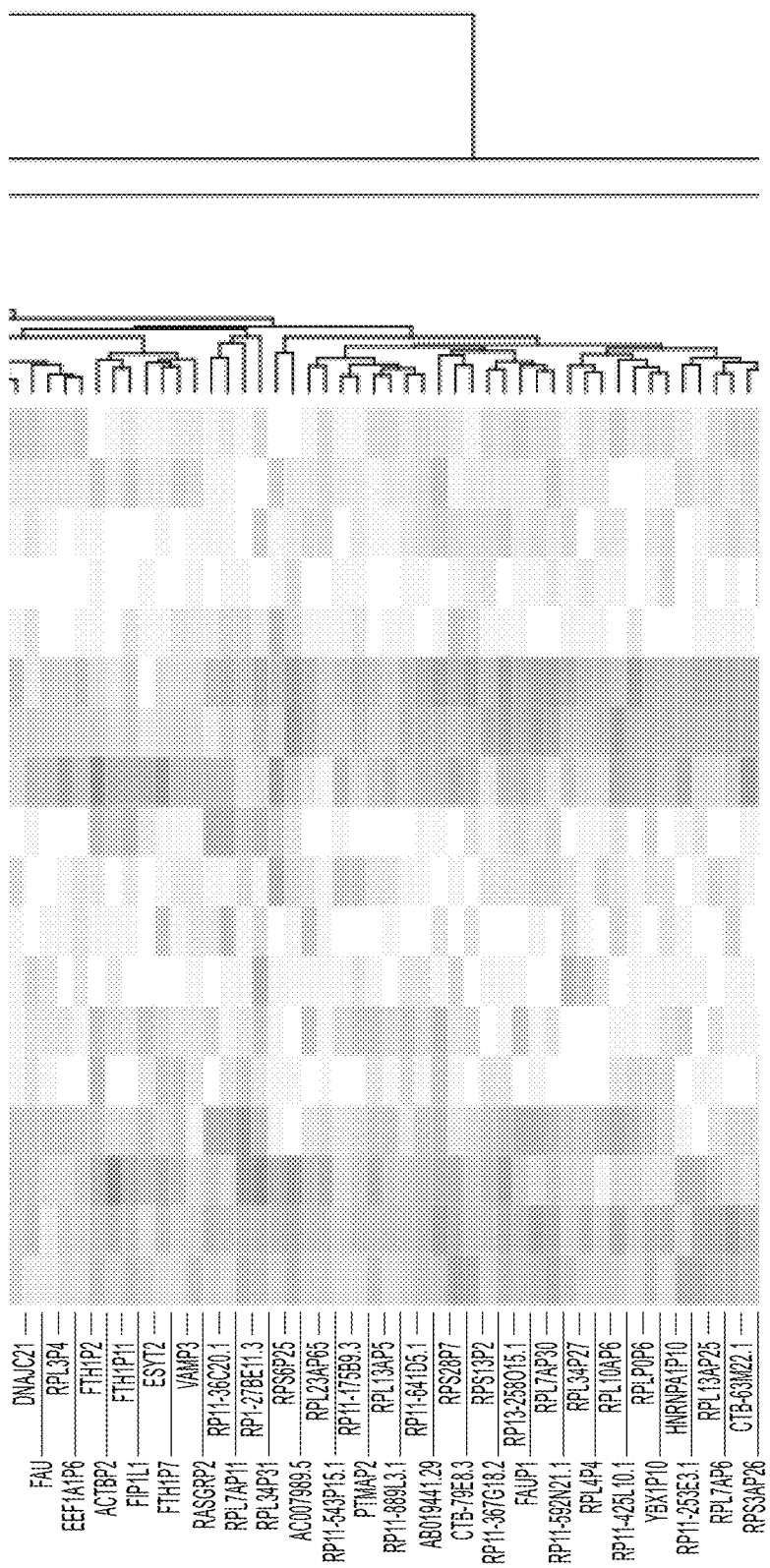
Figure 4H:
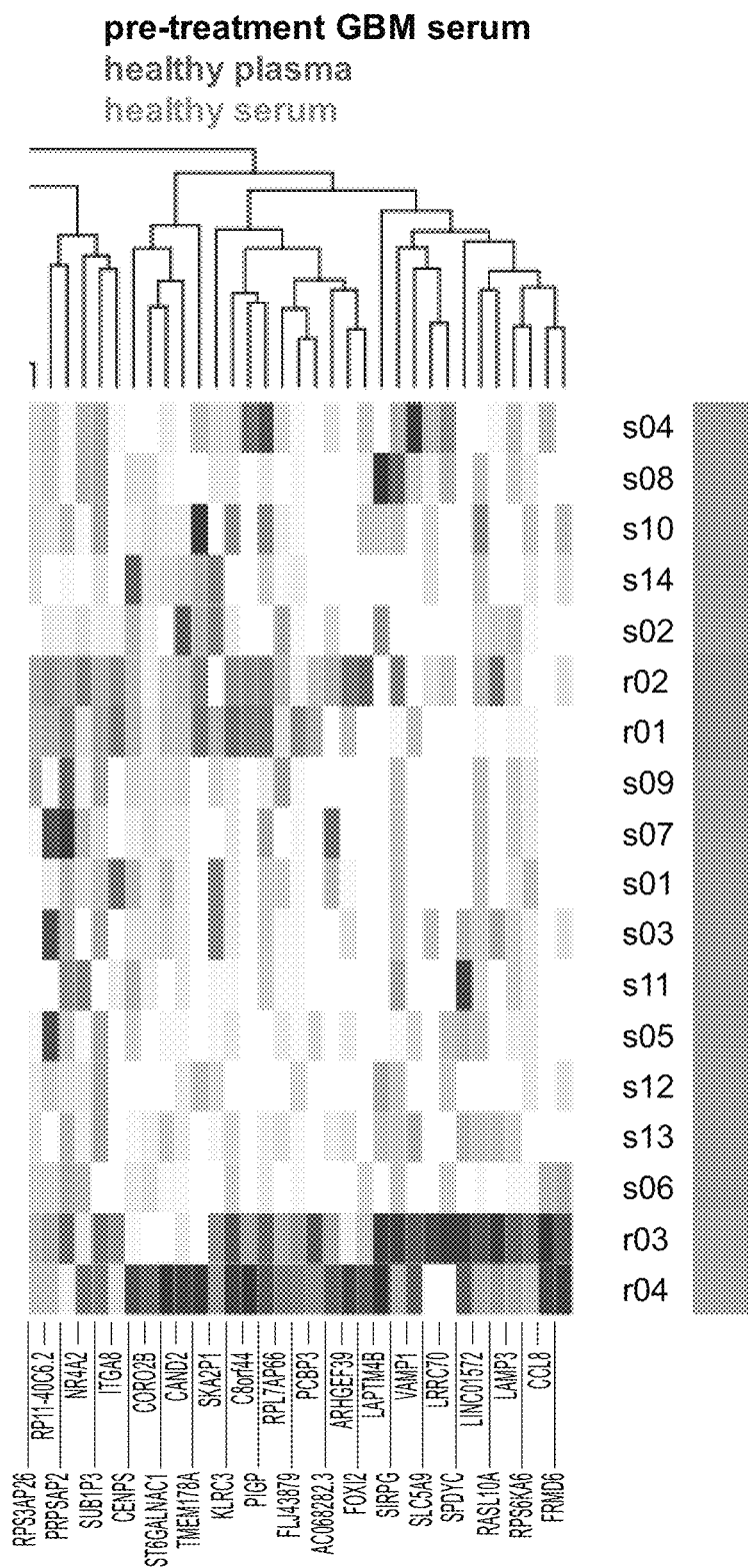

Principle component analysis was performed on read-counts of all protein coding (mRNA) genes. The analysis, shown in FIG. 3, displays a good separation between pre-treatment and post-treatment samples by PC7, with a 2.6% total variability. These results were encouraging as they suggested that there are a large number of differentially expressed genes that are driving the pre-vs-post treatment difference.

Differential expression analysis was then performed. First gene expression data from healthy plasma and serum samples was compared to the gene expression data from the pre-treatment samples to determine if particular genes are differentially expressed in GBM versus healthy patients. The heat map in FIGS. 4A-4H shows the results of this analysis and comprises genes recited in Table 1 and Table 2. In all, over 1000 genes were significantly differentially expressed in the pre-treatment GBM samples versus the healthy samples (p(adjusted)<0.05). Genes that were upregulated in pre-treatment GBM samples are shown in Table 1 and genes that were downregulated in pre-treatment GBM samples are shown in Table 2.

Figure 5:
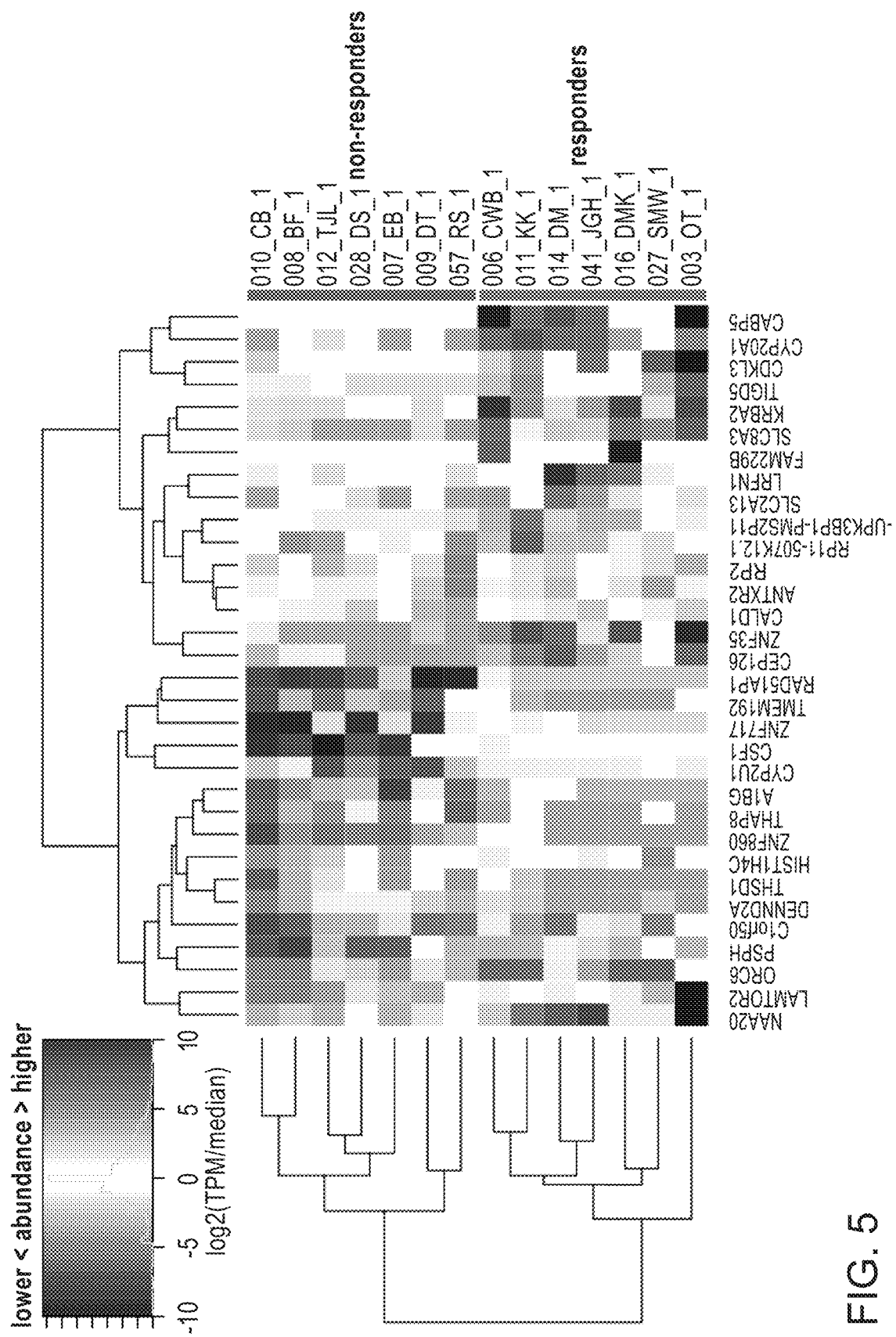
FIG. 5 is a heat map showing the results from differential expression analysis of pre-treatment serum samples from patients with GBM who did not respond to Dacomitinib versus pre-treatment serum samples from patients with GBM who responded to Dacomitinib

Differential expression analysis was also performed to determine if particular genes are differentially expressed in pre-treatment samples from patients who respond to Dacomitinib treatment compared to pre-treatment samples from patient who do not respond. Such differences could be used as a biomarker to determine if a patient will be a responder to Dacomitinib treatment. The results of this analysis is shown in FIG. 5. In all, 38 genes were significantly differentially expressed between responders and non-responders (p(adjusted)<0.05). These genes included a MAPK and MTOR activator. These 38 genes included 19 genes that were upregulated in patients that responded to Dacomitinib. These genes are shown in Table 3. The 38 genes also included 19 genes that were downregulated in patients that responded to Dacomitinib. These genes are shown in Table 4.

Figure 6:
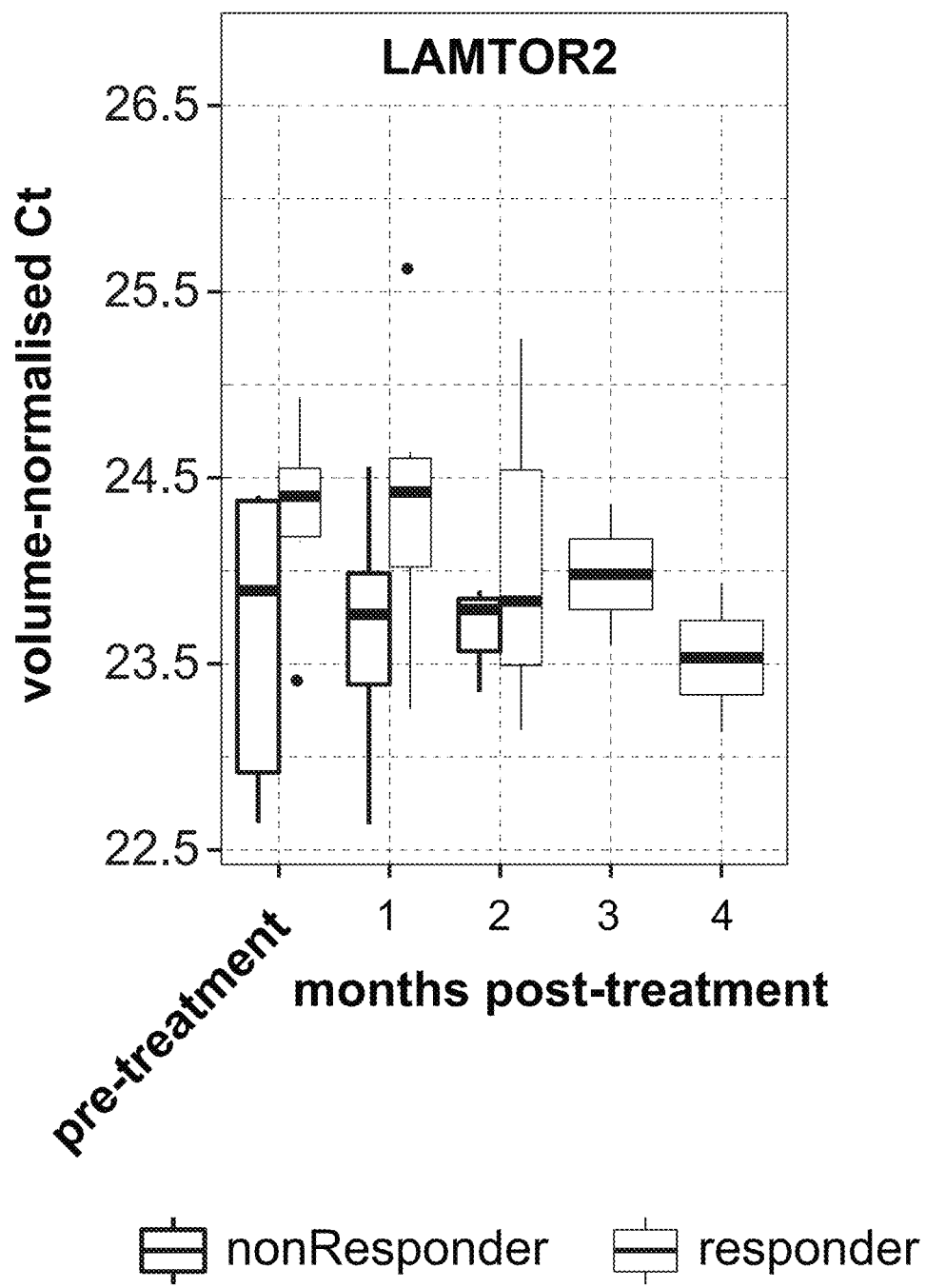
FIG. 6 is a chart showing the volume normalized cycle threshold (Ct) value of LAMTOR2 in pre-treatment and post-treatment (at months 1-4) patient samples of both patients who did not respond to Dacomitinib (red) vs those who responded to Dacomitinib (green).

The abundance of LAMTOR2, a gene involved in amino acid sensing and activation of mTORC1, was validated using quantitative PCR. FIG. 6 is a graph of the volume normalized cycle threshold value for LAMTOR2 in a variety of different samples, including pre-treatment and post-treatment time points in responders and non-responders. FIG. 6 shows, like the RNA seq data, that LAMTOR2 exhibits a higher abundance in serum exosomes of non-responders. Furthermore, the abundance of LAMTOR2 increases in responders over time.

Figure 7:
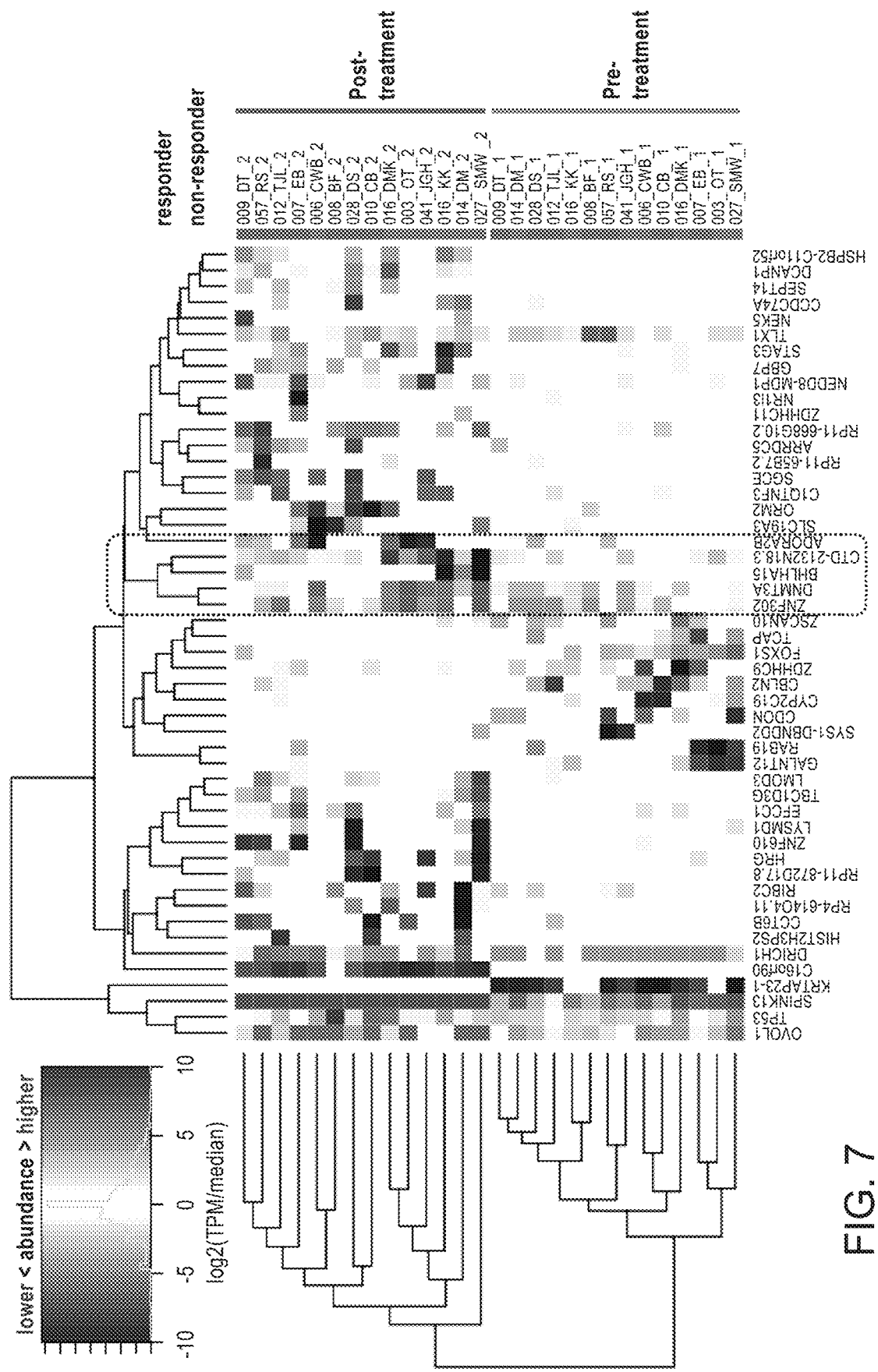
FIG. 7 is a heat map showing the results from differential expression analysis of pre-treatment serum samples versus post-treatment samples from patients with GBM of both patients who did not respond to Dacomitinib (orange) vs those who responded to Dacomitinib (gray).

Finally differential expression analysis was performed to determine if particular genes are differentially expressed in pre-treatment samples versus post-treatment samples, and whether there are differences in this differentially expression in responders and non-responders. The results of the analysis is shown in FIG. 7, with the post-treatment samples located on the top half of the heat map and the pre-treatment samples located on the bottom half of the heat map, and in Table 7. These genes included a known tumor suppressor (TP53), several transcriptional regulators and protein regulators. Furthermore, there were 5 genes that tracked with post-treatment response. These 5 genes included ZNF302, DNMT3A, BHLHA15, CTD-2132N18.3 and ADORA2B. These 5 genes showed higher levels of expression in post-treatment samples in patients who responded to the Dacomitinib treatment.

Figure 8:
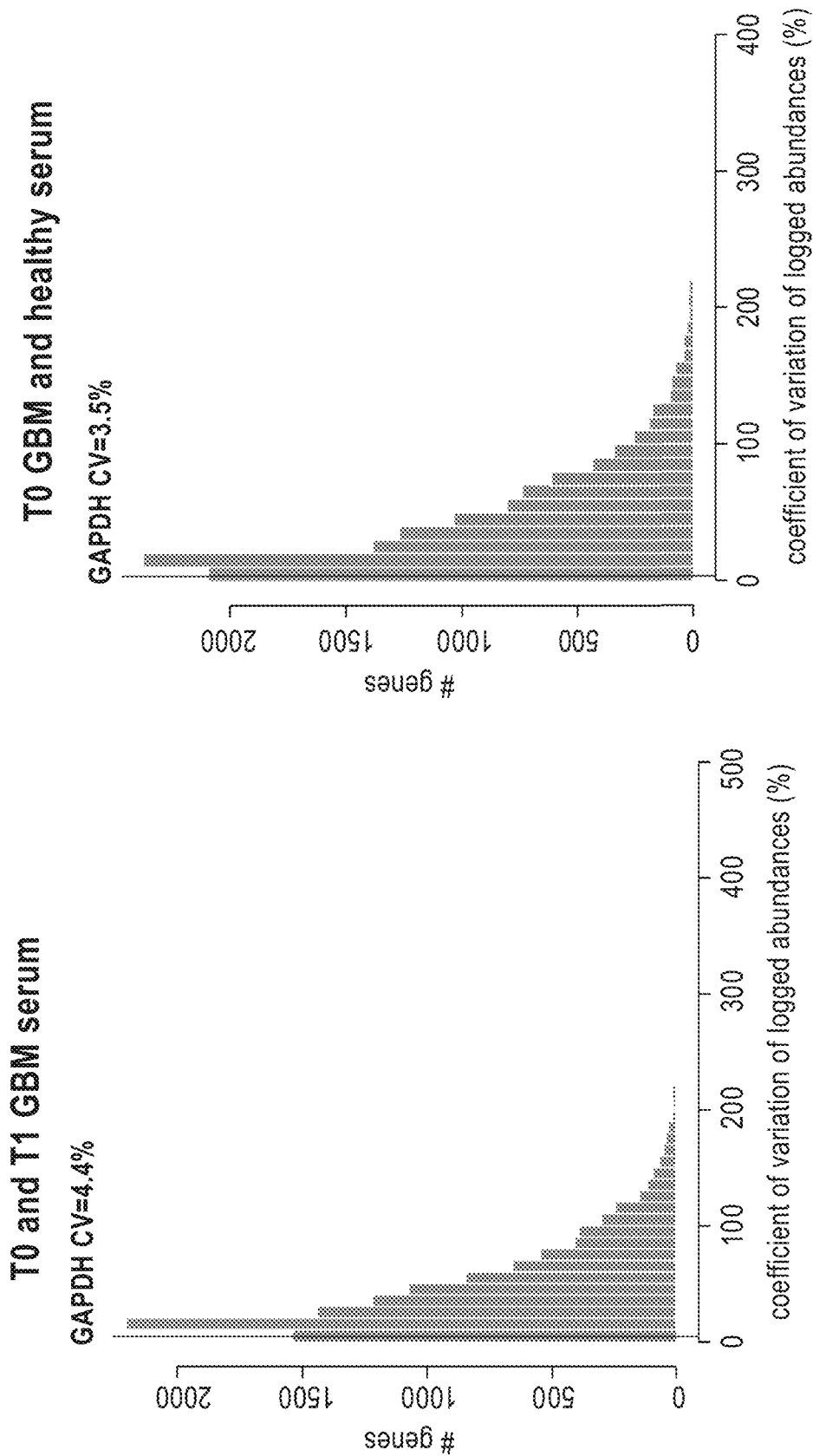
FIG. 8 is a plot showing the coefficient of variation across patients of the genes detected in the 14 pre-treatment and 14 post-treatment patient samples (left) as well as the 14 pre-treatment samples and 6 healthy serum samples (right).

For each of the genes detected in the patient samples, the coefficient of variation (CV) was calculated across the pre-treatment and post-treatment samples obtained from the 14 different patients. The results of this analysis are shown in the left panel of FIG. 8. The abundance of glyceraldehyde 3-phosphate dehydrogenase (GAPDH) was stable across the pre-treatment and post-treatment samples from the different patients and exhibited a low coefficient of variation of 4.4%. Additionally, for each of the genes detected in the pre-treatment samples from the GBM patients and the healthy serum samples, the coefficient of variation was calculated across the different samples. The results of this analysis are shown in the right panel of FIG. 8. The abundance of GAPDH was stable across the pre-treatment and the healthy samples and exhibited a low CV of 3.5%. Thus, GAPDH was identified as a useful reference gene that could be used to normalize the measured abundance of other biomarkers, allowing for qPCR-like thresholding.

In addition to GAPDH, several other genes were identified as exhibiting low CV values across the pre-treatment and post-treatment patient samples and across the pre-treatment and healthy samples. These genes could also be useful as reference genes to normalize the measured abundance of other biomarkers. A subset of these potential reference genes, and their corresponding CV values, are shown in Table 6. In total, 261 genes exhibited CV values equal to or less than 5%, making them useful as reference genes. These 261 genes are shown in Table 5

Figure 9:
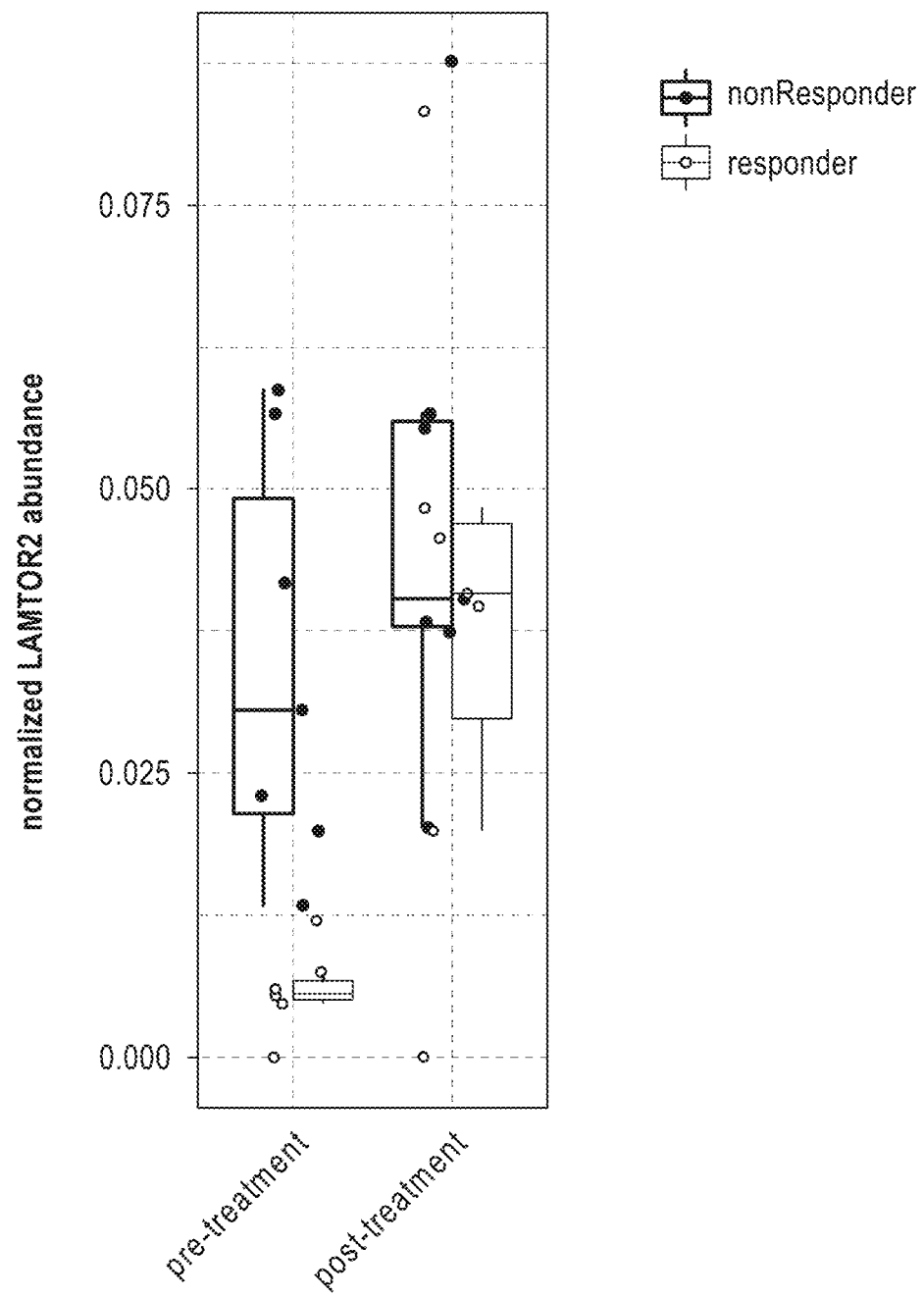
FIG. 9 is a box and whisker plot showing the normalized LAMTOR2 expression levels in the 14 patient samples, pre- and post-treatment.

To test the use of GAPDH as a reference gene, the expression level of LAMTOR2 was normalized using GAPDH. Normalization was achieved by dividing the expression level of LAMTOR2 in a particular sample by the expression level of GAPDH in the same sample to generate a normalized LAMTOR2 expression level. The results of this analysis for the pre-treatment samples and the post-treatment samples are shown in the box and whisker plot depicted in FIG. 9. For both sets of samples, the patients who did not respond to Dacomitinib treatment are on the left, and the patients that responded to Dacomitinib treatment are on the right. As shown in FIG. 9, the pre-treatment samples from patients who responded to Dacomitinib treatment exhibited a lower normalized LAMTOR2 expression level compared to the pre-treatment samples from patients who did not respond to treatment. In fact, one could predict that a patient would respond to Dacomitinib treatment with a positive predictive value of 100% and a sensitivity of 100% by determining if the patient's normalized LAMTOR2 expression level prior to treatment was less than 0.0125.

Figure 10:
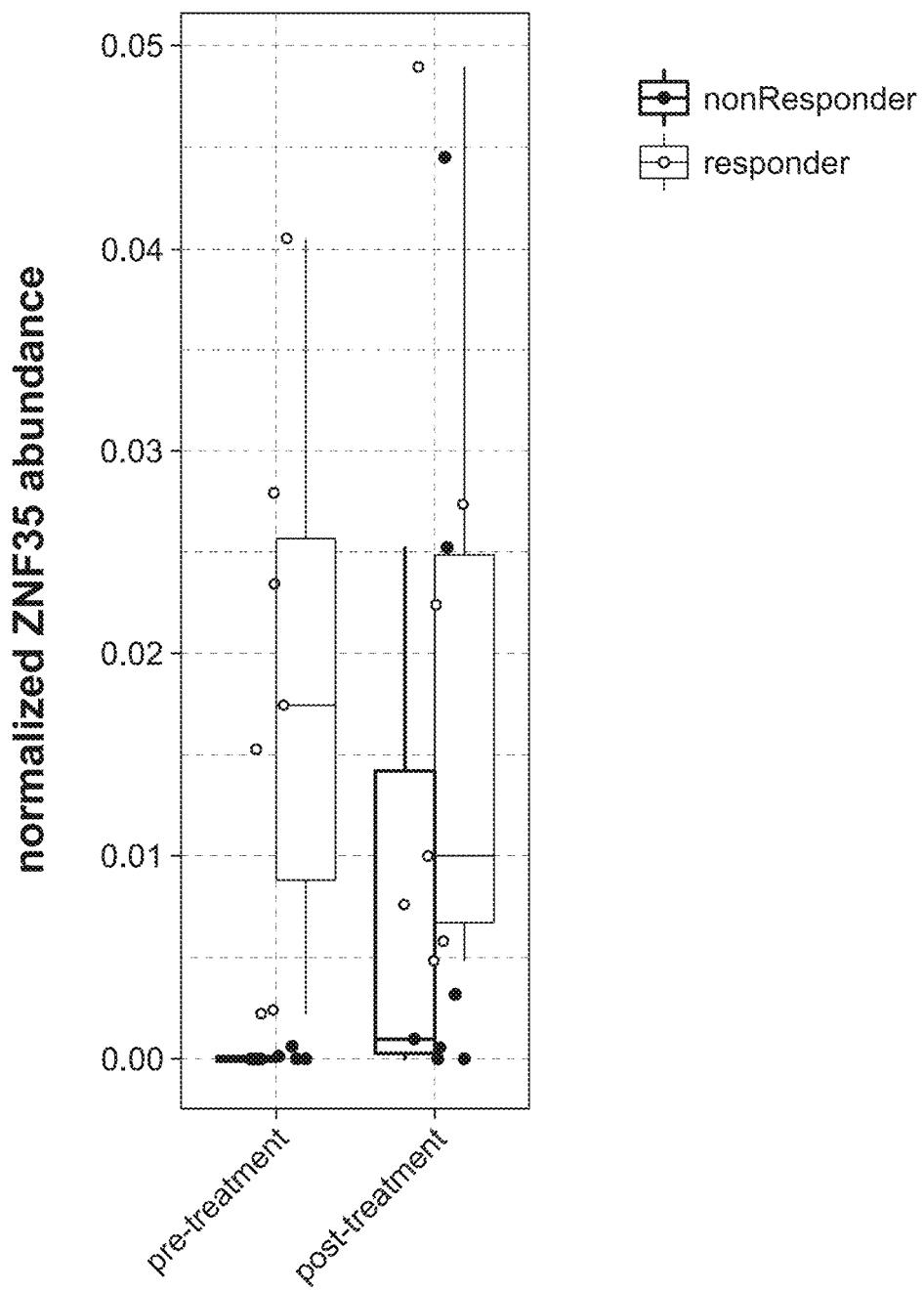
FIG. 10 is a box and whisker plot showing the normalized ZNF35 expression levels in the 14 patient samples, pre- and post-treatment.

A similar normalization analysis was performed for ZNF35. The normalized expression levels of ZNF35 in pre-treatment and post-treatment samples are shown in the box and whisker plots depicted in FIG. 10. For both sets of samples, the patients who did not respond to Dacomitinib treatment are on the left, and the patients that responded to Dacomitinib treatment are on the right. As shown in FIG. 10, the pre-treatment samples from patients who responded to Dacomitinib treatment exhibited a higher normalized ZNF35 expression level compared to the pre-treatment samples from patients who did not respond to treatment. In fact, one could predict that a patient would respond to Dacomitinib treatment with a positive predictive value of 100% and a sensitivity of 100% by determining if the patient's normalized ZNF35 expression prior to treatment was greater than 0.002. Furthermore, the post-treatment samples from patients who responded to Dacomitinib treatment exhibited a higher normalized expression ZNF35 expression level compared to the post-treatment samples from patients who did not respond. In fact, a patient could be identified as responding to treatment with a positive predictive value of 77.8% and a sensitivity of 100% by determining if the patient's normalized ZNF35 expression level after treatment was greater than 0.004.

Figure 11:
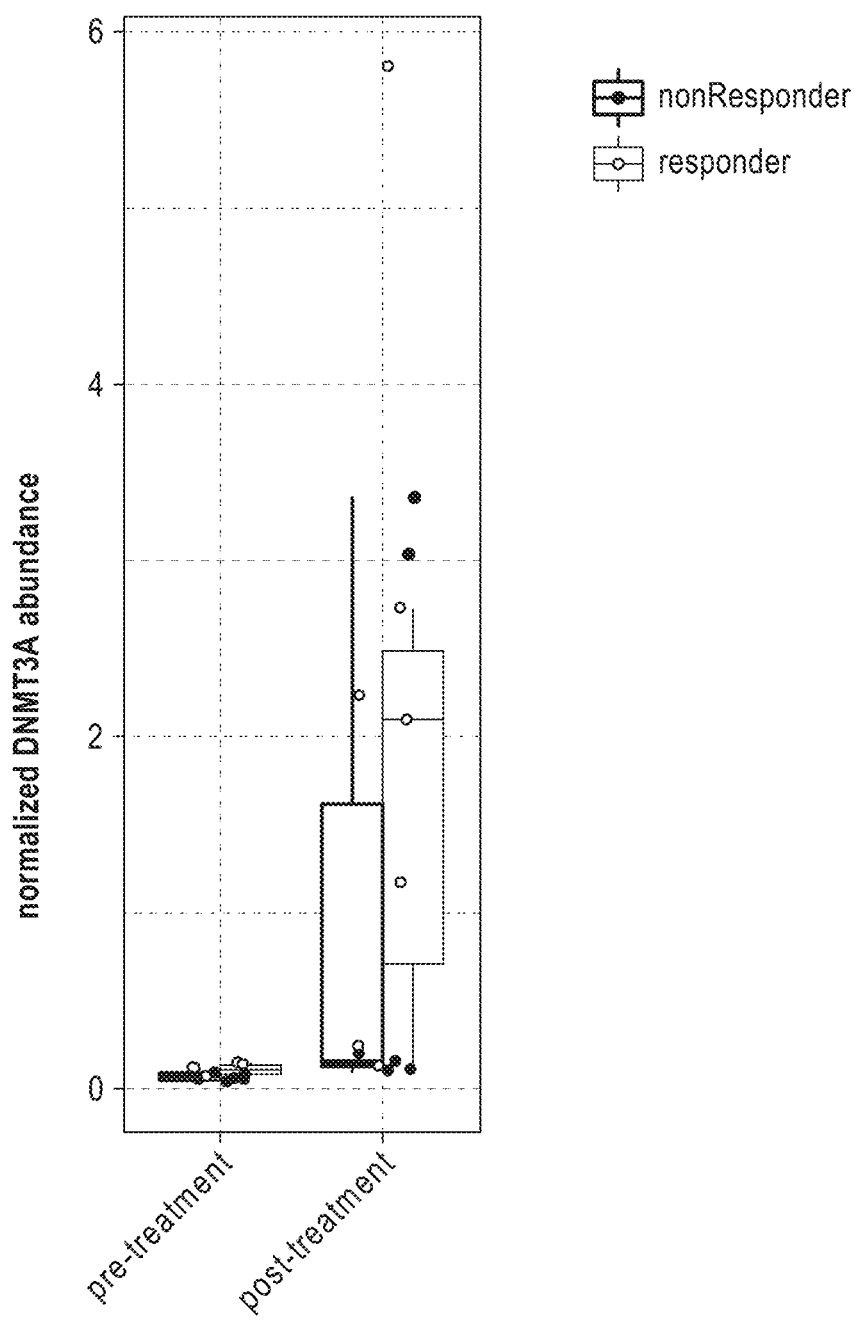
FIG. 11 is a box and whisker plot showing the normalized DNMT3A expression levels in the 14 patient samples, pre- and post-treatment.

A similar normalization analysis was performed for DNMT3A. The normalized expression levels of DNMT3A in pre-treatment and post-treatment samples are shown in the box and whisker plots depicted in FIG. 11. For both sets of samples, the patients who did not respond to Dacomitinib treatment are on the left, and the patients that responded to Dacomitinib treatment are on the right. As shown in FIG. 11, the post-treatment samples from patients who responded to Dacomitinib treatment exhibited a higher normalized DNMT3A expression level compared to the post-treatment samples from patients who did not respond. In fact, a patient could be identified as responding to treatment with a positive predictive value of 71.4% and a sensitivity of 71.4% by determining if the patient's normalized DNMT3A expression level after treatment was greater than 1.0.

Figure 12:
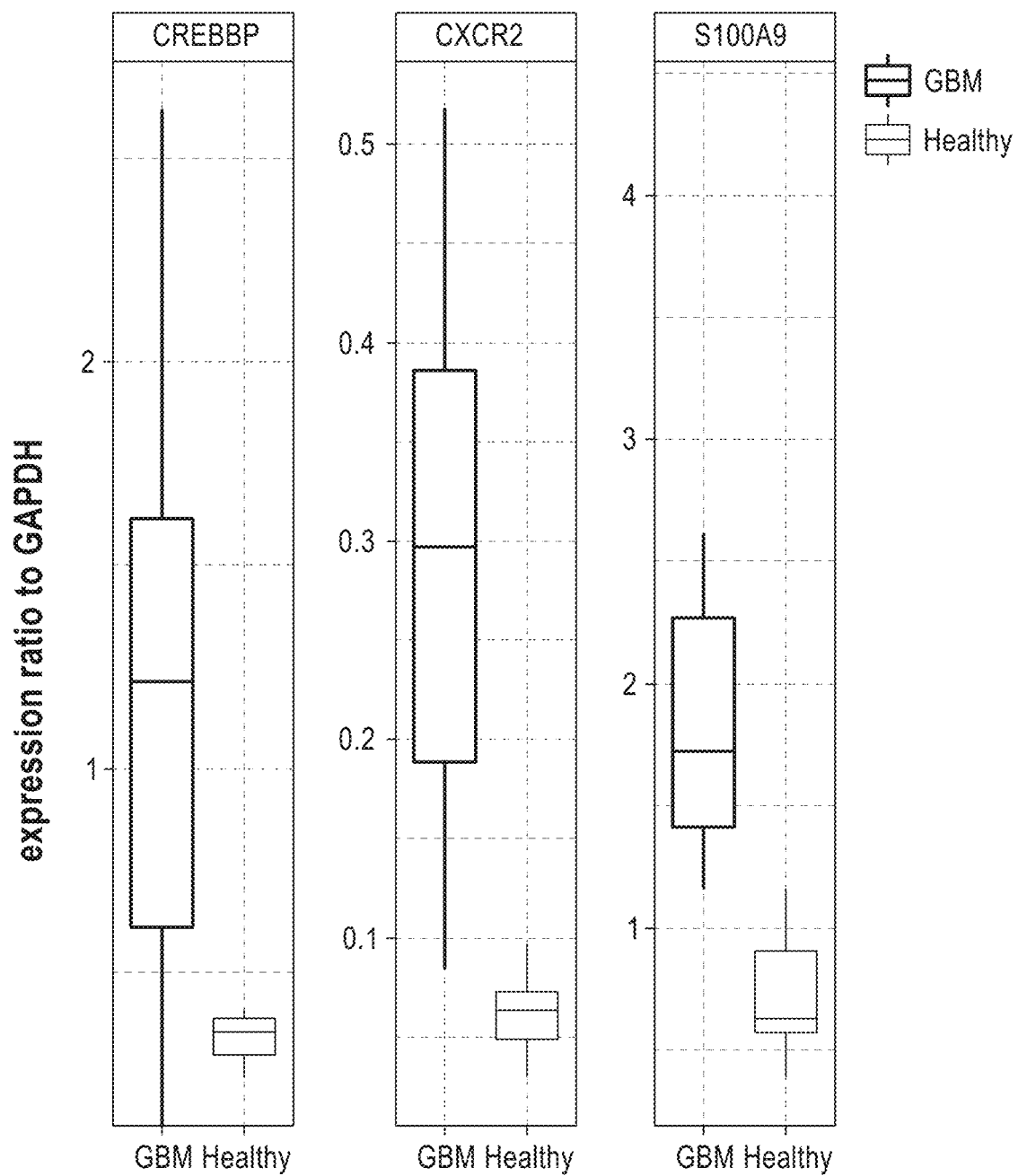
FIG. 12 is a series of is a box and whisker plot showing the normalized expression levels of CREBBP, CXCR2 and S100A9 in the 14 patient samples in pre-treatment GBM samples and healthy serum samples.

Normalized expression levels (using GAPDH as the reference gene) of particular genes in pre-treatment samples from GBM patients and samples from healthy patients were also compared. FIG. 12 is a series of box and whisker plots showing the normalized expression levels of CREBBP (left plot), CXCR2 (middle plot) and S100A9 (right plot) in GBM patients (box and whiskers on the left of each plot) and healthy serum (box and whiskers on the right of each plot). As FIG. 12 shows, the normalized expression levels of CREBBP, CXCR2 and S100A9 are greater in GBM patients than in healthy patients. In fact, one could predict that a patient had GBM with a positive predictive value of 100% and a sensitivity of 100% if the patient had a normalized CREBBP expression level greater than 0.42. One could also predict that a patient had GBM with a positive predictive value of 100% and a sensitivity of 92.9% if the patient had a normalized CXCR2 expression level greater than 0.1. Finally, one could predict that a patient had GBM with a positive predictive value of 100% and a sensitivity of 100% if the patient had a normalized S100A9 expression level greater than 1.16.

Tables

TABLE 1

Genes upregulated in glioblastoma multiforme

| Gene Name | GeneID |
| --- | --- |
| ABCA13 | ENSG00000179869.14 |
| ABRA | ENSG00000174429.3 |
| AC002398.9 | ENSG00000188223.9 |
| AC003090.1 | ENSG00000223561.6 |
| AC004112.4 | ENSG00000226851.1 |
| AC005062.2 | ENSG00000243004.5 |
| AC005481.5 | ENSG00000222012.1 |
| AC005559.3 | ENSG00000267036.2 |
| AC005740.5 | ENSG00000254099.1 |
| AC006014.7 | ENSG00000242073.2 |
| AC006070.12 | ENSG00000251439.1 |
| AC007192.4 | ENSG00000268173.2 |
| AC007386.2 | ENSG00000237638.1 |
| AC009133.23 | ENSG00000280893.1 |
| AC009166.5 | ENSG00000261238.1 |
| AC009237.8 | ENSG00000229689.3 |
| AC009299.2 | ENSG00000235724.8 |
| AC009501.4 | ENSG00000231609.5 |
| AC010547.9 | ENSG00000261611.5 |
| AC010642.2 | ENSG00000269794.1 |
| AC010731.3 | ENSG00000231653.1 |
| AC010761.8 | ENSG00000264577.1 |
| AC011933.2 | ENSG00000228007.1 |
| AC011999.1 | ENSG00000214070.3 |
| AC013439.4 | ENSG00000233996.1 |
| AC026471.6 | ENSG00000260740.2 |
| AC069363.1 | ENSG00000277089.4 |
| AC090498.1 | ENSG00000279483.1 |
| AC090616.2 | ENSG00000214708.4 |
| AC091153.4 | ENSG00000235085.3 |
| AC093495.4 | ENSG00000228242.6 |
| AC096558.1 | ENSG00000228655.6 |
| AC098872.3 | ENSG00000225884.2 |
| AC104024.1 | ENSG00000230709.1 |
| AC104389.1 | ENSG00000279346.1 |
| AC104667.3 | ENSG00000234949.2 |
| AC108004.3 | ENSG00000241525.4 |
| AC114271.2 | ENSG00000274425.1 |
| AC114730.3 | ENSG00000224272.2 |
| AC114730.8 | ENSG00000215692.2 |
| AC116366.5 | ENSG00000238160.1 |
| AC135048.13 | ENSG00000261487.1 |
| ACSL1 | ENSG00000151726.13 |
| ACSS3 | ENSG00000111058.7 |
| ACVR1B | ENSG00000135503.12 |
| ADAMTS16 | ENSG00000145536.15 |
| ADAMTSL2 | ENSG00000197859.9 |
| ADCY5 | ENSG00000173175.14 |
| ADGRA1-AS1 | ENSG00000256925.2 |
| ADRA2A | ENSG00000150594.6 |
| AF003625.3 | ENSG00000269993.1 |
| AF196970.3 | ENSG00000232828.1 |
| AGAP14P | ENSG00000279058.1 |
| AGAP7P | ENSG00000264204.2 |
| AGK | ENSG00000006530.15 |
| AIF1 | ENSG00000204472.12 |
| AKAIN1 | ENSG00000231824.3 |
| AKAP10 | ENSG00000108599.14 |
| AKR1C2 | ENSG00000151632.17 |
| AKR1C6P | ENSG00000151631.8 |
| AL022476.2 | ENSG00000230319.1 |
| AL365273.1 | ENSG00000282889.1 |
| AL513122.1 | ENSG00000283299.1 |
| AL513122.2 | ENSG00000283430.1 |
| AL589743.1 | ENSG00000279508.1 |
| ALDH5A1 | ENSG00000112294.12 |
| ALOX5AP | ENSG00000132965.9 |
| ALPL | ENSG00000162551.13 |
| AMBP | ENSG00000106927.11 |
| ANKHD1-EIF4EBP3 | ENSG00000254996.5 |
| ANKRD22 | ENSG00000152766.5 |
| ANKRD30A | ENSG00000148513.17 |
| ANKRD34A | ENSG00000272031.2 |
| ANTXRLP1 | ENSG00000263482.3 |
| AP000697.6 | ENSG00000224269.1 |
| AP000936.1 | ENSG00000234268.1 |
| AP001437.1 | ENSG00000273210.1 |
| AP001468.58 | ENSG00000228404.1 |
| AP001627.1 | ENSG00000225731.1 |
| APMAP | ENSG00000101474.11 |
| APOA4 | ENSG00000110244.6 |
| APOA5 | ENSG00000110243.11 |
| APOBEC3H | ENSG00000100298.15 |
| APOC3 | ENSG00000110245.11 |
| AQP9 | ENSG00000103569.9 |
| ARHGAP26 | ENSG00000145819.15 |
| ARHGEF17 | ENSG00000110237.3 |
| ARHGEF38 | ENSG00000236699.8 |
| ARL2-SNX15 | ENSG00000273003.1 |
| ARPC1A | ENSG00000241685.8 |
| ARPP21 | ENSG00000172995.16 |
| ARSDP1 | ENSG00000225117.1 |
| ARSE | ENSG00000157399.14 |
| ARX | ENSG00000004848.7 |
| ASAH2 | ENSG00000188611.14 |
| ASB8 | ENSG00000177981.10 |
| ASCL1 | ENSG00000139352.3 |
| ASGR1 | ENSG00000141505.11 |
| ASIC3 | ENSG00000213199.7 |
| ASIP | ENSG00000101440.9 |
| ASMT | ENSG00000196433.12 |
| ASNSP1 | ENSG00000248498.3 |
| ASS1P2 | ENSG00000223922.1 |
| ASTN1 | ENSG00000152092.15 |
| ASTN2 | ENSG00000148219.16 |
| ATP5E | ENSG00000124172.9 |
| ATP6V0D2 | ENSG00000147614.3 |
| ATP6V1F | ENSG00000128524.4 |
| ATP8A2 | ENSG00000132932.16 |
| BCL2L2-PABPN1 | ENSG00000258643.5 |
| BEGAIN | ENSG00000183092.16 |
| BEST1 | ENSG00000167995.15 |
| BEST3 | ENSG00000127325.18 |
| BGN | ENSG00000182492.15 |
| BHLHE23 | ENSG00000125533.5 |
| BICDL2 | ENSG00000162069.14 |
| BLACE | ENSG00000204960.6 |
| BLOC1S6 | ENSG00000104164.10 |
| BNIP3L | ENSG00000104765.15 |
| BORCS7-ASMT | ENSG00000270316.1 |
| BORCS8-MEF2B | ENSG00000064489.22 |
| BPGM | ENSG00000172331.11 |
| BRK1 | ENSG00000254999.3 |
| BSN | ENSG00000164061.4 |
| C15orf32 | ENSG00000183643.4 |
| C15orf38-AP3S2 | ENSG00000250021.7 |

TABLE 1-continued

Genes upregulated in glioblastoma multiforme

| Gene Name | GeneID |
| --- | --- |
| C15orf59 | ENSG00000205363.5 |
| C16orf95 | ENSG00000260456.6 |
| C17orf105 | ENSG00000231256.7 |
| C17orf74 | ENSG00000184560.7 |
| C1orf162 | ENSG00000143110.11 |
| C1orf195 | ENSG00000204464.7 |
| C1S | ENSG00000182326.14 |
| C20orf144 | ENSG00000149609.5 |
| C20orf166-AS1 | ENSG00000174403.15 |
| C3orf67 | ENSG00000163689.19 |
| C7orf62 | ENSG00000164645.2 |
| C7orf73 | ENSG00000243317.7 |
| C8orf44-SGK3 | ENSG00000270024.5 |
| CABP1 | ENSG00000157782.9 |
| CACNA1A | ENSG00000141837.19 |
| CACNG2 | ENSG00000166862.6 |
| CACNG4 | ENSG00000075461.5 |
| CACNG7 | ENSG00000105605.7 |
| CALM2 | ENSG00000143933.16 |
| CALM2P2 | ENSG00000229097.1 |
| CALN1 | ENSG00000183166.10 |
| CALY | ENSG00000130643.8 |
| CASC10 | ENSG00000204682.5 |
| CAV1 | ENSG00000105974.11 |
| CBLN2 | ENSG00000141668.9 |
| CCDC105 | ENSG00000160994.3 |
| CCDC140 | ENSG00000160081.2 |
| CCDC150 | ENSG00000144395.17 |
| CCDC189 | ENSG00000196118.11 |
| CCL16 | ENSG00000275152.4 |
| CCNDBP1 | ENSG00000166946.13 |
| CD300LG | ENSG00000161649.12 |
| CD68 | ENSG00000129226.13 |
| CDA | ENSG00000158825.5 |
| CDC42 | ENSG00000070831.15 |
| CDH18 | ENSG00000145526.11 |
| CDH19 | ENSG00000071991.8 |
| CDH2 | ENSG00000170558.8 |
| CDHR2 | ENSG00000074276.10 |
| CDK2 | ENSG00000123374.10 |
| CDON | ENSG00000064309.14 |
| CEBPD | ENSG00000221869.4 |
| CECR6 | ENSG00000183307.3 |
| CFAP20 | ENSG00000070761.7 |
| CFHR3 | ENSG00000116785.13 |
| CH17-264B6.3 | ENSG00000277125.1 |
| CH17-264B6.4 | ENSG00000273897.1 |
| CH17-38B12.4 | ENSG00000269475.2 |
| CHMP4C | ENSG00000164695.4 |
| CHST1 | ENSG00000175264.7 |
| CHST6 | ENSG00000183196.8 |
| CILP2 | ENSG00000160161.9 |
| CISD2 | ENSG00000145354.9 |
| CKLF | ENSG00000217555.12 |
| CKS1B | ENSG00000173207.12 |
| CLCA2 | ENSG00000137975.7 |
| CLCNKB | ENSG00000184908.17 |
| CLEC18B | ENSG00000140839.11 |
| CLEC18C | ENSG00000157335.20 |
| CLEC4E | ENSG00000166523.7 |
| CLIC6 | ENSG00000159212.12 |
| CLUL1 | ENSG00000079101.16 |
| CMB9-55A18.1 | ENSG00000269570.2 |
| CMTM2 | ENSG00000140932.9 |
| CNIH3 | ENSG00000143786.7 |
| CNOT4P1 | ENSG00000236704.1 |
| COL18A1 | ENSG00000182871.14 |
| COL27A1 | ENSG00000196739.14 |
| COL4A2-AS2 | ENSG00000224821.5 |
| COX5BP7 | ENSG00000226024.1 |
| CP | ENSG00000047457.13 |
| CPSF4L | ENSG00000187959.9 |
| CR1 | ENSG00000203710.10 |
| CRB3 | ENSG00000130545.15 |
| CREBBP | ENSG00000005339.14 |
| CRISP3 | ENSG00000096006.11 |
| CROCCP1 | ENSG00000225769.1 |
| CSDAP1 | ENSG00000261614.1 |
| CSF2RB | ENSG00000100368.13 |
| CSNK2A3 | ENSG00000254598.2 |
| CSPG4P10 | ENSG00000276710.4 |
| CSRP1 | ENSG00000159176.13 |
| CT62 | ENSG00000225362.8 |
| CTA-989H11.1 | ENSG00000273366.1 |
| CTA-992D9.11 | ENSG00000279440.1 |
| CTB-107G13.1 | ENSG00000234715.1 |
| CTB-31O20.2 | ENSG00000261526.2 |
| CTB-31O20.6 | ENSG00000267125.2 |
| CTB-60B18.22 | ENSG00000283251.1 |
| CTB-89H12.4 | ENSG00000230551.4 |
| CTBP1-AS | ENSG00000280927.1 |
| CTC-265F19.2 | ENSG00000267412.1 |
| CTC-327F10.1 | ENSG00000249518.1 |
| CTC-338M12.4 | ENSG00000233937.6 |
| CTC-338M12.7 | ENSG00000247049.2 |
| CTC-360G5.9 | ENSG00000269486.2 |
| CTC-400I9.2 | ENSG00000267081.1 |
| CTC-435M10.10 | ENSG00000268987.1 |
| CTC-484M2.1 | ENSG00000242858.1 |
| CTC-518B2.8 | ENSG00000269741.5 |
| CTC-573M9.1 | ENSG00000248634.1 |
| CTD-2006K23.1 | ENSG00000261222.2 |
| CTD-2017F17.2 | ENSG00000274383.1 |
| CTD-2023N9.1 | ENSG00000250961.1 |
| CTD-2036P10.5 | ENSG00000278769.1 |
| CTD-2147F2.1 | ENSG00000259485.1 |
| CTD-2201E18.5 | ENSG00000271788.1 |
| CTD-2281E23.1 | ENSG00000275427.1 |
| CTD-2329K10.1 | ENSG00000259563.1 |
| CTD-2501B8.1 | ENSG00000264813.6 |
| CTD-2541J13.2 | ENSG00000263424.1 |
| CTD-2544H17.2 | ENSG00000272139.1 |
| CTD-2583A14.8 | ENSG00000269867.1 |
| CTD-2619J13.19 | ENSG00000269473.1 |
| CTD-2619J13.8 | ENSG00000268230.5 |
| CTD-2651B20.2 | ENSG00000259338.1 |
| CTD-2653D5.1 | ENSG00000255438.2 |
| CTD-2653M23.3 | ENSG00000272103.1 |
| CTD-3064M3.4 | ENSG00000244998.1 |
| CTSS | ENSG00000163131.10 |
| CXCR1 | ENSG00000163464.7 |
| CXCR2 | ENSG00000180871.7 |
| CYSTM1 | ENSG00000120306.9 |
| DAAM2 | ENSG00000146122.16 |
| DCAF12 | ENSG00000198876.12 |
| DCAF6 | ENSG00000143164.15 |
| DCN | ENSG00000011465.16 |
| DCUN1D1 | ENSG00000043093.13 |
| DEFA4 | ENSG00000164821.4 |
| DENND4A | ENSG00000174485.15 |
| DISP2 | ENSG00000140323.5 |
| DKK2 | ENSG00000155011.8 |
| DLX6 | ENSG00000006377.10 |
| DMRT1 | ENSG00000137090.11 |
| DMRTA2 | ENSG00000142700.11 |
| DNAH2 | ENSG00000183914.14 |
| DNAH3 | ENSG00000158486.13 |
| DNASE1L2 | ENSG00000167968.12 |
| DOC2A | ENSG00000149927.17 |
| DOK3 | ENSG00000146094.13 |
| DOK7 | ENSG00000175920.15 |
| DPEP1 | ENSG00000015413.9 |
| DPM3 | ENSG00000179085.7 |
| DPYS | ENSG00000147647.12 |
| DPYSL5 | ENSG00000157851.16 |
| DUSP15 | ENSG00000149599.15 |
| DUSP8P3 | ENSG00000215097.3 |
| DUSP8P5 | ENSG00000235316.1 |
| ECEL1 | ENSG00000171551.11 |
| ECHDC3 | ENSG00000134463.14 |
| EDIL3 | ENSG00000164176.12 |
| EEF1A1P4 | ENSG00000245205.3 |

TABLE 1-continued

Genes upregulated in glioblastoma multiforme

| Gene Name | GeneID |
| --- | --- |
| EEF1A1P5 | ENSG00000196205.8 |
| EFNA2 | ENSG00000099617.3 |
| EGFLAM-AS2 | ENSG00000248572.5 |
| EGR3 | ENSG00000179388.8 |
| EGR4 | ENSG00000135625.7 |
| EHMT2 | ENSG00000204371.11 |
| EIF3C | ENSG00000184110.14 |
| EIF4E2 | ENSG00000135930.13 |
| EIF4EBP2 | ENSG00000148730.6 |
| EIF4H | ENSG00000106682.14 |
| ELANE | ENSG00000197561.6 |
| EMC6 | ENSG00000127774.6 |
| EMX1 | ENSG00000135638.13 |
| EMX2 | ENSG00000170370.11 |
| ENPEP | ENSG00000138792.9 |
| EPG5 | ENSG00000152223.12 |
| EPHA8 | ENSG00000070886.11 |
| ERN2 | ENSG00000134398.13 |
| ESPL1 | ENSG00000135476.11 |
| ESPNP | ENSG00000268869.5 |
| EVI2B | ENSG00000185862.6 |
| EXTL3 | ENSG00000012232.8 |
| EYA4 | ENSG00000112319.17 |
| FABP1 | ENSG00000163586.9 |
| FABP7P1 | ENSG00000226766.1 |
| FADS1 | ENSG00000149485.17 |
| FAM104A | ENSG00000133193.12 |
| FAM131C | ENSG00000185519.8 |
| FAM149A | ENSG00000109794.13 |
| FAM153C | ENSG00000204677.10 |
| FAM159B | ENSG00000145642.11 |
| FAM166B | ENSG00000215187.9 |
| FAM180B | ENSG00000196666.4 |
| FAM189A1 | ENSG00000104059.4 |
| FAM19A4 | ENSG00000163377.15 |
| FAM200B | ENSG00000237765.6 |
| FAM229A | ENSG00000225828.1 |
| FAM45BP | ENSG00000221930.6 |
| FAM46C | ENSG00000183508.4 |
| FAM71C | ENSG00000180219.1 |
| FAM71F1 | ENSG00000135248.15 |
| FAM86B2 | ENSG00000145002.12 |
| FAM9C | ENSG00000187268.11 |
| FAR2 | ENSG00000064763.10 |
| FAT2 | ENSG00000086570.12 |
| FBXO7 | ENSG00000100225.17 |
| FCER1G | ENSG00000158869.10 |
| FCGR2A | ENSG00000143226.13 |
| FCGR3B | ENSG00000162747.9 |
| FECH | ENSG00000066926.10 |
| FEV | ENSG00000163497.2 |
| FEZF2 | ENSG00000153266.12 |
| FGB | ENSG00000171564.11 |
| FGF8 | ENSG00000107831.12 |
| FGL2 | ENSG00000127951.6 |
| FIGN | ENSG00000182263.13 |
| FKTN | ENSG00000106692.13 |
| FLJ40288 | ENSG00000183470.9 |
| FLRT2 | ENSG00000185070.10 |
| FOXA1 | ENSG00000129514.5 |
| FOXI3 | ENSG00000214336.4 |
| FOXL2NB | ENSG00000206262.8 |
| FPR1 | ENSG00000171051.8 |
| FPR3 | ENSG00000187474.4 |
| FREM1 | ENSG00000164946.19 |
| FRG2 | ENSG00000205097.6 |
| FRG2B | ENSG00000225899.7 |
| FRG2C | ENSG00000172969.7 |
| FRMD8P1 | ENSG00000227942.1 |
| FRRS1 | ENSG00000156869.12 |
| FSTL4 | ENSG00000053108.16 |
| FTCD | ENSG00000160282.13 |
| FTL | ENSG00000087086.14 |
| FUT9 | ENSG00000172461.10 |
| FXYD5 | ENSG00000089327.14 |
| FZD5 | ENSG00000163251.3 |
| GABARAPL2 | ENSG00000034713.7 |
| GABBR2 | ENSG00000136928.6 |
| GABRA1 | ENSG00000022355.16 |
| GABRA2 | ENSG00000151834.15 |
| GABRA3 | ENSG00000011677.12 |
| GAL | ENSG00000069482.6 |
| GAL3ST2 | ENSG00000154252.11 |
| GALNTL6 | ENSG00000174473.15 |
| GATS | ENSG00000239521.7 |
| GBX1 | ENSG00000164900.4 |
| GBX2 | ENSG00000168505.6 |
| GCA | ENSG00000115271.10 |
| GDF6 | ENSG00000156466.9 |
| GDF9 | ENSG00000164404.8 |
| GDI2P1 | ENSG00000229165.1 |
| GFRA4 | ENSG00000125861.14 |
| GFRAL | ENSG00000187871.2 |
| GGACT | ENSG00000134864.10 |
| GJB4 | ENSG00000189433.5 |
| GJC1 | ENSG00000182963.9 |
| GJD3 | ENSG00000183153.6 |
| GLB1L | ENSG00000163521.15 |
| GLIS3 | ENSG00000107249.21 |
| GLT1D1 | ENSG00000151948.11 |
| GLT6D1 | ENSG00000204007.6 |
| GMNC | ENSG00000205835.8 |
| GNB2 | ENSG00000172354.9 |
| GOLGA2P9 | ENSG00000269332.5 |
| GOLGA6L2 | ENSG00000174450.11 |
| GPC5 | ENSG00000179399.14 |
| GPM6A | ENSG00000150625.16 |
| GPR142 | ENSG00000257008.6 |
| GPR146 | ENSG00000164849.9 |
| GPR149 | ENSG00000174948.5 |
| GPR17 | ENSG00000144230.16 |
| GPR37 | ENSG00000170775.2 |
| GPR37L1 | ENSG00000170075.8 |
| GPR63 | ENSG00000112218.8 |
| GPR75-ASB3 | ENSG00000270898.5 |
| GPR85 | ENSG00000164604.12 |
| GPRC5A | ENSG00000013588.6 |
| GRAMD1B | ENSG00000023171.15 |
| GRAMD4P2 | ENSG00000235992.1 |
| GRAMD4P3 | ENSG00000278301.1 |
| GREM1 | ENSG00000166923.10 |
| GRIA4 | ENSG00000152578.12 |
| CRN | ENSG00000030582.16 |
| GRTP1 | ENSG00000139835.13 |
| GSDMA | ENSG00000167914.11 |
| GSG1L | ENSG00000169181.12 |
| GSPT1 | ENSG00000103342.12 |
| GSX2 | ENSG00000180613.10 |
| GUCY2D | ENSG00000132518.6 |
| GYPC | ENSG00000136732.14 |
| HAPLN4 | ENSG00000187664.8 |
| HBBP1 | ENSG00000229988.1 |
| HCAR1 | ENSG00000196917.5 |
| HCN1 | ENSG00000164588.6 |
| HCN4 | ENSG00000138622.3 |
| HDGFL1 | ENSG00000112273.6 |
| HELZ2 | ENSG00000130589.16 |
| HEMGN | ENSG00000136929.12 |
| HERC2P5 | ENSG00000260644.6 |
| HERC2P8 | ENSG00000261599.5 |
| HIPK1 | ENSG00000163349.21 |
| HIPK1-AS1 | ENSG00000235527.6 |
| HIST1H2AI | ENSG00000196747.4 |
| HIST1H2AL | ENSG00000276903.1 |
| HIST1H2AM | ENSG00000278677.1 |
| HIST1H4J | ENSG00000197238.4 |
| HIST2H2AA4 | ENSG00000272196.2 |
| HIST3H3 | ENSG00000168148.3 |
| HLA-C | ENSG00000204525.15 |
| HLA-V | ENSG00000181126.13 |
| HMGA2 | ENSG00000149948.13 |
| HMGN2P28 | ENSG00000236086.4 |

TABLE 1-continued

Genes upregulated in glioblastoma multiforme

| Gene Name | GeneID |
|---|---|
| HNRNPA1P54 | ENSG00000236539.3 |
| HNRNPKP2 | ENSG00000227347.1 |
| HOXB13 | ENSG00000159184.7 |
| HOXC10 | ENSG00000180818.4 |
| HP09025 | ENSG00000267719.1 |
| HRC | ENSG00000130528.11 |
| HRH2 | ENSG00000113749.7 |
| HRK | ENSG00000135116.9 |
| HRNR | ENSG00000197915.5 |
| HS1BP3-IT1 | ENSG00000231948.2 |
| HS3ST4 | ENSG00000182601.6 |
| hsa-let-7a-3 | MI0000062 |
| hsa-mir-16-1 | MI0000070 |
| hsa-mir-4454 | MI0016800 |
| hsa-mir-6126 | MI0021260 |
| hsa-mir-6516 | MI0025513 |
| hsa-mir-6894 | MI0022741 |
| hsa-mir-7110 | MI0022961 |
| hsa-mir-7641-2 | MI0024976 |
| HSD11B1L | ENSG00000167733.13 |
| HSDL2 | ENSG00000119471.14 |
| HSPB2 | ENSG00000170276.5 |
| HSPB7 | ENSG00000173641.17 |
| HSPB9 | ENSG00000260325.1 |
| HTRA3 | ENSG00000170801.9 |
| ICAM5 | ENSG00000105376.4 |
| IFI30 | ENSG00000216490.3 |
| IFITM2 | ENSG00000185201.16 |
| IGF2 | ENSG00000167244.18 |
| IGSF10 | ENSG00000152580.8 |
| IGSF6 | ENSG00000140749.8 |
| IGSF9 | ENSG00000085552.16 |
| IKBIP | ENSG00000166130.14 |
| IL17D | ENSG00000172458.4 |
| IL17RD | ENSG00000144730.16 |
| IL1R2 | ENSG00000115590.13 |
| ILDR2 | ENSG00000143195.12 |
| IQCJ-SCHIP1 | ENSG00000283154.1 |
| IRX2 | ENSG00000170561.12 |
| IRX5 | ENSG00000176842.14 |
| ISCA1P1 | ENSG00000217416.4 |
| ITGAM | ENSG00000169896.16 |
| JAML | ENSG00000160593.17 |
| JAZF1 | ENSG00000153814.11 |
| KANSL1-AS1 | ENSG00000214401.4 |
| KANTR | ENSG00000232593.6 |
| KAT2B | ENSG00000114166.7 |
| KB-1208A12.3 | ENSG00000245970.2 |
| KCNC2 | ENSG00000166006.12 |
| KCNE1 | ENSG00000180509.11 |
| KCNE1B | ENSG00000276289.4 |
| KCNE3 | ENSG00000175538.10 |
| KCNJ15 | ENSG00000157551.17 |
| KCNJ6 | ENSG00000157542.9 |
| KCNJ9 | ENSG00000162728.4 |
| KCNK6 | ENSG00000099337.4 |
| KCNMA1-AS3 | ENSG00000225652.1 |
| KCNQ1DN | ENSG00000237941.2 |
| KCNQ1OT1 | ENSG00000269821.1 |
| KCTD1 | ENSG00000134504.12 |
| KCTD8 | ENSG00000183783.6 |
| KDELR3 | ENSG00000100196.10 |
| KHDC1 | ENSG00000135314.12 |
| KIAA0430 | ENSG00000166783.20 |
| KIAA1456 | ENSG00000250305.8 |
| KIAA1551 | ENSG00000174718.11 |
| KIAA1644 | ENSG00000138944.7 |
| KIF4B | ENSG00000226650.5 |
| KIF6 | ENSG00000164627.17 |
| KLF2 | ENSG00000127528.5 |
| KLF5 | ENSG00000102554.13 |
| KLHDC7A | ENSG00000179023.8 |
| KLHL33 | ENSG00000185271.7 |
| KLK10 | ENSG00000129451.11 |
| KREMEN1 | ENSG00000183762.12 |
| KRT15 | ENSG00000171346.14 |
| KRT18P57 | ENSG00000215867.4 |
| KRT223P | ENSG00000229028.2 |
| KRT23 | ENSG00000108244.16 |
| KRT8P46 | ENSG00000248971.2 |
| KRTAP10-8 | ENSG00000187766.1 |
| KRTAP16-1 | ENSG00000212657.1 |
| KRTAP23-1 | ENSG00000186980.6 |
| LAT | ENSG00000213658.10 |
| LDHAL6EP | ENSG00000270098.1 |
| LHX3 | ENSG00000107187.15 |
| LHX8 | ENSG00000162624.14 |
| LILRB3 | ENSG00000204577.11 |
| LINC00273 | ENSG00000256642.1 |
| LINC00383 | ENSG00000237534.1 |
| LINC00461 | ENSG00000245526.9 |
| LINC00479 | ENSG00000236384.7 |
| LINC00482 | ENSG00000185168.5 |
| LINC00562 | ENSG00000260388.2 |
| LINC00658 | ENSG00000226995.7 |
| LINC00683 | ENSG00000266256.1 |
| LINC00887 | ENSG00000214145.6 |
| LINC00907 | ENSG00000267586.6 |
| LINC00940 | ENSG00000235049.1 |
| LINC00976 | ENSG00000281657.2 |
| LINC01063 | ENSG00000232065.1 |
| LINC01091 | ENSG00000249464.5 |
| LINC01097 | ENSG00000281202.2 |
| LINC01104 | ENSG00000232084.5 |
| LINC01133 | ENSG00000224259.6 |
| LINC01185 | ENSG00000228414.6 |
| LINC01197 | ENSG00000248441.6 |
| LINC01287 | ENSG00000234722.3 |
| LINC01289 | ENSG00000253734.1 |
| LINC01342 | ENSG00000223823.1 |
| LINC01359 | ENSG00000226891.7 |
| LINC01410 | ENSG00000238113.6 |
| LINC01415 | ENSG00000267325.1 |
| LINC01422 | ENSG00000223704.1 |
| LINC01444 | ENSG00000264301.1 |
| LINC01465 | ENSG00000221949.5 |
| LINC01484 | ENSG00000253686.1 |
| LINC01487 | ENSG00000241336.1 |
| LINC01501 | ENSG00000229613.1 |
| LINC01556 | ENSG00000204709.4 |
| LINC01586 | ENSG00000249487.6 |
| LINC01624 | ENSG00000227508.6 |
| LINGO1 | ENSG00000169783.12 |
| LITAF | ENSG00000189067.12 |
| LL22NC03-123E1.5 | ENSG00000234726.1 |
| LLNLF-173C4.1 | ENSG00000282051.1 |
| LMO3 | ENSG00000048540.14 |
| LRFN4 | ENSG00000173621.8 |
| LRRC29 | ENSG00000125122.15 |
| LRRC37A | ENSG00000176681.14 |
| LRRC37A7P | ENSG00000265158.1 |
| LRRK2 | ENSG00000188906.14 |
| LTBP2 | ENSG00000119681.11 |
| LTC4S | ENSG00000213316.9 |
| LTF | ENSG00000012223.12 |
| LY6H | ENSG00000176956.12 |
| LYST | ENSG00000143669.13 |
| LYVE1 | ENSG00000133800.8 |
| LYZ | ENSG00000090382.6 |
| MAB21L1 | ENSG00000180660.7 |
| MAMDC2 | ENSG00000165072.9 |
| MAMDC4 | ENSG00000177943.13 |
| MAMSTR | ENSG00000176909.11 |
| MAP3K15 | ENSG00000180815.14 |
| MAP7D2 | ENSG00000184368.15 |
| MARCH4 | ENSG00000144583.4 |
| MARCH8 | ENSG00000165406.15 |
| MASP1 | ENSG00000127241.16 |
| MATN3 | ENSG00000132031.12 |
| MBNL3 | ENSG00000076770.14 |
| MBOAT1 | ENSG00000172197.10 |
| MBOAT2 | ENSG00000143797.11 |

TABLE 1-continued

Genes upregulated in glioblastoma multiforme

| Gene Name | GeneID |
| --- | --- |
| MC5R | ENSG00000176136.5 |
| MDFI | ENSG00000112559.13 |
| MDGA1 | ENSG00000112139.14 |
| MEF2A | ENSG00000068305.17 |
| MEFV | ENSG00000103313.12 |
| MEGF9 | ENSG00000106780.8 |
| MEIS1-AS3 | ENSG00000226819.1 |
| MEIS2 | ENSG00000134138.19 |
| MEIS3 | ENSG00000105419.17 |
| MEX3D | ENSG00000181588.16 |
| MFSD10 | ENSG00000109736.14 |
| MGAM | ENSG00000257335.8 |
| MIR1-1HG | ENSG00000174407.12 |
| MIR124-2HG | ENSG00000254377.5 |
| MIR219A2 | ENSG00000207955.4 |
| MIR6820 | ENSG00000279010.2 |
| MKLN1-AS | ENSG00000236753.5 |
| MKRN1 | ENSG00000133606.10 |
| MKRN9P | ENSG00000258128.2 |
| MME | ENSG00000196549.10 |
| MMP25 | ENSG00000008516.16 |
| MMP8 | ENSG00000118113.11 |
| MNX1-AS1 | ENSG00000243479.3 |
| MPPE1P1 | ENSG00000258990.2 |
| MS4A6A | ENSG00000110077.14 |
| MSLN | ENSG00000102854.15 |
| MSRB1 | ENSG00000198736.11 |
| MT-ATP6 | ENSG00000198899.2 |
| MT-CO1 | ENSG00000198804.2 |
| MT-CO2 | ENSG00000198712.1 |
| MT-CO3 | ENSG00000198938.2 |
| MT-CYB | ENSG00000198727.2 |
| MT-ND1 | ENSG00000198888.2 |
| MT-ND2 | ENSG00000198763.3 |
| MT-ND4 | ENSG00000198886.2 |
| MT-ND5 | ENSG00000198786.2 |
| MT-TC | ENSG00000210140.1 |
| MT-TD | ENSG00000210154.1 |
| MT-TE | ENSG00000210194.1 |
| MT-TF | ENSG00000210049.1 |
| MT-TG | ENSG00000210164.1 |
| MT-TH | ENSG00000210176.1 |
| MT-TI | ENSG00000210100.1 |
| MT-TK | ENSG00000210156.1 |
| MT-TL1 | ENSG00000209082.1 |
| MT-TL2 | ENSG00000210191.1 |
| MT-TM | ENSG00000210112.1 |
| MT-TN | ENSG00000210135.1 |
| MT-TP | ENSG00000210196.2 |
| MT-TQ | ENSG00000210107.1 |
| MT-TR | ENSG00000210174.1 |
| MT-TS1 | ENSG00000210151.2 |
| MT-TS2 | ENSG00000210184.1 |
| MT-TT | ENSG00000210195.2 |
| MT-TV | ENSG00000210077.1 |
| MT-TW | ENSG00000210117.1 |
| MT-TY | ENSG00000210144.1 |
| MTATP6P1 | ENSG00000248527.1 |
| MTCO1P18 | ENSG00000237910.1 |
| MTCO1P7 | ENSG00000236211.1 |
| MTCO3P12 | ENSG00000198744.5 |
| MTCP1 | ENSG00000214827.9 |
| MTCYBP29 | ENSG00000224880.1 |
| MTND2P28 | ENSG00000225630.1 |
| MTRNR2L5 | ENSG00000249860.3 |
| MTTP | ENSG00000138823.13 |
| MUC12 | ENSG00000205277.9 |
| MUM1 | ENSG00000160953.15 |
| MXD1 | ENSG00000059728.10 |
| MXD3 | ENSG00000213347.10 |
| MXI1 | ENSG00000119950.20 |
| MYD88 | ENSG00000172936.12 |
| MYO15A | ENSG00000091536.16 |
| MYOD1 | ENSG00000129152.3 |
| NAIP | ENSG00000249437.7 |
| NANOGP1 | ENSG00000176654.12 |
| NAP1L1P3 | ENSG00000213371.4 |
| NCF2 | ENSG00000116701.14 |
| NDEL1 | ENSG00000166579.15 |
| NDRG1 | ENSG00000104419.14 |
| NDUFA6 | ENSG00000184983.9 |
| NDUFB4P11 | ENSG00000259374.2 |
| NECAB1 | ENSG00000123119.11 |
| NEDD9 | ENSG00000111859.16 |
| NEGR1 | ENSG00000172260.14 |
| NEURL1-AS1 | ENSG00000235470.5 |
| NEUROD4 | ENSG00000123307.3 |
| NHLH2 | ENSG00000177551.5 |
| NIT1 | ENSG00000158793.13 |
| NKX2-5 | ENSG00000183072.9 |
| NLGN3 | ENSG00000196338.12 |
| nm-tRNA-Tyr-GTA-chr14-8 | nm-tRNA-Tyr-GTA-chr14-8 |
| nmt-tRNA-Gln-TTG-9-1 | nmt-tRNA-Gln-TTG-9-1 |
| NOV | ENSG00000136999.4 |
| NOVA1 | ENSG00000139910.19 |
| NPAP1P4 | ENSG00000236521.1 |
| NPTX2 | ENSG00000106236.3 |
| NR2E3 | ENSG00000278570.4 |
| NRBF2 | ENSG00000148572.15 |
| NRXN1 | ENSG00000179915.22 |
| NRXN3 | ENSG00000021645.18 |
| NTN4 | ENSG00000074527.11 |
| NUPR2 | ENSG00000185290.3 |
| NUTM2D | ENSG00000214562.14 |
| NYAP1 | ENSG00000166924.8 |
| OGFRL1 | ENSG00000119900.7 |
| OIP5 | ENSG00000104147.8 |
| OLIG2 | ENSG00000205927.4 |
| ONECUT3 | ENSG00000205922.4 |
| OPN5 | ENSG00000124818.14 |
| OPRL1 | ENSG00000125510.15 |
| OR10T1P | ENSG00000203758.4 |
| OR14I1 | ENSG00000189181.4 |
| OR52N5 | ENSG00000181009.4 |
| OR7E106P | ENSG00000258550.1 |
| OR8I1P | ENSG00000255461.1 |
| OR8Q1P | ENSG00000255341.1 |
| ORAI2 | ENSG00000160991.15 |
| OTP | ENSG00000171540.7 |
| OTX2-AS1 | ENSG00000248550.3 |
| OVOL1 | ENSG00000172818.9 |
| OXER1 | ENSG00000162881.6 |
| P2RX5-TAX1BP3 | ENSG00000257950.3 |
| P2RY13 | ENSG00000181631.6 |
| PABPC1L2B-AS1 | ENSG00000226725.2 |
| PADI2 | ENSG00000117115.12 |
| PAGE2B | ENSG00000238269.8 |
| PALM2 | ENSG00000243444.7 |
| PALM2-AKAP2 | ENSG00000157654.17 |
| PALM3 | ENSG00000187867.8 |
| PANDAR | ENSG00000281450.1 |
| PART1 | ENSG00000152931.7 |
| PAWRP1 | ENSG00000225533.1 |
| PCDH19 | ENSG00000165194.15 |
| PCDH7 | ENSG00000169851.15 |
| PCDH8 | ENSG00000136099.13 |
| PCDHB15 | ENSG00000113248.5 |
| PCDHB3 | ENSG00000113205.5 |
| PCDHGA6 | ENSG00000253731.2 |
| PCDHGC4 | ENSG00000242419.5 |
| PCYT1B | ENSG00000102230.13 |
| PDCD10 | ENSG00000114209.14 |
| PDE1B | ENSG00000123360.11 |
| PDZD3 | ENSG00000172367.15 |
| PGAM1P7 | ENSG00000213997.3 |
| PGD | ENSG00000142657.20 |
| PHEX | ENSG00000102174.8 |
| PI3 | ENSG00000124102.4 |
| PIK3CD-AS2 | ENSG00000231789.2 |
| PKP1 | ENSG00000081277.12 |
| PLA2G4F | ENSG00000168907.13 |
| PLAC8 | ENSG00000145287.10 |

TABLE 1-continued

Genes upregulated in glioblastoma multiforme

| Gene Name | GeneID |
| --- | --- |
| PLCXD3 | ENSG00000182836.9 |
| PLPPR2 | ENSG00000105520.10 |
| PLXNC1 | ENSG00000136040.8 |
| PMCHL2 | ENSG00000169040.14 |
| PNMA5 | ENSG00000198883.11 |
| POLR2J | ENSG00000005075.15 |
| POM121B | ENSG00000205578.5 |
| POMP | ENSG00000132963.7 |
| POU3F3 | ENSG00000198914.3 |
| PPIAL4G | ENSG00000236334.2 |
| PPP1R3B | ENSG00000173281.4 |
| PRELP | ENSG00000188783.5 |
| PRICKLE4 | ENSG00000124593.14 |
| PRKCB | ENSG00000166501.12 |
| PRLHR | ENSG00000119973.5 |
| PROK2 | ENSG00000163421.8 |
| PRR13 | ENSG00000205352.10 |
| PRR16 | ENSG00000184838.14 |
| PRR23C | ENSG00000233701.3 |
| PRR26 | ENSG00000180525.11 |
| PRR31 | ENSG00000198454.2 |
| PRR5-ARHGAP8 | ENSG00000248405.10 |
| PRRG3 | ENSG00000130032.15 |
| PRRG4 | ENSG00000135378.3 |
| PRRX1 | ENSG00000116132.11 |
| PRSS16 | ENSG00000112812.15 |
| PRSS21 | ENSG00000007038.10 |
| PRSS36 | ENSG00000178226.10 |
| PTAFR | ENSG00000169403.11 |
| PTCH2 | ENSG00000117425.13 |
| PTCHD1 | ENSG00000165186.10 |
| PTGES2-AS1 | ENSG00000232850.3 |
| QPRT | ENSG00000103485.17 |
| RAB10 | ENSG00000084733.10 |
| RAB2B | ENSG00000129472.12 |
| RAB3D | ENSG00000105514.7 |
| RAB4B-EGLN2 | ENSG00000171570.10 |
| RAB6C | ENSG00000222014.5 |
| RAB7A | ENSG00000075785.12 |
| RAB8A | ENSG00000167461.11 |
| RAD21-AS1 | ENSG00000253327.2 |
| RAD54L | ENSG00000085999.11 |
| RANP5 | ENSG00000228054.2 |
| RASAL2-AS1 | ENSG00000224687.1 |
| RASGEF1C | ENSG00000146090.15 |
| RASL11B | ENSG00000128045.6 |
| RASSF2 | ENSG00000101265.15 |
| RBM22P13 | ENSG00000261284.2 |
| RBM47 | ENSG00000163694.14 |
| REC114 | ENSG00000183324.10 |
| REM2 | ENSG00000139890.9 |
| REXO2 | ENSG00000076043.9 |
| RGMB | ENSG00000174136.11 |
| RGS19 | ENSG00000171700.13 |
| RGS9BP | ENSG00000186326.3 |
| RHBDF1 | ENSG00000007384.15 |
| RIMS1 | ENSG00000079841.18 |
| RNASE7 | ENSG00000165799.4 |
| RNF130 | ENSG00000113269.13 |
| RNU11 | ENSG00000270103.3 |
| ROCK1P1 | ENSG00000263006.6 |
| RORB-AS1 | ENSG00000224825.2 |
| RP1-102E24.6 | ENSG00000256913.1 |
| RP1-107N3.1 | ENSG00000235274.1 |
| RP1-111C20.4 | ENSG00000271913.5 |
| RP1-121G13.3 | ENSG00000220695.1 |
| RP1-140C12.2 | ENSG00000261003.1 |
| RP1-170O19.17 | ENSG00000253308.2 |
| RP1-181J22.1 | ENSG00000244535.1 |
| RP1-267D11.6 | ENSG00000277283.1 |
| RP1-269M15.3 | ENSG00000233308.2 |
| RP1-296G17.3 | ENSG00000233433.1 |
| RP1-308E4.1 | ENSG00000229820.2 |
| RP1-55C23.7 | ENSG00000234484.1 |
| RP1-69B13.2 | ENSG00000216811.2 |
| RP1-69D17.3 | ENSG00000233351.1 |
| RP1-69D17.4 | ENSG00000226149.5 |
| RP1-80N2.3 | ENSG00000261211.1 |
| RP11-102N12.3 | ENSG00000273472.1 |
| RP11-106M3.2 | ENSG00000260729.1 |
| RP11-108K14.8 | ENSG00000254536.1 |
| RP11-108M9.5 | ENSG00000235241.1 |
| RP11-108N13.1 | ENSG00000218476.2 |
| RP11-108P20.4 | ENSG00000267593.1 |
| RP11-109J4.1 | ENSG00000253417.5 |
| RP11-10G12.1 | ENSG00000244538.1 |
| RP11-111D3.2 | ENSG00000236920.2 |
| RP11-111F5.5 | ENSG00000227449.8 |
| RP11-111K18.1 | ENSG00000256646.7 |
| RP11-1217F2.20 | ENSG00000283481.1 |
| RP11-124N3.2 | ENSG00000251487.1 |
| RP11-128A17.1 | ENSG00000259460.1 |
| RP11-130C19.3 | ENSG00000227914.3 |
| RP11-132N15.2 | ENSG00000236412.1 |
| RP11-15A1.7 | ENSG00000266921.1 |
| RP11-165D7.5 | ENSG00000274929.1 |
| RP11-169K17.2 | ENSG00000270531.1 |
| RP11-171I2.1 | ENSG00000267784.1 |
| RP11-177B4.2 | ENSG00000260120.1 |
| RP11-177G23.2 | ENSG00000272137.1 |
| RP11-182E14.1 | ENSG00000248911.2 |
| RP11-186B7.4 | ENSG00000264772.6 |
| RP11-190C22.9 | ENSG00000272967.1 |
| RP11-194N12.2 | ENSG00000267222.1 |
| RP11-1E1.2 | ENSG00000271676.1 |
| RP11-1O2.1 | ENSG00000263547.1 |
| RP11-20D14.6 | ENSG00000249790.2 |
| RP11-20O24.1 | ENSG00000228665.2 |
| RP11-211G3.2 | ENSG00000223401.2 |
| RP11-212I21.2 | ENSG00000260135.6 |
| RP11-212I21.4 | ENSG00000261997.1 |
| RP11-215E13.2 | ENSG00000264990.1 |
| RP11-216N14.5 | ENSG00000231827.3 |
| RP11-21J18.1 | ENSG00000265257.5 |
| RP11-21L23.2 | ENSG00000261578.1 |
| RP11-221J22.1 | ENSG00000144407.3 |
| RP11-221J22.2 | ENSG00000241280.1 |
| RP11-227G15.12 | ENSG00000279762.3 |
| RP11-22C11.2 | ENSG00000261437.1 |
| RP11-23J9.4 | ENSG00000255036.6 |
| RP11-241F15.10 | ENSG00000250753.2 |
| RP11-244F12.1 | ENSG00000259394.2 |
| RP11-261B23.1 | ENSG00000259993.1 |
| RP11-264B14.2 | ENSG00000267449.1 |
| RP11-266I3.1 | ENSG00000234466.1 |
| RP11-277A4.4 | ENSG00000203325.3 |
| RP11-279O22.1 | ENSG00000274637.1 |
| RP11-280K24.4 | ENSG00000258535.1 |
| RP11-281P23.1 | ENSG00000251152.1 |
| RP11-284H19.1 | ENSG00000256879.1 |
| RP11-285E9.5 | ENSG00000265121.1 |
| RP11-290F24.3 | ENSG00000254444.1 |
| RP11-295K3.1 | ENSG00000250644.3 |
| RP11-307C19.1 | ENSG00000259362.2 |
| RP11-307P5.1 | ENSG00000227681.5 |
| RP11-318G8.2 | ENSG00000256079.1 |
| RP11-323C15.1 | ENSG00000235922.1 |
| RP11-335O4.3 | ENSG00000235872.2 |
| RP11-336N8.2 | ENSG00000233947.1 |
| RP11-337C18.8 | ENSG00000237188.3 |
| RP11-338K13.1 | ENSG00000273267.1 |
| RP11-342F21.1 | ENSG00000235901.2 |
| RP11-343C2.9 | ENSG00000260371.1 |
| RP11-346C20.4 | ENSG00000272250.1 |
| RP11-350E12.5 | ENSG00000238110.1 |
| RP11-351M16.4 | ENSG00000282996.1 |
| RP11-354K4.1 | ENSG00000231762.1 |
| RP11-356C4.5 | ENSG00000261172.1 |
| RP11-357D18.1 | ENSG00000250978.5 |
| RP11-358D14.2 | ENSG00000226390.1 |
| RP11-359B12.2 | ENSG00000250132.6 |
| RP11-359M6.1 | ENSG00000257474.5 |

TABLE 1-continued

Genes upregulated in glioblastoma multiforme

| Gene Name | GeneID |
|---|---|
| RP11-35J23.1 | ENSG00000229418.2 |
| RP11-362F19.1 | ENSG00000248810.1 |
| RP11-37C7.3 | ENSG00000261136.1 |
| RP11-385E5.5 | ENSG00000229791.1 |
| RP11-394A14.2 | ENSG00000219926.10 |
| RP11-395G23.3 | ENSG00000254615.2 |
| RP11-403B2.7 | ENSG00000260409.1 |
| RP11-407N17.3 | ENSG00000258941.3 |
| RP11-407N8.4 | ENSG00000271596.1 |
| RP11-409C19.2 | ENSG00000253223.1 |
| RP11-413N10.3 | ENSG00000283415.1 |
| RP11-422P24.9 | ENSG00000231416.1 |
| RP11-439E19.7 | ENSG00000235021.1 |
| RP11-442O1.3 | ENSG00000275088.1 |
| RP11-445O3.3 | ENSG00000260763.1 |
| RP11-448A19.1 | ENSG00000273329.1 |
| RP11-449D8.1 | ENSG00000265485.5 |
| RP11-44F14.1 | ENSG00000260078.3 |
| RP11-44F14.2 | ENSG00000261804.1 |
| RP11-44F21.3 | ENSG00000249717.1 |
| RP11-44K6.3 | ENSG00000253939.1 |
| RP11-456N14.4 | ENSG00000283148.1 |
| RP11-459E5.1 | ENSG00000253125.1 |
| RP11-459O1.2 | ENSG00000234426.1 |
| RP11-461O14.3 | ENSG00000271196.1 |
| RP11-468E2.4 | ENSG00000259529.1 |
| RP11-473M20.16 | ENSG00000261889.1 |
| RP11-475O6.1 | ENSG00000233008.5 |
| RP11-488I20.8 | ENSG00000260958.2 |
| RP11-489E7.1 | ENSG00000253604.1 |
| RP11-496I9.1 | ENSG00000254815.5 |
| RP11-497K21.1 | ENSG00000249419.1 |
| RP11-504G3.4 | ENSG00000256282.1 |
| RP11-507K12.1 | ENSG00000283321.1 |
| RP11-50E11.2 | ENSG00000231588.1 |
| RP11-513I15.6 | ENSG00000225339.3 |
| RP11-51L5.5 | ENSG00000263887.6 |
| RP11-525J21.1 | ENSG00000249892.1 |
| RP11-529E15.1 | ENSG00000272027.2 |
| RP11-531H8.2 | ENSG00000254789.2 |
| RP11-541N10.3 | ENSG00000260461.1 |
| RP11-543P15.1 | ENSG00000227081.5 |
| RP11-544O24.2 | ENSG00000274423.1 |
| RP11-54J7.2 | ENSG00000255368.1 |
| RP11-54O7.18 | ENSG00000273443.1 |
| RP11-554D15.1 | ENSG00000223786.1 |
| RP11-55K22.2 | ENSG00000213109.4 |
| RP11-560A7.1 | ENSG00000250079.1 |
| RP11-561B11.2 | ENSG00000258790.1 |
| RP11-562L8.1 | ENSG00000257522.5 |
| RP11-567N4.3 | ENSG00000250735.5 |
| RP11-572M11.4 | ENSG00000240057.5 |
| RP11-576D8.4 | ENSG00000224717.1 |
| RP11-57G10.8 | ENSG00000272892.1 |
| RP11-57H14.4 | ENSG00000260917.1 |
| RP11-580P21.1 | ENSG00000249976.2 |
| RP11-586D19.1 | ENSG00000249896.2 |
| RP11-598F7.4 | ENSG00000249695.6 |
| RP11-598P20.3 | ENSG00000254673.1 |
| RP11-598P20.5 | ENSG00000254673.1 |
| RP11-603J24.9 | ENSG00000257411.1 |
| RP11-613F22.7 | ENSG00000256734.1 |
| RP11-617J18.1 | ENSG00000258375.2 |
| RP11-61I13.3 | ENSG00000235033.7 |
| RP11-61J19.5 | ENSG00000260805.2 |
| RP11-621K7.1 | ENSG00000226439.3 |
| RP11-627K11.1 | ENSG00000243517.1 |
| RP11-631N16.2 | ENSG00000257354.2 |
| RP11-632C17__A.1 | ENSG00000230202.1 |
| RP11-634H22.1 | ENSG00000273391.1 |
| RP11-645C24.5 | ENSG00000260306.1 |
| RP11-65B23.5 | ENSG00000276478.1 |
| RP11-65L3.4 | ENSG00000270956.1 |
| RP11-667K14.5 | ENSG00000262810.1 |
| RP11-66N11.7 | ENSG00000228616.1 |
| RP11-677O4.2 | ENSG00000260759.1 |
| RP11-680B3.2 | ENSG00000240521.1 |
| RP11-686D16.1 | ENSG00000231662.1 |
| RP11-694I15.7 | ENSG00000270441.1 |
| RP11-6O2.4 | ENSG00000261054.1 |
| RP11-706O15.7 | ENSG00000205662.2 |
| RP11-707M1.1 | ENSG00000205035.8 |
| RP11-70J12.1 | ENSG00000230001.1 |
| RP11-726G1.1 | ENSG00000214776.9 |
| RP11-728G15.1 | ENSG00000256008.2 |
| RP11-74M13.4 | ENSG00000258679.1 |
| RP11-75A5.1 | ENSG00000251162.1 |
| RP11-761N21.2 | ENSG00000234287.1 |
| RP11-76E16.2 | ENSG00000257674.1 |
| RP11-775B15.3 | ENSG00000254037.2 |
| RP11-794G24.1 | ENSG00000256443.1 |
| RP11-7F17.3 | ENSG00000258819.1 |
| RP11-7K24.3 | ENSG00000261068.2 |
| RP11-80H5.5 | ENSG00000249962.1 |
| RP11-814E24.1 | ENSG00000203462.2 |
| RP11-834C11.12 | ENSG00000273049.1 |
| RP11-838N2.3 | ENSG00000259256.1 |
| RP11-848G14.5 | ENSG00000250138.4 |
| RP11-84A19.2 | ENSG00000203620.2 |
| RP11-862G15.1 | ENSG00000258742.5 |
| RP11-864I4.1 | ENSG00000255508.7 |
| RP11-87M18.2 | ENSG00000226484.2 |
| RP11-88I21.2 | ENSG00000244215.1 |
| RP11-92A5.2 | ENSG00000250538.5 |
| RP11-96D1.10 | ENSG00000263276.1 |
| RP11-96K19.5 | ENSG00000273010.1 |
| RP11-989E6.10 | ENSG00000261200.1 |
| RP13-1032I1.10 | ENSG00000262660.1 |
| RP13-270P17.1 | ENSG00000264235.5 |
| RP13-30A9.2 | ENSG00000229882.1 |
| RP13-395E19.2 | ENSG00000260211.2 |
| RP13-467H17.1 | ENSG00000261693.1 |
| RP13-585F24.1 | ENSG00000241612.1 |
| RP13-650J16.1 | ENSG00000264569.1 |
| RP13-685P2.7 | ENSG00000270773.1 |
| RP13-766D20.4 | ENSG00000278200.1 |
| RP13-890H12.2 | ENSG00000267288.2 |
| RP3-337H4.8 | ENSG00000203362.2 |
| RP3-340B19.2 | ENSG00000219023.1 |
| RP3-368B9.2 | ENSG00000250681.1 |
| RP3-399L15.1 | ENSG00000232395.1 |
| RP3-428L16.2 | ENSG00000272841.1 |
| RP3-429O6.1 | ENSG00000223342.2 |
| RP3-454G6.2 | ENSG00000283683.1 |
| RP3-455J7.4 | ENSG00000241666.2 |
| RP3-512B11.3 | ENSG00000261189.1 |
| RP4-535B20.1 | ENSG00000231485.1 |
| RP4-613B23.5 | ENSG00000280571.1 |
| RP4-684O24.5 | ENSG00000233896.1 |
| RP4-701O16.5 | ENSG00000253183.1 |
| RP4-788P17.1 | ENSG00000223479.3 |
| RP5-1014O16.1 | ENSG00000223377.1 |
| RP5-1031J8.1 | ENSG00000229976.1 |
| RP5-1063M23.3 | ENSG00000250770.3 |
| RP5-1142J19.2 | ENSG00000224629.1 |
| RP5-857K21.4 | ENSG00000230021.8 |
| RP5-864K19.7 | ENSG00000273637.1 |
| RP5-921G16.1 | ENSG00000242593.5 |
| RP5-928E24.2 | ENSG00000235461.1 |
| RP5-991O23.1 | ENSG00000253510.1 |
| RPIA | ENSG00000153574.8 |
| RPL12P8 | ENSG00000219932.6 |
| RPL13AP6 | ENSG00000234118.1 |
| RPL14P1 | ENSG00000139239.7 |
| RPL17P43 | ENSG00000228331.2 |
| RPL18AP3 | ENSG00000213442.5 |
| RPL21P75 | ENSG00000213860.4 |
| RPL23AP2 | ENSG00000225067.4 |
| RPL23AP63 | ENSG00000243721.1 |
| RPL23AP74 | ENSG00000227694.1 |
| RPL26P19 | ENSG00000226221.1 |
| RPL34 | ENSG00000109475.16 |

TABLE 1-continued

Genes upregulated in glioblastoma multiforme

| Gene Name | GeneID |
| --- | --- |
| RPL34P31 | ENSG00000239223.3 |
| RPL36 | ENSG00000130255.12 |
| RPL37P6 | ENSG00000241431.1 |
| RPL41 | ENSG00000229117.8 |
| RPL41P2 | ENSG00000256338.2 |
| RPS15AP1 | ENSG00000214535.3 |
| RPS15AP38 | ENSG00000237668.1 |
| RPS27 | ENSG00000177954.11 |
| RPS27P29 | ENSG00000240231.1 |
| RPS4XP22 | ENSG00000239830.1 |
| RPS7P1 | ENSG00000263266.2 |
| RPSAP52 | ENSG00000241749.4 |
| RSPO2 | ENSG00000147655.10 |
| S100A11 | ENSG00000163191.5 |
| S100A12 | ENSG00000163221.8 |
| S100A8 | ENSG00000143546.9 |
| S100A9 | ENSG00000163220.10 |
| SAMD15 | ENSG00000100583.4 |
| SAMHD1 | ENSG00000101347.8 |
| SBF1P1 | ENSG00000248522.1 |
| SBK1 | ENSG00000188322.4 |
| SCARF2 | ENSG00000244486.8 |
| SCARNA9 | ENSG00000254911.3 |
| SCG3 | ENSG00000104112.8 |
| SCML2 | ENSG00000102098.17 |
| SCN2B | ENSG00000149575.5 |
| SCN5A | ENSG00000183873.15 |
| SCRG1 | ENSG00000164106.7 |
| SDCBP | ENSG00000137575.11 |
| SEMA3B | ENSG00000012171.18 |
| SENCR | ENSG00000254703.2 |
| SERPINA1 | ENSG00000197249.13 |
| SERPINB10 | ENSG00000242550.5 |
| SFTPB | ENSG00000168878.16 |
| SGPL1 | ENSG00000166224.16 |
| SH3GL2 | ENSG00000107295.9 |
| SHC4 | ENSG00000185634.11 |
| SHISA7 | ENSG00000187902.11 |
| SIAH2 | ENSG00000181788.3 |
| SIGLEC1 | ENSG00000088827.12 |
| SIGLEC12 | ENSG00000254521.6 |
| SIRPA | ENSG00000198053.11 |
| SIX5 | ENSG00000177045.7 |
| SKA3 | ENSG00000165480.15 |
| SKIDA1 | ENSG00000180592.16 |
| SKOR2 | ENSG00000215474.7 |
| SLC13A3 | ENSG00000158296.13 |
| SLC13A5 | ENSG00000141485.16 |
| SLC16A3 | ENSG00000141526.15 |
| SLC16A6 | ENSG00000108932.11 |
| SLC18A1 | ENSG00000036565.14 |
| SLC18A3 | ENSG00000187714.6 |
| SLC22A9 | ENSG00000149742.9 |
| SLC25A10 | ENSG00000183048.11 |
| SLC25A3 | ENSG00000075415.12 |
| SLC25A37 | ENSG00000147454.13 |
| SLC2A6 | ENSG00000160326.13 |
| SLC3A1 | ENSG00000138079.13 |
| SLC5A10 | ENSG00000154025.15 |
| SLC6A18 | ENSG00000164363.9 |
| SLC7A10 | ENSG00000130876.11 |
| SLC7A11-AS1 | ENSG00000250033.5 |
| SLC9A3P1 | ENSG00000233011.1 |
| SLC9A7P1 | ENSG00000227825.4 |
| SLC9B1 | ENSG00000164037.16 |
| SLCO1A2 | ENSG00000084453.16 |
| SLCO1B1 | ENSG00000134538.2 |
| SLIRP | ENSG00000119705.9 |
| SMAP1 | ENSG00000112305.14 |
| SNCA | ENSG00000145335.15 |
| SNX3 | ENSG00000112305.14 |
| SOCS2-AS1 | ENSG00000246985.7 |
| SOD3 | ENSG00000109610.5 |
| SOSTDC1 | ENSG00000171243.7 |
| SOX1 | ENSG00000182968.4 |
| SOX2-OT | ENSG00000242808.7 |
| SPAG5-AS1 | ENSG00000227543.4 |
| SPANXA2-OT1 | ENSG00000277215.1 |
| SPATA18 | ENSG00000163071.10 |
| SPEG | ENSG00000072195.14 |
| SPINK13 | ENSG00000214510.9 |
| SPINT1 | ENSG00000166145.14 |
| SPTBN2 | ENSG00000173898.11 |
| SRCIN1 | ENSG00000277363.4 |
| SRGN | ENSG00000122862.4 |
| SRMS | ENSG00000125508.3 |
| SRRM4 | ENSG00000139767.8 |
| SSTR1 | ENSG00000139874.5 |
| SSTR5-AS1 | ENSG00000261713.6 |
| ST13P18 | ENSG00000234322.1 |
| ST13P3 | ENSG00000257773.1 |
| ST6GALNAC1 | ENSG00000070526.14 |
| ST6GALNAC2 | ENSG00000070731.10 |
| STAB2 | ENSG00000136011.14 |
| STARD5 | ENSG00000172345.13 |
| STEAP3-AS1 | ENSG00000229867.1 |
| STK38L | ENSG00000211455.7 |
| STMN1 | ENSG00000117632.21 |
| STRADB | ENSG00000082146.12 |
| STX3 | ENSG00000166900.15 |
| STXBP5L | ENSG00000145087.12 |
| STXBP6 | ENSG00000168952.15 |
| SULT1B1 | ENSG00000173597.8 |
| SYNGR3 | ENSG00000127561.14 |
| TACR1 | ENSG00000115353.10 |
| TANC2 | ENSG00000170921.14 |
| TANK | ENSG00000136560.13 |
| TARM1 | ENSG00000248385.7 |
| TAS2R12 | ENSG00000256682.2 |
| TBL1XR1 | ENSG00000177565.16 |
| TBX5 | ENSG00000089225.19 |
| TCF23 | ENSG00000163792.6 |
| TCP11L2 | ENSG00000166046.10 |
| TDGF1P5 | ENSG00000254274.1 |
| TEDDM1 | ENSG00000203730.2 |
| TEN1-CDK3 | ENSG00000261408.5 |
| TENM4 | ENSG00000149256.15 |
| TERT | ENSG00000164362.18 |
| THAP7-AS1 | ENSG00000230513.1 |
| TIMM9 | ENSG00000100575.13 |
| TIMP2 | ENSG00000035862.12 |
| TIPIN | ENSG00000075131.9 |
| TLR2 | ENSG00000137462.6 |
| TLR4 | ENSG00000136869.13 |
| TLX1 | ENSG00000107807.12 |
| TMEM117 | ENSG00000139173.9 |
| TMEM125 | ENSG00000179178.10 |
| TMEM150B | ENSG00000180061.9 |
| TMEM151B | ENSG00000178233.17 |
| TMEM179 | ENSG00000258986.6 |
| TMEM184B | ENSG00000198792.12 |
| TMEM189-UBE2V1 | ENSG00000124208.16 |
| TMEM241 | ENSG00000134490.13 |
| TMEM38B | ENSG00000095209.11 |
| TMEM39B | ENSG00000121775.17 |
| TMEM51-AS1 | ENSG00000175147.11 |
| TMEM59 | ENSG00000116209.11 |
| TMEM78 | ENSG00000177800.2 |
| TMEM97P2 | ENSG00000253866.1 |
| TMLHE | ENSG00000185973.10 |
| TMPRSS4 | ENSG00000137648.17 |
| TMSB4XP1 | ENSG00000236876.3 |
| TMSB4XP4 | ENSG00000223551.1 |
| TNFAIP6 | ENSG00000123610.4 |
| TNFRSF10C | ENSG00000173535.13 |
| TNFRSF19 | ENSG00000127863.15 |
| TOLLIP-AS1 | ENSG00000255153.1 |
| TP53 | ENSG00000141510.16 |
| TP53I11 | ENSG00000175274.18 |
| TPCN2 | ENSG00000162341.16 |
| TRIM3 | ENSG00000110171.18 |
| TRIM7 | ENSG00000146054.17 |

TABLE 1-continued

Genes upregulated in glioblastoma multiforme

| Gene Name | GeneID |
|---|---|
| tRNA-Arg-ACG-2-3 | tRNA-Arg-ACG-2-3 |
| tRNA-Arg-CCG-1-2 | tRNA-Arg-CCG-1-2 |
| tRNA-Arg-CCG-1-3 | tRNA-Arg-CCG-1-3 |
| tRNA-Arg-CCT-4-1 | tRNA-Arg-CCT-4-1 |
| tRNA-Arg-TCG-1-1 | tRNA-Arg-TCG-1-1 |
| tRNA-Arg-TCT-1-1 | tRNA-Arg-TCT-1-1 |
| tRNA-Arg-TCT-3-1 | tRNA-Arg-TCT-3-1 |
| tRNA-Asn-GTT-1-1 | tRNA-Asn-GTT-1-1 |
| tRNA-Asn-GTT-17-1 | tRNA-Asn-GTT-17-1 |
| tRNA-Asn-GTT-2-2 | tRNA-Asn-GTT-2-2 |
| tRNA-Asn-GTT-2-4 | tRNA-Asn-GTT-2-4 |
| tRNA-Asn-GTT-9-2 | tRNA-Asn-GTT-9-2 |
| tRNA-Asn-GTT-chr1-140 | tRNA-Asn-GTT-chr1-140 |
| tRNA-Asp-GTC-1-1 | tRNA-Asp-GTC-1-1 |
| tRNA-Asp-GTC-2-1 | tRNA-Asp-GTC-2-1 |
| tRNA-Asp-GTC-2-10 | tRNA-Asp-GTC-2-10 |
| tRNA-Asp-GTC-2-2 | tRNA-Asp-GTC-2-2 |
| tRNA-Asp-GTC-2-3 | tRNA-Asp-GTC-2-3 |
| tRNA-Asp-GTC-2-4 | tRNA-Asp-GTC-2-4 |
| tRNA-Asp-GTC-2-5 | tRNA-Asp-GTC-2-5 |
| tRNA-Asp-GTC-2-6 | tRNA-Asp-GTC-2-6 |
| tRNA-Asp-GTC-2-7 | tRNA-Asp-GTC-2-7 |
| tRNA-Asp-GTC-2-8 | tRNA-Asp-GTC-2-8 |
| tRNA-Asp-GTC-2-9 | tRNA-Asp-GTC-2-9 |
| tRNA-Asp-GTC-4-1 | tRNA-Asp-GTC-4-1 |
| tRNA-Cys-GCA-6-1 | tRNA-Cys-GCA-6-1 |
| tRNA-Gln-CTG-1-2 | tRNA-Gln-CTG-1-2 |
| tRNA-Gln-TTG-1-1 | tRNA-Gln-TTG-1-1 |
| tRNA-Glu-CTC-1-1 | tRNA-Glu-CTC-1-1 |
| tRNA-Glu-CTC-1-6 | tRNA-Glu-CTC-1-6 |
| tRNA-Glu-CTC-1-7 | tRNA-Glu-CTC-1-7 |
| tRNA-Glu-TTC-1-1 | tRNA-Glu-TTC-1-1 |
| tRNA-Glu-TTC-11-1 | tRNA-Glu-TTC-11-1 |
| tRNA-Glu-TTC-3-1 | tRNA-Glu-TTC-3-1 |
| tRNA-Glu-TTC-8-1 | tRNA-Glu-TTC-8-1 |
| tRNA-Gly-CCC-1-2 | tRNA-Gly-CCC-1-2 |
| tRNA-Gly-CCC-2-1 | tRNA-Gly-CCC-2-1 |
| tRNA-Gly-CCC-7-1 | tRNA-Gly-CCC-7-1 |
| tRNA-Gly-GCC-2-2 | tRNA-Gly-GCC-2-2 |
| tRNA-Gly-TCC-1-1 | tRNA-Gly-TCC-1-1 |
| tRNA-Gly-TCC-2-1 | tRNA-Gly-TCC-2-1 |
| tRNA-Gly-TCC-3-1 | tRNA-Gly-TCC-3-1 |
| tRNA-His-GTG-1-1 | tRNA-His-GTG-1-1 |
| tRNA-His-GTG-1-3 | tRNA-His-GTG-1-3 |
| tRNA-His-GTG-1-5 | tRNA-His-GTG-1-5 |
| tRNA-His-GTG-1-9 | tRNA-His-GTG-1-9 |
| tRNA-His-GTG-2-1 | tRNA-His-GTG-2-1 |
| tRNA-Ile-AAT-5-1 | tRNA-Ile-AAT-5-1 |
| tRNA-iMet-CAT-1-1 | tRNA-iMet-CAT-1-1 |
| tRNA-Lys-CTT-1-2 | tRNA-Lys-CTT-1-2 |
| tRNA-Lys-CTT-2-1 | tRNA-Lys-CTT-2-1 |
| tRNA-Lys-CTT-2-4 | tRNA-Lys-CTT-2-4 |
| tRNA-Lys-TTT-3-3 | tRNA-Lys-TTT-3-3 |
| tRNA-Lys-TTT-3-4 | tRNA-Lys-TTT-3-4 |
| tRNA-Lys-TTT-3-5 | tRNA-Lys-TTT-3-5 |
| tRNA-Lys-TTT-9-1 | tRNA-Lys-TTT-9-1 |
| tRNA-Met-CAT-1-1 | tRNA-Met-CAT-1-1 |
| tRNA-Met-CAT-3-1 | tRNA-Met-CAT-3-1 |
| tRNA-Met-CAT-4-1 | tRNA-Met-CAT-4-1 |
| tRNA-Met-CAT-5-1 | tRNA-Met-CAT-5-1 |
| tRNA-Met-CAT-6-1 | tRNA-Met-CAT-6-1 |
| tRNA-Pro-AGG-1-1 | tRNA-Pro-AGG-1-1 |
| tRNA-Pro-CGG-1-2 | tRNA-Pro-CGG-1-2 |
| tRNA-SeC-TCA-1-1 | tRNA-SeC-TCA-1-1 |
| tRNA-Ser-AGA-3-1 | tRNA-Ser-AGA-3-1 |
| tRNA-Ser-CGA-1-1 | tRNA-Ser-CGA-1-1 |
| tRNA-Ser-TGA-4-1 | tRNA-Ser-TGA-4-1 |
| tRNA-Thr-AGT-6-1 | tRNA-Thr-AGT-6-1 |
| tRNA-Thr-CGT-2-1 | tRNA-Thr-CGT-2-1 |
| tRNA-Thr-TGT-2-1 | tRNA-Thr-TGT-2-1 |
| tRNA-Trp-CCA-2-1 | tRNA-Trp-CCA-2-1 |
| tRNA-Trp-CCA-4-1 | tRNA-Trp-CCA-4-1 |
| tRNA-Und-NNN-4-1 | tRNA-Und-NNN-4-1 |
| tRNA-Val-AAC-1-2 | tRNA-Val-AAC-1-2 |
| tRNA-Val-AAC-1-3 | tRNA-Val-AAC-1-3 |
| tRNA-Val-AAC-1-4 | tRNA-Val-AAC-1-4 |
| tRNA-Val-AAC-3-1 | tRNA-Val-AAC-3-1 |
| tRNA-Val-CAC-1-4 | tRNA-Val-CAC-1-4 |
| tRNA-Val-CAC-2-1 | tRNA-Val-CAC-2-1 |
| tRNA-Val-CAC-3-1 | tRNA-Val-CAC-3-1 |
| tRNA-Val-TAC-1-2 | tRNA-Val-TAC-1-2 |
| TRNP1 | ENSG00000253368.3 |
| TRPM1 | ENSG00000134160.13 |
| TSLP | ENSG00000145777.14 |
| TSPAN10 | ENSG00000182612.10 |
| TSPAN5 | ENSG00000168785.7 |
| TSPO | ENSG00000100300.17 |
| TTC28-AS1 | ENSG00000235954.6 |
| TTC34 | ENSG00000215912.12 |
| TUBGCP2 | ENSG00000130640.13 |
| TUFT1 | ENSG00000143367.15 |
| UBALD2 | ENSG00000185262.8 |
| UBE2B | ENSG00000119048.7 |
| UBE2D1 | ENSG00000072401.14 |
| UBE2D3 | ENSG00000109332.19 |
| UBE2V1 | ENSG00000244687.11 |
| UBLCP1 | ENSG00000164332.7 |
| UGT2A3 | ENSG00000135220.10 |
| UNC80 | ENSG00000144406.18 |
| UPK1A | ENSG00000105668.7 |
| USP12 | ENSG00000152484.13 |
| USP12PX | ENSG00000226081.2 |
| USP12PY | ENSG00000232927.1 |
| USP15 | ENSG00000135655.14 |
| USP17L1 | ENSG00000230549.3 |
| USP2 | ENSG00000036672.15 |
| USP43 | ENSG00000154914.16 |
| VLDLR | ENSG00000147852.15 |
| VNN2 | ENSG00000112303.13 |
| VSTM1 | ENSG00000189068.9 |
| VSTM2L | ENSG00000132821.11 |
| VWA1 | ENSG00000179403.11 |
| WDFY3 | ENSG00000163625.15 |
| WDR31 | ENSG00000148225.15 |
| WISP3 | ENSG00000112761.19 |
| XX-FW83563B9.5 | ENSG00000280195.1 |
| XXYLT1 | ENSG00000173950.15 |
| XYLB | ENSG00000093217.9 |
| YIPF6 | ENSG00000181704.11 |
| YOD1 | ENSG00000180667.10 |
| YWHAB | ENSG00000166913.12 |
| ZBTB7B | ENSG00000160685.13 |
| ZEB2P1 | ENSG00000249506.3 |
| ZFAS1 | ENSG00000177410.12 |
| ZFHX3 | ENSG00000140836.14 |
| ZFRP1 | ENSG00000234570.1 |
| ZNF19 | ENSG00000157429.15 |
| ZNF205 | ENSG00000122386.10 |
| ZNF226 | ENSG00000167380.16 |
| ZNF30-AS1 | ENSG00000270876.1 |
| ZNF302 | ENSG00000089335.20 |
| ZNF536 | ENSG00000198597.8 |
| ZNF596 | ENSG00000172748.12 |
| ZNF773 | ENSG00000152439.12 |
| ZNF814 | ENSG00000204514.9 |
| ZSWIM6 | ENSG00000130449.5 |

TABLE 2

Genes downregulated in patients with GBM

| Gene Name | GeneID |
|---|---|
| AB019441.29 | ENSG00000225200.2 |
| ABHD17AP3 | ENSG00000250536.1 |
| ABLIM1 | ENSG00000099204.18 |
| ABRACL | ENSG00000146386.7 |
| AC002310.17 | ENSG00000261588.1 |
| AC005251.3 | ENSG00000219451.3 |

TABLE 2-continued

Genes downregulated in patients with GBM

| Gene Name | GeneID |
|---|---|
| AC007969.5 | ENSG00000233762.3 |
| AC009362.2 | ENSG00000233287.1 |
| AC009474.2 | ENSG00000230355.1 |
| AC010468.1 | ENSG00000214784.4 |
| AC012005.1 | ENSG00000279274.1 |
| AC016708.2 | ENSG00000230076.1 |
| AC016716.1 | ENSG00000223427.1 |
| AC027612.1 | ENSG00000232531.3 |
| AC067969.1 | ENSG00000269445.1 |
| AC078899.1 | ENSG00000213985.4 |
| AC092155.1 | ENSG00000229503.1 |
| AC097523.1 | ENSG00000233045.1 |
| AC104843.3 | ENSG00000225416.1 |
| AC144652.1 | ENSG00000273117.1 |
| ACTBP2 | ENSG00000213763.4 |
| ACTBP8 | ENSG00000220267.1 |
| ACTG1P10 | ENSG00000231340.1 |
| ADGRB3 | ENSG00000135298.13 |
| AHDC1 | ENSG00000126705.13 |
| AL513412.1 | ENSG00000282960.1 |
| ALG2 | ENSG00000119523.9 |
| ANKRD20A17P | ENSG00000251056.1 |
| ANKS1B | ENSG00000185046.18 |
| ANP32BP1 | ENSG00000259790.1 |
| AP3D1 | ENSG00000065000.15 |
| AQP7 | ENSG00000165269.12 |
| ARL6 | ENSG00000113966.9 |
| ARL6IP4 | ENSG00000182196.13 |
| ATP2B3 | ENSG00000067842.17 |
| ATP5HP4 | ENSG00000234925.2 |
| ATP6V1G2-DDX39B | ENSG00000254870.5 |
| ATPIF1 | ENSG00000130770.17 |
| AXIN1 | ENSG00000103126.14 |
| B3GAT1 | ENSG00000109956.12 |
| BCAS1 | ENSG00000064787.13 |
| BCLAF1P1 | ENSG00000248966.1 |
| BTF3P8 | ENSG00000236813.1 |
| C11orf95 | ENSG00000188070.9 |
| C12orf57 | ENSG00000111678.10 |
| C17orf97 | ENSG00000187624.8 |
| C19orf43 | ENSG00000123144.10 |
| C19orf53 | ENSG00000104979.8 |
| C1orf168 | ENSG00000187889.12 |
| C1orf94 | ENSG00000142698.14 |
| C22orf34 | ENSG00000188511.12 |
| C3orf52 | ENSG00000114529.12 |
| C8orf82 | ENSG00000213563.6 |
| CAPG | ENSG00000042493.15 |
| CARD11 | ENSG00000198286.9 |
| CBX1 | ENSG00000108468.14 |
| CCDC9 | ENSG00000105321.12 |
| CCL3L3 | ENSG00000276085.1 |
| CDK11A | ENSG00000008128.22 |
| CDK11B | ENSG00000248333.8 |
| CDK20 | ENSG00000156345.17 |
| CH507-338C24.1 | ENSG00000277991.4 |
| CHCHD6 | ENSG00000159685.10 |
| CHD4 | ENSG00000111642.14 |
| CHGA | ENSG00000100604.12 |
| COLQ | ENSG00000206561.12 |
| COX4I1 | ENSG00000131143.8 |
| COX7CP1 | ENSG00000235957.1 |
| CROCCP2 | ENSG00000215908.9 |
| CSAD | ENSG00000139631.18 |
| CTA-29F11.1 | ENSG00000260708.1 |
| CTD-2017C7.2 | ENSG00000259088.1 |
| CTD-2192J16.15 | ENSG00000178464.6 |
| CTD-2270N23.1 | ENSG00000213862.4 |
| CTD-2545G14.7 | ENSG00000262526.2 |
| CTD-2554C21.2 | ENSG00000267640.6 |
| CTD-3035D6.1 | ENSG00000213315.5 |
| CXCL8 | ENSG00000169429.10 |
| DDX3X | ENSG0000021530E9 |
| DEF6 | ENSG00000023892.10 |
| DHX37 | ENSG00000150990.7 |
| DHX38 | ENSG00000140829.11 |
| DNAI1 | ENSG00000122735.15 |
| EDF1 | ENSG00000107223.12 |
| EEF1A1P12 | ENSG00000214199.3 |
| EEF1A1P13 | ENSG00000250182.3 |
| EEF1A1P14 | ENSG00000233057.1 |
| EEF1A1P16 | ENSG00000213235.3 |
| EEF1A1P19 | ENSG00000249855.1 |
| EEF1A1P22 | ENSG00000259612.1 |
| EEF1A1P6 | ENSG00000233476.3 |
| EEF1A1P8 | ENSG00000223529.1 |
| EEF1B2P3 | ENSG00000232472.1 |
| EEF1D | ENSG00000104529.17 |
| EEF1GP2 | ENSG00000250346.1 |
| EIF1P3 | ENSG00000231684.3 |
| EIF1P7 | ENSG00000213772.3 |
| EIF3A | ENSG00000107581.12 |
| EIF4A2 | ENSG00000156976.15 |
| EIF4BP7 | ENSG00000225031.1 |
| ERRFI1 | ENSG00000116285.12 |
| ETFB | ENSG00000105379.9 |
| F2RL2 | ENSG00000164220.6 |
| FAM219A | ENSG00000164970.14 |
| FAM92B | ENSG00000153789.12 |
| FAU | ENSG00000149806.10 |
| FBL | ENSG00000105202.7 |
| FTH1P12 | ENSG00000213362.3 |
| FTH1P8 | ENSG00000219507.4 |
| GAA | ENSG00000171298.12 |
| GAPDHP40 | ENSG00000248626.1 |
| GAS8 | ENSG00000141013.15 |
| GLDC | ENSG00000178445.8 |
| GOLGA3 | ENSG00000090615.13 |
| GPX4 | ENSG00000167468.16 |
| GS1-345D13.1 | ENSG00000278388.1 |
| GTF2F1 | ENSG00000125651.13 |
| GTPBP3 | ENSG00000130299.16 |
| GXYLT1P4 | ENSG00000275026.1 |
| H3F3B | ENSG00000132475.9 |
| HIRIP3 | ENSG00000149929.15 |
| HIST1H1D | ENSG00000124575.6 |
| HMGN2P3 | ENSG00000230330.1 |
| HNRNPA1 | ENSG00000135486.17 |
| HNRNPA1P10 | ENSG00000214223.4 |
| HNRNPA1P35 | ENSG00000225695.1 |
| HNRNPA1P4 | ENSG00000206228.4 |
| HNRNPA1P6 | ENSG00000229887.4 |
| HNRNPA1P7 | ENSG00000215492.6 |
| HNRNPA3 | ENSG00000170144.19 |
| HNRNPA3P5 | ENSG00000236565.3 |
| HNRNPAB | ENSG00000197451.11 |
| HNRNPD | ENSG00000138668.18 |
| HNRNPU | ENSG00000153187.17 |
| HNRNPUL2 | ENSG00000214753.2 |
| HSP90AB2P | ENSG00000205940.8 |
| HSPA8P20 | ENSG00000234564.1 |
| IL32 | ENSG00000008517.16 |
| JUN | ENSG00000177606.6 |
| KCNQ5 | ENSG00000185760.15 |
| KIF7 | ENSG00000166813.14 |
| KLF16 | ENSG00000129911.8 |
| KLHL34 | ENSG00000185915.5 |
| KPNA5 | ENSG00000196911.10 |
| KRI1 | ENSG00000129347.19 |
| KRT16P3 | ENSG00000214822.8 |
| LAPTM4B | ENSG00000104341.16 |
| LBH | ENSG00000213626.11 |
| LCT | ENSG00000115850.9 |
| LDHAP5 | ENSG00000213574.2 |
| LEFTY1 | ENSG00000243709.1 |
| LINC01016 | ENSG00000249346.6 |
| LINC01106 | ENSG00000175772.10 |
| LRPPRC | ENSG00000138095.18 |
| LUZP4P1 | ENSG00000232853.1 |
| MANEA-AS1 | ENSG00000261366.1 |
| MAP7D1 | ENSG00000116871.15 |
| MAPK11 | ENSG00000185386.14 |

TABLE 2-continued

Genes downregulated in patients with GBM

| Gene Name | GeneID |
|---|---|
| MLLT6 | ENSG00000275023.4 |
| MRFAP1 | ENSG00000179010.14 |
| MTATP8P1 | ENSG00000240409.1 |
| MTND2P9 | ENSG00000225901.1 |
| MTRNR2L10 | ENSG00000256045.2 |
| MTRNR2L3 | ENSG00000256222.2 |
| MYO18A | ENSG00000196535.15 |
| MYOM2 | ENSG00000036448.9 |
| NAALADL1 | ENSG00000168060.15 |
| NACA | ENSG00000196531.10 |
| NACA3P | ENSG00000121089.4 |
| NPM1P24 | ENSG00000215086.2 |
| NPM1P27 | ENSG00000249353.2 |
| NPM1P39 | ENSG00000225159.1 |
| NPM1P46 | ENSG00000213104.3 |
| NR4A2 | ENSG00000153234.13 |
| NUDC | ENSG00000090273.13 |
| OR2H4P | ENSG00000230598.1 |
| PCDHA1 | ENSG00000204970.9 |
| PDCD4 | ENSG00000150593.16 |
| PLEKHJ1 | ENSG00000104886.10 |
| PLXDC1 | ENSG00000161381.13 |
| PMEPA1 | ENSG00000124225.15 |
| PMS2P2 | ENSG00000278416.1 |
| PNN | ENSG00000100941.8 |
| PNRC2P1 | ENSG00000228217.1 |
| PPIAP29 | ENSG00000214975.4 |
| PPIAP31 | ENSG00000217094.2 |
| PRCAT47 | ENSG00000260896.5 |
| PRMT5-AS1 | ENSG00000237054.9 |
| PRPF6 | ENSG00000101161.7 |
| PRR34-AS1 | ENSG00000241990.5 |
| PRTFDC1 | ENSG00000099256.18 |
| PSMA7 | ENSG00000101182.14 |
| PTMAP2 | ENSG00000197744.5 |
| PTMAP5 | ENSG00000214182.5 |
| PTRF | ENSG00000177469.12 |
| PTRH1 | ENSG00000187024.13 |
| RFT1 | ENSG00000163933.9 |
| RNASEH1-AS1 | ENSG00000234171.2 |
| RP1-159A19.3 | ENSG00000235912.1 |
| RP1-179N16.6 | ENSG00000246982.6 |
| RP1-278E11.3 | ENSG00000180211.5 |
| RP1-40G4P.1 | ENSG00000231369.1 |
| RP11-100N21.1 | ENSG00000242262.1 |
| RP11-1018J11.1 | ENSG00000256211.1 |
| RP11-111F16.2 | ENSG00000229939.1 |
| RP11-138A9.2 | ENSG00000273319.1 |
| RP11-1415C14.4 | ENSG00000254701.3 |
| RP11-165H4.2 | ENSG00000236976.1 |
| RP11-170M17.2 | ENSG00000213609.3 |
| RP11-204C16.4 | ENSG00000217624.2 |
| RP11-214O14.1 | ENSG00000241651.4 |
| RP11-215A21.2 | ENSG00000236058.3 |
| RP11-253E3.1 | ENSG00000234589.4 |
| RP11-267J23.4 | ENSG00000198134.3 |
| RP11-26J3.3 | ENSG00000272518.1 |
| RPll-307E17.11 | ENSG00000282886.1 |
| RP11-30L3.2 | ENSG00000266696.1 |
| RP11-345K20.2 | ENSG00000229659.1 |
| RP11-366M4.1 | ENSG00000240674.1 |
| RP11-367E12.4 | ENSG00000253833.1 |
| RP11-367G18.2 | ENSG00000218208.1 |
| RP11-401L13.4 | ENSG00000224415.1 |
| RP11-421N8.1 | ENSG00000260747.1 |
| RP11-478C6.4 | ENSG00000250321.1 |
| RP11-488C13.1 | ENSG00000241081.1 |
| RP11-488L18.10 | ENSG00000259865.1 |
| RP11-490G8.1 | ENSG00000241556.1 |
| RP11-492M23.2 | ENSG00000229605.5 |
| RP11-505P4.7 | ENSG00000229862.6 |
| RP11-512F24.1 | ENSG00000232499.2 |
| RP11-546B8.5 | ENSG00000254012.1 |
| RP11-580J4.1 | ENSG00000251123.1 |
| RP11-589F5.4 | ENSG00000253366.3 |
| RP11-681N23.1 | ENSG00000243779.1 |
| RP11-69L16.5 | ENSG00000220472.1 |
| RP11-76H14.2 | ENSG00000217769.4 |
| RP11-771F20.1 | ENSG00000239344.1 |
| RP11-778D9.4 | ENSG00000228205.1 |
| RP11-77P16.4 | ENSG00000249846.6 |
| RP11-829H16.2 | ENSG00000213867.4 |
| RP11-846F4.10 | ENSG00000264930.1 |
| RP11-849F2.10 | ENSG00000271029.1 |
| RP11-864N7.2 | ENSG00000227615.1 |
| RP11-879F14.1 | ENSG00000267175.5 |
| RP11-889L3.1 | ENSG00000218227.3 |
| RP11-92K2.2 | ENSG00000231767.3 |
| RP11-941H19.1 | ENSG00000241746.1 |
| RP13-258O15.1 | ENSG00000225912.1 |
| RP3-393E18.1 | ENSG00000216480.2 |
| RP3-477M7.5 | ENSG00000232208.2 |
| RP4-682C21.2 | ENSG00000181227.3 |
| RP4-814D15.2 | ENSG00000225224.1 |
| RPL10AP6 | ENSG00000226360.5 |
| RPL12P38 | ENSG00000213228.5 |
| RPL12P42 | ENSG00000213253.5 |
| RPL13 | ENSG00000167526.13 |
| RPL13AP25 | ENSG00000136149.6 |
| RPL13P12 | ENSG00000215030.5 |
| RPL14P3 | ENSG00000241923.2 |
| RPL15P18 | ENSG00000228501.2 |
| RPL15P2 | ENSG00000240914.1 |
| RPL21P10 | ENSG00000239272.1 |
| RPL21P134 | ENSG00000233254.1 |
| RPL21P28 | ENSG00000220749.4 |
| RPL23AP18 | ENSG00000225338.1 |
| RPL26P35 | ENSG00000244229.1 |
| RPL27A | ENSG00000166441.12 |
| RPL27AP5 | ENSG00000182383.8 |
| RPL3 | ENSG00000100316.15 |
| RPL34P18 | ENSG00000240509.1 |
| RPL35P5 | ENSG00000225573.4 |
| RPL3P7 | ENSG00000225093.1 |
| RPL41P5 | ENSG00000256393.1 |
| RPL4P3 | ENSG00000230364.1 |
| RPL4P4 | ENSG00000229638.1 |
| RPL5P34 | ENSG00000234009.1 |
| RPL7AP30 | ENSG00000241741.1 |
| RPL7AP6 | ENSG00000242071.3 |
| RPL7AP66 | ENSG00000175886.10 |
| RPL7P23 | ENSG00000244363.3 |
| RPL7P26 | ENSG00000184612.8 |
| RPL8 | ENSG00000161016.16 |
| RPL9P25 | ENSG00000240821.1 |
| RPLP0P2 | ENSG00000243742.5 |
| RPLP2 | ENSG00000177600.8 |
| RPS10 | ENSG00000124614.13 |
| RPS11P5 | ENSG00000232888.4 |
| RPS16 | ENSG00000105193.8 |
| RPS19 | ENSG00000105372.6 |
| RPS20P10 | ENSG00000233971.1 |
| RPS20P14 | ENSG00000223803.1 |
| RPS23 | ENSG00000186468.12 |
| RPS26P13 | ENSG00000227887.1 |
| RPS26P15 | ENSG00000223416.3 |
| RPS26P28 | ENSG00000243538.1 |
| RPS26P47 | ENSG00000234354.3 |
| RPS27AP2 | ENSG00000232333.1 |
| RPS2P4 | ENSG00000196183.5 |
| RPS2P7 | ENSG00000235508.3 |
| RPS3AP25 | ENSG00000232385.2 |
| RPS3AP26 | ENSG00000214389.2 |
| RPS3AP47 | ENSG00000205871.5 |
| RPS4XP11 | ENSG00000234335.1 |
| RPS4XP17 | ENSG00000244097.1 |
| RPS5 | ENSG00000083845.8 |
| RPS7P10 | ENSG00000226525.5 |
| RPS7P11 | ENSG00000213326.4 |
| RPS7P14 | ENSG00000213695.3 |
| RPS7P3 | ENSG00000231940.1 |
| RPS9 | ENSG00000170889.13 |

TABLE 2-continued

Genes downregulated in patients with GBM

| Gene Name | GeneID |
|---|---|
| RPSAP12 | ENSG00000240087.3 |
| RPSAP14 | ENSG00000233984.1 |
| RPSAP15 | ENSG00000237506.3 |
| RPSAP18 | ENSG00000224261.2 |
| RPSAP3 | ENSG00000242952.1 |
| RPSAP61 | ENSG00000214016.3 |
| RPSAP8 | ENSG00000230592.2 |
| SAFB | ENSG00000160633.12 |
| SART1 | ENSG00000175467.14 |
| SAXO2 | ENSG00000188659.9 |
| SDCBPP2 | ENSG00000247570.2 |
| SEPT7-AS1 | ENSG00000228878.7 |
| 9-Sep | ENSG00000184640.17 |
| SERBP1 | ENSG00000142864.14 |
| SERF1B | ENSG00000205572.9 |
| SERPINB2 | ENSG00000197632.8 |
| SLC17A4 | ENSG00000146039.10 |
| SLC25A6P3 | ENSG00000232846.1 |
| SLC30A4 | ENSG00000104154.6 |
| SLC35F2 | ENSG00000110660.14 |
| SLC7A11 | ENSG00000151012.13 |
| SMARCE1P6 | ENSG00000214465.3 |
| SNHG3 | ENSG00000242125.3 |
| SNHG6 | ENSG00000245910.8 |
| SNRPFP1 | ENSG00000231878.1 |
| SPA17 | ENSG00000064199.6 |
| SPEN | ENSG00000065526.10 |
| SPTBN1 | ENSG00000115306.15 |
| SRSF5 | ENSG00000100650.15 |
| SUB1P1 | ENSG00000227203.3 |
| SUB1P3 | ENSG00000261612.1 |
| TAF15 | ENSG00000270647.5 |
| TBC1D10B | ENSG00000169221.13 |
| TCOF1 | ENSG00000070814.17 |
| TIGD1 | ENSG00000221944.5 |
| TMEM155 | ENSG00000164112.12 |
| TMSB4XP8 | ENSG00000187653.11 |
| TMUB2 | ENSG00000168591.15 |
| TOP1MT | ENSG00000184428.12 |
| TRA2B | ENSG00000136527.17 |
| tRNA-Ala-AGC-11-1 | tRNA-Ala-AGC-11-1 |
| tRNA-Ala-AGC-8-2 | tRNA-Ala-AGC-8-2 |
| tRNA-Arg-CCT-1-1 | tRNA-Arg-CCT-1-1 |
| tRNA-Arg-CCT-2-1 | tRNA-Arg-CCT-2-1 |
| tRNA-Arg-CCT-3-1 | tRNA-Arg-CCT-3-1 |
| tRNA-Asn-GTT-7-1 | tRNA-Asn-GTT-7-1 |
| tRNA-Cys-GCA-chr12-13 | tRNA-Cys-GCA-chr12-13 |
| tRNA-Glu-TTC-4-2 | tRNA-Glu-TTC-4-2 |
| tRNA-Gly-TCC-2-5 | tRNA-Gly-TCC-2-5 |
| tRNA-Ile-AAT-2-1 | tRNA-Ile-AAT-2-1 |
| tRNA-Leu-CAG-1-6 | tRNA-Leu-CAG-1-6 |
| tRNA-Leu-CAG-2-2 | tRNA-Leu-CAG-2-2 |
| tRNA-Lys-CTT-1-1 | tRNA-Lys-CTT-1-1 |
| tRNA-Lys-CTT-2-3 | tRNA-Lys-CTT-2-3 |
| tRNA-Lys-CTT-6-1 | tRNA-Lys-CTT-6-1 |
| tRNA-Lys-CTT-chr7-30 | tRNA-Lys-CTT-chr7-30 |
| TYSND1 | ENSG00000156521.13 |
| U2AF1 | ENSG00000160201.11 |
| U2AF2 | ENSG00000063244.12 |
| UBE2M | ENSG00000130725.7 |
| UBL5 | ENSG00000198258.10 |
| ULBP3 | ENSG00000131019.10 |
| UQCR11 | ENSG00000127540.11 |
| USH1C | ENSG00000006611.15 |
| VSIG2 | ENSG00000019102.11 |
| YBX1P1 | ENSG00000224861.1 |
| YBX1P10 | ENSG00000213866.3 |
| ZNF519P1 | ENSG00000232950.1 |
| ZNF571 | ENSG00000180479.13 |
| ZNF610 | ENSG00000167554.14 |
| ZNF727 | ENSG00000214652.5 |

TABLE 3

Genes upregulated in pre-treatment samples from patients who respond to Dacomitinib

| Gene Name | GeneID |
|---|---|
| FAM229B | ENSG00000203778.7 |
| ZNF35 | ENSG00000169981.10 |
| CTD-2647L4.4 | ENSG00000259366.1 |
| CABP5 | ENSG00000105507.2 |
| CYP20A1 | ENSG00000119004.15 |
| CEP126 | ENSG00000110318.13 |
| DTX2P1-UPK3BP1-PMS2P11 | ENSG00000265479.6 |
| RP11-507K12.1 | ENSG00000283321.1 |
| KRBA2 | ENSG00000184619.3 |
| CALD1 | ENSG00000122786.19 |
| LRFN1 | ENSG00000128011.4 |
| RP2 | ENSG00000102218.5 |
| SLC2A13 | ENSG00000151229.12 |
| CDKL3 | ENSG00000006837.11 |
| SLC8A3 | ENSG00000100678.18 |
| ANTXR2 | ENSG00000163297.16 |
| TIGD5 | ENSG00000179886.5 |
| AC074289.1 | ENSG00000225889.7 |
| RP11-932O9.7 | ENSG00000247728.2 |

TABLE 4

Genes down regulated in pre-treatment samples from patients who respond to Dacomitinib

| Gene Name | GeneID |
|---|---|
| tRNA-Lys-CTT-2-2 | tRNA-Lys-CTT-2-2 |
| tRNA-Pro-AGG-2-7 | tRNA-Pro-AGG-2-7 |
| LAMTOR2 | ENSG00000116586.11 |
| RAD51AP1 | ENSG00000111247.14 |
| DENND2A | ENSG00000146966.12 |
| A1BG | ENSG00000121410.11 |
| THSD1 | ENSG00000136114.15 |
| CSF1 | ENSG00000184371.13 |
| RP11-332M2.1 | ENSG00000203644.3 |
| ZNF717 | ENSG00000227124.8 |
| ZNF860 | ENSG00000197385.5 |
| ORC6 | ENSG00000091651.8 |
| C1orf50 | ENSG00000164008.14 |
| PSPH | ENSG00000146733.13 |
| HIST1H4C | ENSG00000197061.4 |
| CYP2U1 | ENSG00000155016.17 |
| THAP8 | ENSG00000161277.10 |
| TMEM192 | ENSG00000170088.13 |
| NAA20 | ENSG00000173418.11 |

TABLE 5

Reference Genes

| Gene Name | GeneID |
|---|---|
| ACAP2 | ENSG00000114331.13 |
| ACTB | ENSG00000075624.13 |
| ACTG1 | ENSG00000184009.9 |
| ACTN4 | ENSG00000130402.11 |
| ACTR2 | ENSG00000138071.13 |
| ACTR3 | ENSG00000115091.11 |
| ADAR | ENSG00000160710.15 |
| ADD1 | ENSG00000087274.16 |
| ANKRD12 | ENSG00000101745.16 |
| ANKRD17 | ENSG00000132466.17 |
| ANP32B | ENSG00000136938.8 |
| ANP32E | ENSG00000143401.14 |
| ARHGAP30 | ENSG00000186517.13 |
| ARHGDIB | ENSG00000111348.8 |
| ARPC2 | ENSG00000163466.15 |
| ARPC3 | ENSG00000111229.15 |
| ATF7IP | ENSG00000171681.12 |

TABLE 5-continued

Reference Genes

| Gene Name | GeneID |
|---|---|
| ATP5L | ENSG00000167283.7 |
| ATRX | ENSG00000085224.21 |
| BCLAF1 | ENSG00000029363.15 |
| BDP1 | ENSG00000145734.18 |
| BIN2 | ENSG00000110934.10 |
| BOD1L1 | ENSG00000038219.12 |
| BPTF | ENSG00000171634.16 |
| BRD2 | ENSG00000204256.12 |
| CALM1 | ENSG00000198668.10 |
| CAP1 | ENSG00000131236.16 |
| CAPZA1 | ENSG00000116489.12 |
| CAST | ENSG00000153113.23 |
| CCNI | ENSG00000118816.9 |
| CD37 | ENSG00000104894.11 |
| CDC42SE2 | ENSG00000158985.13 |
| CDV3 | ENSG00000091527.15 |
| CFL1 | ENSG00000172757.12 |
| CHD2 | ENSG00000173575.19 |
| CHMP3 | ENSG00000115561.15 |
| CLNS1A | ENSG00000074201.8 |
| CLTC | ENSG00000141367.11 |
| CMPK1 | ENSG00000162368.13 |
| CNBP | ENSG00000169714.16 |
| CNN2 | ENSG00000064666.14 |
| CORO1A | ENSG00000102879.15 |
| COTL1 | ENSG00000103187.7 |
| CSDE1 | ENSG00000009307.15 |
| CSK | ENSG00000103653.16 |
| DAZAP2 | ENSG00000183283.15 |
| DDX5 | ENSG00000108654.12 |
| DDX6 | ENSG00000110367.11 |
| DEK | ENSG00000124795.14 |
| DIAPH1 | ENSG00000131504.15 |
| DNAJA1 | ENSG00000086061.15 |
| EEF1A1 | ENSG00000156508.17 |
| EEF1B2 | ENSG00000114942.13 |
| EEF1G | ENSG00000254772.9 |
| EEF2 | ENSG00000167658.15 |
| EIF1 | ENSG00000173812.10 |
| EIF2S2 | ENSG00000125977.6 |
| EIF3E | ENSG00000104408.9 |
| EIF3G | ENSG00000130811.11 |
| EIF3H | ENSG00000147677.10 |
| EIF4B | ENSG00000063046.17 |
| ELF1 | ENSG00000120690.14 |
| ERBIN | ENSG00000112851.14 |
| ETS1 | ENSG00000134954.14 |
| FAM107B | ENSG00000065809.13 |
| FBXW7 | ENSG00000109670.13 |
| FLI1 | ENSG00000151702.16 |
| FTH1 | ENSG00000167996.15 |
| FYB | ENSG00000082074.15 |
| FYTTD1 | ENSG00000122068.12 |
| GAPDH | ENSG00000111640.14 |
| GIMAP4 | ENSG00000133574.9 |
| GIMAP7 | ENSG00000179144.4 |
| GNA13 | ENSG00000120063.9 |
| GNAI2 | ENSG00000114353.16 |
| GNAS | ENSG00000087460.23 |
| GNB1 | ENSG00000078369.17 |
| GRK6 | ENSG00000198055.10 |
| H3F3A | ENSG00000163041.9 |
| HCLS1 | ENSG00000180353.10 |
| HLA-A | ENSG00000206503.11 |
| HLA-B | ENSG00000234745.9 |
| HMGB1 | ENSG00000189403.14 |
| HNRNPA2B1 | ENSG00000122566.20 |
| HNRNPC | ENSG00000092199.17 |
| HNRNPK | ENSG00000165119.19 |
| HNRNPM | ENSG00000099783.11 |
| HNRNPR | ENSG00000125944.18 |
| HOOK3 | ENSG00000168172.8 |
| HSP90AA1 | ENSG00000080824.18 |
| HSP90AB1 | ENSG00000096384.19 |
| HSPA8 | ENSG00000109971.13 |
| IK | ENSG00000113141.16 |
| IQGAP1 | ENSG00000140575.12 |
| JAK1 | ENSG00000162434.11 |
| KIF5B | ENSG00000170759.10 |
| KMT2C | ENSG00000055609.17 |
| KMT2E | ENSG00000005483.20 |
| KPNB1 | ENSG00000108424.9 |
| LAPTM5 | ENSG00000162511.7 |
| LASP1 | ENSG00000002834.17 |
| LCP1 | ENSG00000136167.13 |
| LCP2 | ENSG00000043462.11 |
| LRRFIP1 | ENSG00000124831.18 |
| LSP1 | ENSG00000130592.14 |
| MAN1A2 | ENSG00000198162.12 |
| MAP4K4 | ENSG00000071054.16 |
| MAPRE1 | ENSG00000101367.8 |
| MBD2 | ENSG00000134046.11 |
| MCL1 | ENSG00000143384.12 |
| MGEA5 | ENSG00000198408.13 |
| MIER1 | ENSG00000198160.14 |
| MOB1A | ENSG00000114978.17 |
| MORC3 | ENSG00000159256.12 |
| MSN | ENSG00000147065.16 |
| MYL12A | ENSG00000101608.12 |
| MYL12B | ENSG00000118680.12 |
| MYL6 | ENSG00000092841.18 |
| N4BP2L2 | ENSG00000244754.8 |
| NAP1L1 | ENSG00000187109.13 |
| NAP1L4 | ENSG00000205531.12 |
| NBR1 | ENSG00000188554.13 |
| NCL | ENSG00000115053.15 |
| NFATC3 | ENSG00000072736.18 |
| NIN | ENSG00000100503.23 |
| NIPBL | ENSG00000164190.16 |
| NONO | ENSG00000147140.15 |
| NPM1 | ENSG00000181163.13 |
| NUCKS1 | ENSG00000069275.12 |
| OSBPL8 | ENSG00000091039.16 |
| PABPC1 | ENSG00000070756.14 |
| PAIP2 | ENSG00000120727.12 |
| PAK2 | ENSG00000180370.10 |
| PANK3 | ENSG00000120137.6 |
| PCBP1 | ENSG00000169564.6 |
| PCBP2 | ENSG00000197111.15 |
| PCM1 | ENSG00000078674.17 |
| PCMTD1 | ENSG00000168300.13 |
| PDS5A | ENSG00000121892.14 |
| PFDN5 | ENSG00000123349.13 |
| PFN1 | ENSG00000108518.7 |
| PICALM | ENSG00000073921.17 |
| PNRC1 | ENSG00000146278.10 |
| PNRC2 | ENSG00000189266.11 |
| PPP1R9B | ENSG00000108819.10 |
| PRKAR1A | ENSG00000108946.14 |
| PRRC2C | ENSG00000117523.15 |
| PTBP3 | ENSG00000119314.15 |
| PTMA | ENSG00000187514.15 |
| RAB8B | ENSG00000166128.12 |
| RAC1 | ENSG00000136238.17 |
| RAC2 | ENSG00000128340.14 |
| RACK1 | ENSG00000204628.11 |
| RAD23B | ENSG00000119318.12 |
| RANBP2 | ENSG00000153201.15 |
| RASSF5 | ENSG00000266094.7 |
| RBM25 | ENSG00000119707.13 |
| RBM33 | ENSG00000184863.10 |
| RBM39 | ENSG00000131051.21 |
| RBMX | ENSG00000147274.14 |
| ROCK1 | ENSG00000067900.7 |
| RPL10A | ENSG00000198755.10 |
| RPL11 | ENSG00000142676.12 |
| RPL12 | ENSG00000197958.12 |
| RPL13A | ENSG00000142541.16 |
| RPL14 | ENSG00000188846.13 |
| RPL15 | ENSG00000174748.18 |
| RPL17 | ENSG00000265681.7 |
| RPL19 | ENSG00000108298.9 |

TABLE 5-continued

Reference Genes

| Gene Name | GeneID |
|---|---|
| RPL21 | ENSG00000122026.10 |
| RPL22 | ENSG00000116251.9 |
| RPL23 | ENSG00000125691.12 |
| RPL23A | ENSG00000198242.13 |
| RPL26 | ENSG00000161970.12 |
| RPL27 | ENSG00000131469.12 |
| RPL28 | ENSG00000108107.13 |
| RPL30 | ENSG00000156482.10 |
| RPL31 | ENSG00000071082.10 |
| RPL32 | ENSG00000144713.12 |
| RPL35 | ENSG00000136942.14 |
| RPL37A | ENSG00000197756.9 |
| RPL38 | ENSG00000172809.12 |
| RPL4 | ENSG00000174444.14 |
| RPL5 | ENSG00000122406.12 |
| RPL6 | ENSG00000089009.15 |
| RPL7 | ENSG00000147604.13 |
| RPLP0 | ENSG00000089157.15 |
| RPLP1 | ENSG00000137818.11 |
| RPS11 | ENSG00000142534.6 |
| RPS12 | ENSG00000112306.7 |
| RPS13 | ENSG00000110700.6 |
| RPS14 | ENSG00000164587.11 |
| RPS15 | ENSG00000115268.9 |
| RPS15A | ENSG00000134419.15 |
| RPS17 | ENSG00000182774.10 |
| RPS18 | ENSG00000231500.6 |
| RPS2 | ENSG00000140988.15 |
| RPS20 | ENSG00000008988.9 |
| RPS24 | ENSG00000138326.18 |
| RPS25 | ENSG00000118181.10 |
| RPS27A | ENSG00000143947.12 |
| RPS29 | ENSG00000213741.8 |
| RPS3 | ENSG00000149273.14 |
| RPS3A | ENSG00000145425.9 |
| RPS4X | ENSG00000198034.10 |
| RPS6 | ENSG00000137154.12 |
| RPS7 | ENSG00000171863.12 |
| RPS8 | ENSG00000142937.11 |
| RPSA | ENSG00000168028.13 |
| RSL1D1 | ENSG00000171490.12 |
| RSRC1 | ENSG00000174891.12 |
| SEC62 | ENSG00000008952.16 |
| SEPT7 | ENSG00000122545.18 |
| SERF2 | ENSG00000140264.19 |
| SET | ENSG00000119335.16 |
| SETD2 | ENSG00000181555.19 |
| SF3B2 | ENSG00000087365.15 |
| SFPQ | ENSG00000116560.10 |
| SKP1 | ENSG00000113558.15 |
| SLC25A6 | ENSG00000169100.13 |
| SMARCA5 | ENSG00000153147.5 |
| SMARCC1 | ENSG00000173473.10 |
| SMARCC2 | ENSG00000139613.11 |
| SMC1A | ENSG00000072501.17 |
| SMCHD1 | ENSG00000101596.14 |
| SNRNP200 | ENSG00000144028.14 |
| SRRM1 | ENSG00000133226.16 |
| SRSF4 | ENSG00000116350.16 |
| ST13 | ENSG00000100380.13 |
| STK10 | ENSG00000072786.12 |
| STK17B | ENSG00000081320.10 |
| STK4 | ENSG00000101109.11 |
| SYF2 | ENSG00000117614.9 |
| THRAP3 | ENSG00000054118.13 |
| TMA7 | ENSG00000232112.3 |
| TMSB10 | ENSG00000034510.5 |
| TMSB4X | ENSG00000205542.10 |
| TPM3 | ENSG00000143549.19 |
| TPR | ENSG00000047410.13 |
| TPT1 | ENSG00000133112.16 |
| TRIM44 | ENSG00000166326.6 |
| TUBA1B | ENSG00000123416.15 |
| TUBB | ENSG00000196230.12 |
| TXNIP | ENSG00000265972.5 |
| UBAP2 | ENSG00000137073.20 |
| UBB | ENSG00000170315.13 |
| UBC | ENSG00000150991.14 |
| UBXN1 | ENSG00000162191.13 |
| UPF2 | ENSG00000151461.19 |
| UTRN | ENSG00000152818.18 |
| VASP | ENSG00000125753.13 |
| VIM | ENSG00000026025.14 |
| VTI1B | ENSG00000100568.10 |
| WDR1 | ENSG00000071127.16 |
| WIPF1 | ENSG00000115935.17 |
| XRCC5 | ENSG00000079246.15 |
| XRN2 | ENSG00000088930.7 |
| YBX1 | ENSG00000065978.18 |
| YTHDC1 | ENSG00000083896.12 |
| YWHAZ | ENSG00000164924.17 |
| ZC3H13 | ENSG00000123200.16 |

TABLE 6

Genes with low CV values that can be used as reference genes.

| Gene Name | CV (%) across all GBM patient samples | CV (%) across pre-treatment and healthy samples |
|---|---|---|
| GAPDH | 4.38 | 3.51 |
| ACTB | 2.79 | 2.5 |
| VIM | 3.3 | 2.77 |
| EEF2 | 3.42 | 2.22 |
| RPS2 | 4.75 | 2.51 |
| RPS3 | 3.89 | 2.66 |
| RPL15 | 4.59 | 2.7 |
| RPL22 | 4.38 | 2.74 |
| UBC | 2.42 | 2.61 |
| NCL | 2.55 | 1.99 |

TABLE 7

Genes differentially expressed in pre-treatment vs post-treatment patient samples

| Gene Name | GeneID |
|---|---|
| ZNF302 | ENSG00000089335.20 |
| DNMT3A | ENSG00000119772.16 |
| BHLHA15 | ENSG00000180535.3 |
| CTD-2132N18.3 | ENSG00000267261.5 |
| AC009501.4 | ENSG00000231609.5 |
| hsa-mir-16-1 | MI0000070 |
| H3F3AP4 | ENSG00000235655.3 |
| SPINK13 | ENSG00000214510.9 |
| C16orf90 | ENSG00000215131.10 |
| OVOL1 | ENSG00000172818.9 |
| TP53 | ENSG00000141510.16 |
| RP1-102E24.6 | ENSG00000256913.1 |
| RP11-516A11.1 | ENSG00000228328.2 |
| ZNF610 | ENSG00000167554.14 |
| RPL5P34 | ENSG00000234009.1 |
| RP11-1217F2.20 | ENSG00000283481.1 |
| CTD-2561J22.2 | ENSG00000213976.4 |
| RP11-872D17.8 | ENSG00000254979.5 |
| HRG | ENSG00000113905.4 |
| RP11-416L21.1 | ENSG00000213495.3 |
| RP11-34P13.15 | ENSG00000268903.1 |
| RPL7P9 | ENSG00000137970.7 |
| CTD-2021A8.3 | ENSG00000227080.2 |
| TCAP | ENSG00000173991.7 |
| KRTAP23-1 | ENSG00000186980.6 |
| RP11-982M15.2 | ENSG00000258430.1 |
| AC010524.2 | ENSG00000268686.1 |
| HS1BP3-IT1 | ENSG00000231948.2 |

TABLE 7-continued

Genes differentially expressed in pre-treatment vs post-treatment patient samples

| Gene Name | GeneID |
|---|---|
| RP11-543P15.1 | ENSG00000227081.5 |
| GRTP1-AS1 | ENSG00000225083.1 |
| RP1-181J22.1 | ENSG00000244535.1 |
| CTC-498J12.3 | ENSG00000248664.1 |
| RP11-420K14.1 | ENSG00000268278.1 |
| CDON | ENSG00000064309.14 |
| RP4-761J14.8 | ENSG00000219410.5 |
| RP11-560J1.2 | ENSG00000271888.1 |
| HIST2H3PS2 | ENSG00000203818.7 |
| ORM2 | ENSG00000228278.3 |
| FAHD2CP | ENSG00000231584.8 |
| CTB-152G17.6 | ENSG00000272918.1 |
| TLX1 | ENSG00000107807.12 |
| CCT6B | ENSG00000132141.13 |
| RPS15AP1 | ENSG00000214535.3 |
| DRICH1 | ENSG00000189269.12 |
| TBCAP1 | ENSG00000226781.1 |
| RP11-378J18.8 | ENSG00000272750.1 |
| ERVK-28 | ENSG00000267696.6 |
| hsa-mir-7641-2 | MI0024976 |
| LA16c-380H5.5 | ENSG00000272079.2 |
| RP11-420H19.3 | ENSG00000213291.3 |
| ZNF888 | ENSG00000213793.4 |
| DCANP1 | ENSG00000251380.3 |
| GALNT12 | ENSG00000119514.6 |
| RP11-67A1.2 | ENSG00000261864.1 |
| AC083884.8 | ENSG00000232729.7 |
| SLC19A3 | ENSG00000135917.13 |
| AC096558.1 | ENSG00000228655.6 |
| PRDX3P1 | ENSG00000229598.1 |
| ASMT | ENSG00000196433.12 |
| RP11-288H12.3 | ENSG00000213073.2 |
| RP11-111A22.1 | ENSG00000259536.5 |
| RP13-104F24.3 | ENSG00000265298.1 |
| ZDHHC11 | ENSG00000188818.12 |
| RP4-614O4.11 | ENSG00000261582.1 |
| RP11-578F21.9 | ENSG00000260844.2 |
| SNHG6 | ENSG00000245910.8 |
| ASS1P2 | ENSG00000223922.1 |
| CTC-273B12.5 | ENSG00000268530.5 |
| RP11-923I11.3 | ENSG00000260122.1 |
| SEPT14 | ENSG0000054997.8 |
| RP11-350E12.5 | ENSG00000238110.1 |
| RP13-270P17.1 | ENSG00000264235.5 |
| RP11-867G23.4 | ENSG00000254452.1 |
| FTH1P8 | ENSG00000219507.4 |
| RP11-974F13.5 | ENSG00000248769.1 |
| TBC1D3G | ENSG00000260287.4 |
| GBP7 | ENSG00000213512.1 |
| RP11-421L21.3 | ENSG00000233184.6 |
| LYSMD1 | ENSG00000163155.11 |
| SLC7A5P2 | ENSG00000258186.2 |
| RP11-553K23.2 | ENSG00000214280.3 |
| RP11-1000B6.5 | ENSG00000244952.2 |
| AC002116.8 | ENSG00000248101.2 |
| GJA1P1 | ENSG00000176857.5 |
| RP11-92K2.2 | ENSG00000231767.3 |
| RP11-710M11.1 | ENSG00000266373.1 |
| NR1I3 | ENSG00000143257.11 |
| RP11-182J1.12 | ENSG00000259244.1 |
| ZDHHC9 | ENSG00000188706.12 |
| RPS7P1 | ENSG00000263266.2 |
| RP11-166N17.1 | ENSG00000227253.3 |
| MRPL2P1 | ENSG00000257480.1 |
| RP11-889L3.1 | ENSG00000218227.3 |
| RP11-74E22.5 | ENSG00000272770.1 |
| GAPDHP60 | ENSG00000248180.1 |
| CYP2C19 | ENSG00000165841.9 |
| RP11-16C1.2 | ENSG00000264853.1 |
| NEK5 | ENSG00000197168.11 |
| hsa-mir-1246 | MI0006381 |
| RP11-120K18.3 | ENSG00000261245.2 |
| PTMAP2 | ENSG00000197744.5 |
| IL27 | ENSG00000197272.2 |
| RP11-592N21.1 | ENSG00000212664.5 |
| RP11-445N18.3 | ENSG00000228462.1 |
| RAB19 | ENSG00000146955.10 |
| IL11 | ENSG00000095752.6 |
| HS6ST1P1 | ENSG00000187952.9 |
| HNRNPA1P48 | ENSG00000224578.4 |
| HSPB2-C11orf52 | ENSG00000254445.1 |
| LA16c-306E5.3 | ENSG00000263212.2 |
| SYS1-DBNDD2 | ENSG00000254806.5 |
| RP11-701I24.1 | ENSG00000255291.2 |
| RP11-367J7.3 | ENSG00000227217.1 |
| AC007743.1 | ENSG00000233251.7 |
| CTA-246H3.8 | ENSG00000230637.2 |
| PTGER4P2-CDK2AP2P2 | ENSG00000275450.1 |
| RP3-469D22.1 | ENSG00000238084.4 |
| RIBC2 | ENSG00000128408.8 |
| RP3-508I15.18 | ENSG00000244491.1 |
| RP1-111D6.3 | ENSG00000228408.6 |
| FOXS1 | ENSG00000179772.7 |
| ST13P15 | ENSG00000243759.1 |
| RP11-154H23.3 | ENSG00000270562.1 |
| SMG7-AS1 | ENSG00000232860.7 |
| MUC20P1 | ENSG00000224769.1 |
| MYLK-AS1 | ENSG00000239523.5 |
| STAG3 | ENSG00000066923.17 |
| RP11-256P1.1 | ENSG00000249971.1 |
| RPL23AP88 | ENSG00000271153.1 |
| WASIR2 | ENSG00000231439.4 |
| CCDC74A | ENSG00000163040.14 |
| CA7 | ENSG00000168748.13 |
| RP11-585P4.6 | ENSG00000273987.1 |
| FAUP1 | ENSG00000235297.3 |
| RP13-644M16.4 | ENSG00000196472.4 |
| OR2F2 | ENSG00000221910.2 |
| FAM87B | ENSG00000177757.2 |
| ADORA2B | ENSG00000170425.3 |
| RP11-668G10.2 | ENSG00000229894.6 |
| RP11-701P16.2 | ENSG00000251139.2 |
| C1QTNF3 | ENSG00000082196.20 |
| ARRDC5 | ENSG00000205784.2 |
| RP11-263K19.6 | ENSG00000236263.1 |
| CTC-246B18.8 | ENSG00000268262.1 |
| CBLN2 | ENSG00000141668.9 |
| RP11-517A5.6 | ENSG00000263029.1 |
| RPS4XP11 | ENSG00000234335.1 |
| AP003774.6 | ENSG00000231680.1 |
| ZSCAN10 | ENSG00000130182.7 |
| RP11-445H22.3 | ENSG00000283440.1 |
| ZNF157 | ENSG00000147117.7 |
| CTB-47B8.5 | ENSG00000213414.3 |
| KAZALD1 | ENSG00000107821.14 |
| RP11-798G7.7 | ENSG00000267246.1 |
| MAN1B1-AS1 | ENSG00000268996.3 |
| AC004453.8 | ENSG00000146677.7 |
| PRPF38AP1 | ENSG00000225053.1 |
| RP11-51L5.7 | ENSG00000270033.1 |
| ST13P11 | ENSG00000213368.3 |
| MIMT1 | ENSG00000268654.1 |
| GLOD5 | ENSG00000171433.11 |
| RP11-290D2.6 | ENSG00000273149.1 |
| RP11-930O11.2 | ENSG00000259483.1 |
| LINC00264 | ENSG00000233261.3 |
| TRIML2 | ENSG00000179046.8 |
| DIO3OS | ENSG00000258498.7 |
| PVRIG2P | ENSG00000235333.3 |
| AC064874.1 | ENSG00000222007.6 |
| NEDD8-MDP1 | ENSG00000255526.6 |
| RP11-314A20.5 | ENSG00000261898.2 |
| RP11-106D4.3 | ENSG00000276393.1 |
| AL591893.1 | ENSG00000229021.2 |
| RP5-878I13.1 | ENSG00000274374.1 |
| RP11-65B7.2 | ENSG00000281883.1 |
| TNFSF15 | ENSG00000181634.7 |

TABLE 7-continued

Genes differentially expressed in pre-treatment vs post-treatment patient samples

| Gene Name | GeneID |
|---|---|
| SDHDP6 | ENSG00000224183.1 |
| CTB-111H14.1 | ENSG00000243797.6 |
| GAS1RR | ENSG00000226237.1 |

What is claimed is:

1. A method of treating glioblastoma in a subject, the method comprising:
   (1) determining the expression level of at least one gene selected from FAM229B, ZNF35, CTD-2647L4.4, CABP5, CYP20A1, CEP126, DTX2P1-UPK3BP1-PMS2P11, RP11-507K12.1, KRBA2, CALD1, LRFN1, RP2, SLC2A13, CDKL3, SLC8A3, ANTXR2, TIGD5, AC074289.1 and RP11-932O9.7, and the expression level of at least one reference gene in exosomal RNA extracted from a biological sample from the subject;
   (2) normalizing the expression level of the at the least one gene by dividing the expression level of the at least one gene by the expression level of the at least one reference gene;
   (3) determining that the normalized expression level of the at least one gene in the biological sample is greater than a corresponding predetermined cutoff value; and
   (4) administering at least one therapeutically effective amount of dacomitinib to the subject.

2. The method of claim 1, wherein the at least one gene comprises ZNF35.

3. The method of claim 1, wherein the at least one reference gene comprises at least one gene selected from GAPDH, ACTB, VIM, EEF2, RPS2, RPS3, RPL15, RPL22, UBC, and NCL.

4. The method of claim 3, wherein the at least one reference gene comprises GAPDH.

5. The method of claim 1, wherein the biological sample is a blood, plasma, serum, urine or cerebrospinal fluid (CSF) sample.

6. The method of claim 1, wherein determining the expression level of the at least one gene and the at least one reference gene in step (1) comprises using quantitative reverse transcription PCR or sequencing.

7. A method of treating glioblastoma in a subject, the method comprising:
   (1) determining the expression level of at least one gene selected from tRNA-Lys-CTT-2-2, tRNA-Pro-AGG-2-7, LAMTOR2, RAD51AP1, DENND2A, A1BG, THSD1, CSF1, RP11-332M2.1, ZNF717, ZNF860, ORC6, C1orf50, PSPH, HIST1H4C, CYP2U1, THAP8, TMEM192, and NAA20, and the expression level of at least one reference gene in exosomal RNA extracted from a biological sample from the subject;
   (2) normalizing the expression level of the at the least one gene by dividing the expression level of the at least one gene by the expression level of the at least one reference gene;
   (3) determining that the normalized expression level of the at least one gene in the biological sample is less than a corresponding predetermined cutoff value; and
   (4) administering at least one therapeutically effective amount of dacomitinib to the subject.

8. The method of claim 7, wherein the at least one gene comprises LAMTOR2.

9. The method of claim 7, wherein the at least one reference gene comprises at least one gene selected from GAPDH ACTB, VIM, EEF2, RPS2, RPS3, RPL15, RPL22, UBC, and NCL.

10. The method of claim 9, wherein the at least one reference gene comprises GAPDH.

11. The method of claim 7, wherein the biological sample is a blood, plasma, serum, urine or cerebrospinal fluid (C SF) sample.

12. The method of claim 7, wherein determining the expression level of the at least one gene and the at least one reference gene in step (1) comprises using quantitative reverse transcription PCR or sequencing.

13. A method of treating glioblastoma in a subject, the method comprising:
   (1) determining the expression level of at least one gene selected from CREBBP, CXCR2 and S100A9 and the expression level of at least one reference gene in exosomal RNA extracted from a biological sample isolated from the subject;
   (2) normalizing the expression level of the at least one gene by dividing the expression level of the at least one gene by the expression level of the at least one reference gene;
   (3) determining that the normalized expression level of the at least one gene is greater than a predetermined cutoff value; and
   (4) administering at least one therapeutically effective amount of at least one glioblastoma therapy to the subject.

14. The method of claim 13, wherein the at least one reference gene comprises at least one gene selected from GAPDH, ACTB, VIM, EEF2, RPS2, RPS3, RPL15, RPL22, UBC, and NCL.

15. The method of claim 14, wherein the at least one reference gene comprises GAPDH.

16. The method of claim 13, wherein the biological sample is a blood, plasma, serum, urine or cerebrospinal fluid (CSF) sample.

17. The method of claim 13, wherein determining the expression level of the at least one gene and the at least one reference gene in step (1) comprises using quantitative reverse transcription PCR or sequencing.

18. The method of claim 13, wherein the at least one glioblastoma therapy comprises administering to the subject at least one anti-cancer agent, radiation treatment, immunotherapy, surgery, radiation therapy, targeted therapy, hormone therapy, stem cell transplant or any combination thereof.

* * * * *